United States Patent
Collins et al.

US007531162B2

(10) Patent No.: US 7,531,162 B2
(45) Date of Patent: May 12, 2009

(54) TRANSCOBALAMIN RECEPTOR BINDING CONJUGATES USEFUL FOR TREATING ABNORMAL CELLULAR PROLIFERATION

(75) Inventors: Douglas A. Collins, Rochester, MN (US); Henricus P. C. Hogenkamp, Roseville, MN (US)

(73) Assignees: Mayo Foundation for Medical Education and Research, Rochester, MN (US); Regents of the University of Minnesota, Minneapolis, MN (US)

( * ) Notice: Subject to any disclaimer, the term of this patent is extended or adjusted under 35 U.S.C. 154(b) by 118 days.

(21) Appl. No.: 11/353,810

(22) Filed: Feb. 13, 2006

(65) Prior Publication Data

US 2006/0166862 A1    Jul. 27, 2006

Related U.S. Application Data

(63) Continuation of application No. 10/027,593, filed on Oct. 25, 2001, now abandoned.

(60) Provisional application No. 60/243,082, filed on Oct. 25, 2000, provisional application No. 60/243,112, filed on Oct. 25, 2000.

(51) Int. Cl.
*A01N 43/04* (2006.01)
*A61K 51/00* (2006.01)
*A61K 31/70* (2006.01)
*A61M 36/14* (2006.01)
*C07H 23/00* (2006.01)

(52) U.S. Cl. .............. 424/1.73; 424/1.11; 424/1.65; 536/26.4; 536/26.44; 514/27

(58) Field of Classification Search .............. None
See application file for complete search history.

(56) References Cited

U.S. PATENT DOCUMENTS

| 638,752 A | 12/1899 | Perkins |
|---|---|---|
| 3,494,769 A | 2/1970 | Tressler |
| 3,627,788 A | 12/1971 | Bouchaudon |
| 3,936,440 A | 2/1976 | Nath |
| 3,981,863 A | 9/1976 | Niswender et al. |
| 4,209,614 A | 6/1980 | Bernstein et al. |
| 4,279,859 A | 7/1981 | Gutcho et al. |
| 4,283,342 A | 8/1981 | Yolles |
| 4,301,140 A | 11/1981 | Frank et al. |
| 4,399,163 A | 8/1983 | Brennen et al. |
| 4,411,925 A | 10/1983 | Brennan et al. |
| 4,423,029 A | 12/1983 | Rizzi |
| 4,465,775 A | 8/1984 | Houts |
| 4,612,302 A | 9/1986 | Szabo et al. |
| 4,672,028 A | 6/1987 | Olson |
| 4,686,620 A | 8/1987 | Hruby et al. |
| 4,853,371 A | 8/1989 | Coy et al. |
| 4,959,356 A | 9/1990 | Miura et al. |
| 4,976,960 A | 12/1990 | Grossman et al. |
| 4,987,071 A | 1/1991 | Cech et al. |
| 5,057,301 A | 10/1991 | Wilbur et al. |
| 5,187,107 A | 2/1993 | Watkins et al. |
| 5,286,853 A | 2/1994 | Spielvogel et al. |
| 5,308,606 A | 5/1994 | Wilson et al. |
| 5,372,808 A | 12/1994 | Blatt et al. |
| 5,405,598 A | 4/1995 | Schinazi et al. |
| 5,405,839 A | 4/1995 | Toraya et al. |
| 5,428,023 A | 6/1995 | Russell-Jones et al. |
| 5,449,720 A | 9/1995 | Russell-Jones et al. |
| 5,462,724 A | 10/1995 | Schinazi et al. |
| 5,514,695 A | 5/1996 | Begeron |
| 5,548,064 A | 8/1996 | Russell-Jones et al. |
| 5,556,644 A | 9/1996 | Chandra |
| 5,559,796 A | 9/1996 | Edem et al. |
| 5,569,477 A | 10/1996 | Nesbitt |
| 5,574,018 A | 11/1996 | Habberfield et al. |
| 5,578,336 A | 11/1996 | Monte |
| 5,589,463 A | 12/1996 | Russell-Jones et al. |
| 5,599,796 A | 2/1997 | Schinazi et al. |
| 5,608,060 A | 3/1997 | Axworthy et al. |
| 5,630,786 A | 5/1997 | Griffin et al. |
| 5,736,392 A | 4/1998 | Hawley-Nelson et al. |
| 5,739,313 A | 4/1998 | Collins et al. |
| 5,789,573 A | 8/1998 | Baker et al. |
| 5,807,832 A | 9/1998 | Russell-Jones et al. |
| 5,820,903 A | 10/1998 | Fleury et al. |
| 5,840,880 A | 11/1998 | Morgan, Jr. et al. |
| 5,869,084 A | 2/1999 | Paradissis et al. |
| 5,869,465 A | 2/1999 | Morgan, Jr. et al. |

(Continued)

FOREIGN PATENT DOCUMENTS

| DE | 1811 518 | 7/1969 |
|---|---|---|
| EP | 0 005 834 | 10/1981 |
| EP | 0 069 450 | 1/1983 |
| EP | 0 220 030 | 4/1987 |
| EP | 0 165 716 | 1/1990 |
| EP | 506 242 | 12/1998 |
| EP | 0 804 456 | 8/2002 |
| ES | 2 088 364 | 8/1996 |
| JP | 58-046027 | 3/1983 |
| WO | 89/01475 | 2/1989 |

(Continued)

OTHER PUBLICATIONS

Alam et al., "Boronated compounds for neutron capture therapy," *Strahlentherapie and Onkologie*, 1989, 165(2/3):121-123.
Aldrain-Herrada et al., "A peptide nucleic acid (PNA) is more rapidly internalized in cultured neurons when coupled to a retro-inverso delivery peptide. The antisense activity depresses the target mRNA and protein in magnocellular oxytocin neurons," *Nucl. Acid Res.*, 1998, 26(21):4910-4916.

(Continued)

*Primary Examiner*—Traviss C McIntosh, III
(74) *Attorney, Agent, or Firm*—Fish & Richardson P.C.

(57) ABSTRACT

An agent, composition and method for the treatment, prophylaxis and/or diagnosis of proliferative disorders, which is highly and efficiently absorbed at the site of abnormal cellular proliferation is disclosed.

9 Claims, 6 Drawing Sheets

U.S. PATENT DOCUMENTS

| | | | |
|---|---|---|---|
| 5,869,466 A | 2/1999 | Russell-Jones et al. | |
| 5,872,107 A | 2/1999 | Schinazi et al. | |
| 5,877,165 A | 3/1999 | Miura et al. | |
| 5,879,465 A | 3/1999 | McKevitt et al. | |
| 5,925,377 A | 7/1999 | Gerth et al. | |
| 5,925,625 A | 7/1999 | Merkus | |
| 5,936,082 A | 8/1999 | Bauer | |
| 5,948,443 A | 9/1999 | Riley et al. | |
| 5,955,321 A | 9/1999 | Bijl | |
| 5,964,224 A | 10/1999 | Kaji | |
| 5,985,339 A | 11/1999 | Kamarei | |
| 6,004,533 A | 12/1999 | Collins et al. | |
| 6,015,887 A | 1/2000 | Teng | |
| 6,017,902 A | 1/2000 | Glass et al. | |
| 6,022,853 A | 2/2000 | Kuberasampath et al. | |
| 6,030,650 A | 2/2000 | Kamarei | |
| 6,039,978 A | 3/2000 | Bangs et al. | |
| 6,046,307 A | 4/2000 | Shay et al. | |
| 6,056,973 A | 5/2000 | Allen et al. | |
| 6,071,545 A | 6/2000 | Hendler et al. | |
| 6,074,625 A | 6/2000 | Hawthorne et al. | |
| 6,077,557 A | 6/2000 | Gordon et al. | |
| 6,083,926 A | 7/2000 | Morgan, Jr. et al. | |
| 6,083,966 A | 7/2000 | Bergeron, Jr. | |
| 6,093,425 A | 7/2000 | Kamarei | |
| 6,093,701 A | 7/2000 | Wolff et al. | |
| 6,096,290 A | 8/2000 | Collins et al. | |
| 6,110,472 A | 8/2000 | Levere et al. | |
| 6,121,249 A | 9/2000 | Weissman et al. | |
| 6,126,980 A | 10/2000 | Smith et al. | |
| 6,150,341 A | 11/2000 | Russell-Jones et al. | |
| 6,153,737 A | 11/2000 | Manoharan et al. | |
| 6,159,502 A | 12/2000 | Russell-Jones et al. | |
| 6,159,734 B1 | 12/2000 | McKay et al. | |
| 6,165,720 A | 12/2000 | Felger et al. | |
| 6,165,789 A | 12/2000 | Monia et al. | |
| 6,180,766 B1 | 1/2001 | Schinazi et al. | |
| 6,183,723 B1 | 2/2001 | Seetharam et al. | |
| 6,211,355 B1 | 4/2001 | Collins et al. | |
| 6,214,535 B1 | 4/2001 | Matsumori | |
| 6,221,397 B1 | 4/2001 | Russell-Jones et al. | |
| 6,262,253 B1 | 7/2001 | Russell-Jones et al. | |
| 6,274,564 B1 | 8/2001 | Sarill et al. | |
| 6,291,184 B1 | 9/2001 | Gold et al. | |
| 6,315,978 B1 | 11/2001 | Grissom et al. | |
| 6,316,198 B1 | 11/2001 | Skouv et al. | |
| 6,395,492 B1 | 5/2002 | Manoharan et al. | |
| 6,613,305 B1 | 9/2003 | Collins et al. | |
| 6,806,363 B1 * | 10/2004 | Collins et al. | 536/26.4 |
| 6,838,073 B1 * | 1/2005 | Collins et al. | 424/1.69 |
| 6,962,906 B2 | 11/2005 | Efimov et al. | |
| 7,141,233 B2 | 11/2006 | Collins et al. | |
| 7,179,445 B2 * | 2/2007 | Collins et al. | 424/1.69 |
| 2002/0002146 A1 | 1/2002 | Halevie-Goldman | |
| 2002/0042394 A1 | 4/2002 | Hogenkamp et al. | |
| 2002/0049155 A1 | 4/2002 | Hogenkamp | |
| 2002/0151525 A1 | 10/2002 | Collins et al. | |
| 2003/0018009 A1 | 1/2003 | Collins | |
| 2003/0144198 A1 | 7/2003 | Collins | |
| 2004/0162240 A1 | 8/2004 | Collins et al. | |
| 2005/0004010 A1 | 1/2005 | Collins et al. | |

FOREIGN PATENT DOCUMENTS

| | | |
|---|---|---|
| WO | 92/09610 | 6/1992 |
| WO | 92/13571 | 8/1992 |
| WO | 94/27613 | 12/1994 |
| WO | 94/27641 | 12/1994 |
| WO | 95/27723 | 10/1995 |
| WO | 96/04016 | 2/1996 |
| WO | 96/27641 | 9/1996 |
| WO | 96/31243 | 10/1996 |
| WO | 97/14711 | 4/1997 |
| WO | 97/18231 | 5/1997 |
| WO | 97/33627 | 9/1997 |
| WO | 98/08859 | 3/1998 |
| WO | 99/20643 | 4/1999 |
| WO | WO 99/29302 | 6/1999 |
| WO | 99/65529 | 12/1999 |
| WO | 99/65930 | 12/1999 |
| WO | 00/25793 | 5/2000 |
| WO | 00/45857 | 8/2000 |
| WO | 00/62808 | 10/2000 |
| WO | 00/74721 | 12/2000 |
| WO | WO 01/00646 | 1/2001 |
| WO | 01/17694 | 3/2001 |
| WO | 01/28592 | 4/2001 |
| WO | 01/28595 | 4/2001 |
| WO | 01/30967 | 5/2001 |
| WO | WO 01/53311 | 7/2001 |
| WO | 01/92283 | 12/2001 |
| WO | 01/92288 | 12/2001 |
| WO | 02/42318 | 5/2002 |
| WO | 02/055530 | 7/2002 |
| WO | 03/000010 | 1/2003 |
| WO | 03/025139 | 3/2003 |

OTHER PUBLICATIONS

Allen et al., Isolation of Gastric Vitamin B12-binding Proteins Using Affinity Chromatography, Journal of Biological Chemistry, 1973, 248(10):3660-3669.

Allen et al., "Isolation of Vitamin B12-binding Proteins Using Affinity Chromatography," *Journal of Biological Chemistry*, 1972, 247(23):7695-7701.

Allen, "Human Vitamin B12 Transport Proteins," *Progress in Hematology*, 1975, 9:57-84.

Amagasaki, et al., "Expression of Transcobalamin II Receptors by Human Leukemia K562 and HL-60 Cells," *Blood*, 1990, 76:1380-1386.

Anderson, et al., "Prepation, Biodistribution and Dosimetry of Copper-64-Labeled Anti-Colorectal Carcinoma Monoclonal Antibody Fragments 1A3-F(ab')$_2$," *J. Nuc. Med.*, 1995, 36:850-858.

Anton et al., "Carbon-13 Nuclear Magnetic Resonance Studies of the Monocarboxylic Acids of Cyanocobalamin. Assignments of the *b*-, *d*-, and *e*-Monocarboxylic Acids," *JACS*, 1980, 102(7):2215-2219.

Anton, et al., "The Synthesis and Properties of Four Spin-Labeled Analogs of Adenosylcobalamin," *J. Biol. Chem.*, 1980, 255:4507-4510.

Basu et al., "Synthesis and Characterization of a Peptide Nucleic Acid conjugated to a D-Peptide Analog of Insulin-like Growth Factor 1 for Increased Cellular Uptake," *Bioconj. Chem.*, 1997, 8:481-488.

Begley, et al., "Cobalamin Metabolism in Cultured Human Chorionic Villus Cells," *J. Cell. Physiol.*, 1993, 156:43-47.

Bernhauer et al., "Zur Chemie and Biochemie der Corrinoide," *Biochem. Z*, 1966, 344:289-309.

Blomquist, et al., "Uptake of Labelled Vitamin $B_{12}$ and 4-Iodophenylalanine in some Tumours of Mice," *Experientia*, 1969, 25:294-296.

Bouchaudon et al., "Daunomycin derivatives," *Chemical Abstracts*, 1969, 71(91866):440.

Breeman et al., "Radionuclide therapy using radiolabeled somatostatin analogs in tumor-bearing rats," *J. Nuc.Med.*, 40(5):102P, Abstract No. 413 (May 1999 supplement).

Broan et al. , "Synthesis and complexation behaviour of an effective octadentate complexone 1,4,7,10-tetraazacyclododecane-1,4,7,10-tetrakis[methylene(methylphosphinic acid)]," *J. Chem. Soc. Chem. Comm.*, 1990, 23:1739-1741.

Cannon et al., "Synthesis and Uptake of a Radiolabeled Cobalamin Bioconjugate," 9th International Symposium on Recent Advances in Drug Delivery Systems, Feb. 1999, pp. 230-231.

Chinnery et al., "Peptide nucleic acid delivery to human mitochondria," *Gene Therapy*, 1999, 6:1919-1928.

Coderre et al., "Boron Neutron Capture Therapy of a Murine Melanoma," *Cancer Research*, 1988, 48:6313-6316.

Collins et al., "Biodistribution of Radiolabeled Adenosylcobalamin in Patients Diagnosed With Various Malignancies," *Mayo Clin Proc.*, 2000, 75:568-580.

Collins et al., "Tumor Imaging Via Indium 111-Labeled DTPA-Adensylcobalamin," *Mayo Clin Proc.*, 1999, 74:687-691.

Collins et al., "Transcobalamin II receptor imaging via radiolabeled diethylene-triaminepentaacetate cobalamin analogs," *J. Nucl. Med.*, 1997, 38(5):717-723.

Collins et al., "Cobalamin Conjugates Useful as Imaging Agents and as Antitumor Agents," U.S. Appl. No. 09/690,198, filed Oct. 16, 2000.

Collins et al, "Transcobalamin Receptor Binding Conjugates for Neutron Capture Therapy," U.S. Appl. No. 10/028,857, filed Oct. 25, 2001.

Cooper, et al., "Selective Uptake of Specifically Bound Cobalt-58 Vitamin $B_{12}$ by Human and Mouse Tumour Cells" *Nature*, 1961, 191:393-395.

Cooperman, "Distribution of Radioactive and Nonradioactive Vitamin B12 in Normal and Malignant Tisues of an Infant with Neuroblastoma," *Cancer Research*, 1972, 32:167-172.

Cooperman, et al., "Distribution of Radioactive and Nonradioactive Vitamin B12 in the Dog," *J. Biol. Chem.*, 1960, 235:191-194.

Cuoto, "Management of Complications of Cancer Chemotherapy," "Chemotherapeutic Agents Commonly used in Veterinary Medicine," *Vet Clin North Am (Sm Anim)*, 1990; 20(4):1037-1053.

De Jong et al., "Radionuclide therapy using radiolabeled somatostatin analogs in tumor-bearing rats," *J. Nuc.Med.*, 40(5):102, Abstract No. 414 (May 1999 supplement).

Deprez-Decompaneere et al., "Comparison of the Activity of Daunorubicin and Two Derivatives on L1210 Leukemia In Vitro and In Vivo," *Current Chemotherapy: Proceedings of the 10th International Congress of Chemotherapy*, Zurich, Switzerland, Sep. 18-23, 1977, vol. II American Society for Microbiology, p. 1242-1244 (1978).

Ellenbogen, "Absorption and transport of cobalamin: Intrinsic factor and the transcobalamins," *Cobalamin: Biochemistry and Pathophysiology*, 1975, Chapter 5, Babior, Ed., Wiley, New York.

Fairchild et al., " Current status of 10-B-neutron capture therapy: enhancement of tumor dose via beam filtration and dose rate, and the effects of these parameters on minimum boron content: A theoretical evaluation," *Int. J. Radiation Oncology, Biology, Physics*, 1985, 11(4):831-840.

Fedosov et al., "Binding of Cobalamin and Cobinamide to Transcobalamin from Bovine Milk," Biochemistry, 1995, 34:16082-16087.

Fedosov et al., "Transcobalamin from cow milk: isolation and physico-chemical properties," *Biochimica et Biophysica Acta*, 1996, 1292:113-119.

Finkler et al., "Nature of the Relationship between Vitamin $B_{12}$ Binding and Cell Uptake," *Archives of Biochemistry and Biophysics*, 1967, 120:79-85.

Flodh, "Accumulation of Labeled Vitamin $B_{12}$ in Some Transplanted Tumours," *Int. J. Cancer*, 1968, 3(5): 694-699.

Gabel et al., "Monte Carlo simulation of the biological effect of the $^{10}B(n,\alpha)^7Li$ reaction in cells and tissue and its implication for boron neutron capture therapy," *Radiation Research*, 1987, 111:14-25.

Gabel, "Tumor-Seeking Compounds for Boron Neutron Capture Therapy: Synthesis and Biodistribution," *Clinical Aspects of Neutron Capture Therapy*, Ralph G. Fairchild et al., eds.; Plenum Press, New York, (undated), pp. 233-241.

Gennaro, "Components and Containers," *Remington: The Science and Practice of Pharmacy*, 1995, 19th Ed., vol. 2, Mack Publishing Co., pp. 1527-1529.

Ghose et al., "Antibody as Carrier of Chlorambucil," *Cancer*, 1972, 29:1398-1400.

Ghose et al., "Immunoradioactive Agent against Cancer," *Br. Med. J.*, 1967, 1:90-93.

Good and Nielsen, "Antisense inhibition of gene expression in bacteria by PNA targeted to mRNA," *Nature Biotechnol.*, 1998, 16: 355-358.

Guy et al., "Evaluation of coupling of cobalamin to antisense oligonucleotides by thin-layer and reversed-phase liquid chromatography," *J. Chromatog. B*, 1998, 709:149-156.

Hall et al., "Boron Betaine Analogs: Antitumor Activity and Effects on Ehrlich Ascites Tumor Cell Metabolism," *J. Pharm. Sci.*, 1979, 68(6):685-688.

Hall et al., "Cyclic Activity of the Receptors of Cobalamin Bound to Transcobalamin II," *Journal of Cellular Physiology*, 1987, 133(1):187-191.

Hatanaka et al., "Clinical Experience of Boron Neutron Capture Therapy for Gliomas—A Comparison with Conventional Chemo-Immuno-Radiotherapy," *Boron Neutron Capture Therapy for Tumors*, 1986, Chap. 25, pp. 349-379, Hatanaka (ed.), Niigata, Japan: Nishimura Co., Ltd.

Hatanaka, "A revised boron-neutron capture therapy for malignant brain tumors," *Journal of Neurology*, 1975, 209:81-94.

Hawthorne et al., "Preparation of tumor-specific boron compounds. 1. In vitro studies using boron-labeled antibodies and elemental boron as neutron targets," *Journal of Medicinal Chemistry*, 1992, 15(5):449-452.

HCAPLUS abstract 1996:676214 of ES 2 088 374, Aug. 1996, to De La Iglesia Ferreras.

Hogenkamp et al., Chemical synthesis and properties of analogs of adenosylcobalamin, *Biochemistry*, 1974, 13(13):2736-2740.

Hogenkamp et al., "Carbon-13 nuclear magnetic resonance studies of adenosylcobalamin and alkylcorrinoids, selectively enriched with carbon-13," *Biochemistry*, 1975, 14(16):3707-3714.

Hogenkamp et al., "Diagnostic and Therapeutic Analogues of Cobalamin," *Chemistry and Biochemistry of $B_{12}$*, Part II, Banerjee, ed., Wiley & Sons, Section 15:385-410.

Hogenkamp et al., "Synthesis and Characterization of *nido*-Carborane-Cobalamin Conjugates," *Nucl. Med. & Biol.*, 2000, 27:89-92.

Ichihashi et al., "Specific killing effect of $^{10}B_1$-para-boronophenylalanine in thermal neutron capture therapy of malignant melanoma: In vitro radiobiological evaluation," *The Journal of Investigative Dermatology*, 1982, 78(3):215-218.

Jacobsen et al., "Rapid purification of cobalamin-binding proteins using immobilized aminopropylcobalamin," *Anal. Biochem.*, 1981, 113:164-171.

Kahl and Micca, "Chemical and biological studies on boronated tetraphenyl porphyrins," *Boron Neutron Capture Therapy for Tumors*, 1986, Hatanaka (ed.), Niigata, Japan: Nishimura Co., Ltd., pp. 61-67.

Kahl et al., "New tumor localizers: Advances in the use of low density lipoproteins (LDL)," *Strahlenther. Onkol.*, 1989, 165(2/3):137-139.

Kaplan, et al., "Absorptions Studies of 59Fe and 58Co Vitamin B12 by Whole-Body Radiometry in the Radiation Therapy of Collum Carcinoma," *Radiobiol. Radiother.*, 1983, 24, Abstract, 745-752.

Kikugawa, et al., "Direct Halogenation of Sugar Moiety of Nucleosides," *Tetrahedron Letters*, 1971, 2:87-98.

Kollmer et al., "On a new radiopharmaceutical for kidney imaging," *Int. J. Applied Radiation and Isotopes*, 1974, 25(6):283-285.

Laster et al., "Biological efficacy of a boronated porphyrin as measured in cell culture," *Strahlentherapie and Onkologie*, 1989, 165(2/3):203-205.

Laster et al., "Dihydroxyboryldeoxyuridine (DBDU); Can a borated nucleoside deceive the DNA molecule," *Neutron Capture Therapy*, 1986, Niigata, Japan: Nishimura Co., Ltd., pp. 46-54.

Lindemans et al., "Uptake of transcobalamin II-Bound Cobalamin By HL-60 Cells: Effects Of Differentiation Induction," *Experimental Cell Research*, 1989, 184(2):449-460.

Luo, "Studies on bone tumor therapeutic radiopharmaceuticals.IV, Investigation of the structure-activity relationships (SARS) of $^{153}$Sm-aminocarboxylate complexes," *J. Nuc. Med.*, 40(5):316P, Abstract No. 1386 (May 1999 supplement).

McBride, "A general method for the introduction of metal binding ligands onto the side chains of peptides during peptide synthesis," in Scientific Papers (Jun. 9, 1999), Proc. of the 46th Annual Meeting of the Society of Nuclear Medicine (Los Angeles, California, Jun. 6-10, 1999), *J. Nuc. Med.*, 40(5):124P, Abstract No. 500 (May 1999 supplement).

McLean et al., "Antibodies to Transcobalamin II Block In Vitro Proliferation of Leukemic Cells," *Blood*, 1997, 89(1):235-242.

Mease et al., "Indium-111 CDTA-(aminostyryl)pyridiniumum (di-X-asp) dyes: synthesis, canine and human leukocyte labeling, and serum stability," in Poster Sessions, Proc. of the 46" Annual Meeting of the Society of Nuclear Medicine (Los Angeles, California, Jun. 6-10, 1999), *J. Nuc.Med.*, 40(5):318P, Abstract No. 1396 (May 1999 supplement).

Mishima et al., "First human clinical trial of melanoma neutron capture. Diagnosis and therapy," *Strahlentherapie and Onkologie*, 1989, 165(2/3):251-254.

Mishima et al., "Prerequisites of First Clinical Trial for Melanoma Selective Thermal Neutron Capture Therapy," *Neutron Capture Therapy*, 1986, Niigata, Japan: Nishimura Co., Ltd., pp. 230-236.

Mishima et al., "Treatment of malignant melanoma by single thermal neutron capture therapy with melanoma-seeking B-compound," *Lancet*, 1989, 2(8659):388-389.

Momen et al., "Impact of high resolution bone spect imaging of the thoracolumbar spine on patient management in oncology," in Scientific Papers (Jun. 9, 1999), Proc. of the 46th Annual Meeting of the Society of Nuclear Medicine (Los Angeles, California, Jun. 6-10, 1999), *J. Nuc. Med.*, 40(5):124P, Abstract No. 500 (May 1999 supplement).

Morita et al., "$2^1$-$O$,$4^1$-$C$-Ethylene-Bridged Nucleic Acids (ENA): Highly Nuclease-Resistant and Thermodynamically Stable Oligonucleotides for Antisense Drug," *Bioorgan. Med. Chem. Lett.*, 2002, 12:73-76.

Nakagawa et al., "Syntheses of chlorpromazine undecahydrododecaborate and nonahydrodecaborate—promising agents for neutron capture therapy of malignant melanoma," *Chem. Pharm. Bull.*, 1976, (Tokyo), 24(4):778-781.

Nexø, "Cobalamin Binding Proteins," *Vitamin B12 and B12 proteins*, eds. Krantler et al., Wiley & Sons, Ltd., pp. 461-475.

Norenberg, "[$^{213}$Bi-DOTA°,Tyr$^3$]octreotide ($^{213}$Bi-DOTATOC) in peptide receptor radionuclide therapy (PRRT)," *J. Nuc.Med.*, 40(5):103, Abstract No. 415 (May 1999 supplement).

Order et al., "Use of isotopic immunoglobulin in therapy," *Cancer Res.*, 1980, 40:3001-3007.

Pardridge et al., "Vector-mediated delivery of polyamide ("peptide") nucleic acid analogue through the blood-brain barrier in vivo," *Proc. Natl. Acad. Sci. USA*, 1995, 92:5592-5596.

Pathare et al., "Synthesis of cobalamin-biotin conjugates that vary in the position of cobalamin coupling. Evaluation of cobalamin derivative binding to transcobalamin II," *Bioconjugate Chem.*, 1996, 7(2):217-232.

Pinson et al., "Synthesis of Two Doxorubicin-Cobalamin Bioconjugates," 9th International Symposium on Recent Advances in Drug Delivery Systems, Feb. 1999, pp. 228-229.

Pinson et al., "Synthesis, protein binding, and cellular uptake of doxorubicin—cobalamin bioconjugates," *American Chemical Society—Abstracts of Paper*, 2000, vol. 219, Nos. 1-2, Abstract.

Pisal et al., "Pluronic gels for nasal delivery of vitamin $B_{12}$. Part I: Preformulation study," *International Journal of Pharmacentics*, 270(1-2): 37-45 (2003).

Ponto, "II. Schilling Test," In: *Pharmaceuticals in Medical Imaging*, 1990, Swanson et al, (eds.), Macmillan Publishing Co., Inc., New York, pp. 621-628.

Pooga et al., "Cell penetrating PNA constructs regulate galanin receptor levels and modify pain transmission in vivo," *Nat. Biotechnol.*, 1998, 16:857-861.

Prakash et al., "Synthesis of $2^1$-$O$-[2-[($N$,$N$-Dimethylamino) oxy]ethyl] Modified Nucleosides and Oligonucleotides," *J. Org. Chem.*, 2002, 67:357-369.

Primus, "Bispecific antibody mediated targeting of *nido*-carboranes to human colon carcinoma cells," *Bioconjugate Chemistry*, 1996, 7:532-535.

'Chemotherapy Drugs to Know—MCMP 611' [online]. Purdue University School of Veterinary Medicine, 1997, [retrieved on Nov. 14, 2000]. Retrieved from the Internet: <URL: http://www.vet.purdue.edu/bms/courses/mcmp611/chmrx/drg2no61.htm>, 9 pages.

Rappazzo et al., "Transport Function of Transcobalamin II," *Journal of Clinical Investigation*, 1972, 51:1915-1918.

Roe et al., "Combinatorially designed technetium radiopharmaceuticals (CDTR™)," in Scientific Papers, Proc. of the 46th Annual Meeting of the Society of Nuclear Medicine (Los Angeles, California, Jun. 6-10, 1999), *J. Nuc. Med.*, 40(5):123P, Abstract No. 499 (May 1999 supplement).

Ruser et al., "Synthesis and evaluation of two new bifunctional carboxymethylated tetraazamacrocyclic chelating agents for protein labeling with indium-111," *Bioconjugate Chem.*, 1990, 1:345-349.

Russell-Jones et al., "Vitamin $B_{12}$ mediated oral delivery systems for granulocyte-colony stimulating factor and erythropoietin," *Bioconjugate Chem.*, 1995, 6(4):459-465.

Sattelberger et al., "Nuclear medicine finds the right chemistry," *Nature Biotechnology*, 1999, 17:849-850.

Scarfi et al., "Synthesis, Uptake, and Intracellular Metabolism of a Hydrophobic Tetrapeptide-Peptide Nucleic Acid (PNA)-Biotin Molecule," *Biochem. Biophys. Res. Commun.*, 1997, 236:323-326.

Schinazi et. al., "Synthesis and Properties of Boron and Silicon Substituted Uracil of 2'-Deoxyuridine," *Tetrahedron Letters*, 1978, 50:4981-4984.

Scott, "Bioavailability of vitamin B12," *Eur. J. Clinical Nutrition*, 1997, 51(Suppl. I):S49-S53.

Simmons et al., "Synthesis and membrane Permeability of PNA-Peptide Conjugates," *Bioorgan. Med. Chem. Lett.*, 1997, 7(23):3001-3006.

Smeltzer et al., "Cytotoxicities of Two Cobalamin Bioconjugates," 9th International Symposium on Recent Advances in Drug Delivery Systems, Feb. 1999, pp. 232-233.

Smeltzer et al., "Synthesis and Characterization of Fluorescent Cobalamin (CobalaFluor) Derivatives for Imaging," *Organic Letters*, 2001, 3(6):799-801.

Sneath et al., "Protein-Binding Polyhedral Boranes," *J. Medicinal Chem.*, 1976, 19(11):1290-1294.

Soda et al., "Receptor Distribution and the Endothelial Uptake of Transcobalamin II in Liver Cell Suspensions," *Blood*, 1985, 65(4):795-802.

Takakura and Hashida, "Macromolecular drug carrier systems in cancer chemotherapy: macromolecular prodrugs," *Critical Reviews in Oncology: Hematology*, 195, 18: 207-231.

*The Merck Index An Encyclopedia of Chemicals, Drugs, And Biologicals*, 1996, Twelfth Edition Budavari et al., Eds., p. 1710.

Toraya et al., "Preparation, properties and biological activities of succinyl derivatives of vitamin$B_{12}$,", *Bioinorg. Chem.*, 1975, 4:245-255.

Uchino et al., "Tissue Distribution of Coenzyme B12 in Rats Following Intravenous Administration," *Annals of the New York Academy of Sciences*, 1964, 112(Art. 2):844-854.

Vares, et al., "Kinetic of $^{57}$Co-Cyanocobalamin Distribution in Organs and Tissues of Mice with Transplanted Tumours," *Eksp. Onkol.*, 1986, 8:33-36, Abstract.

Wahlestedt et al., "Potent and nontoxic antisense oligonucleotides containing locked nucleic acids," *Proc. Natl. Acad. Sci. USA*, 2000, 97(10):5633-5638.

Walker et al., "The chemical synthesis and nuclear magnetic resonance spectroscopy of adenosylcobalamin selectively enriched with carbon-13," *Biochemistry*, 1974, 13(12):2650-2655.

Whittacker, "Biosynthesis of a Thiouracil Pheomelanin in Embryonic Pigment Cells Exposed to Thiouracil," *J. Biol. Chem.*, 1971, 246(20):6217-6226.

Wilbur et al., "Biotin Reagents for Antibody Pretargeting. 4. Selection of Biotin Conjugates for in Vivo Application Based on Their Dissociation Rate from Avidin and Streptavidin" *Bioconjugate Chem.*, 2000, 11(4):569-583.

Wilbur et al., "Evaluation of Biotin-Dye Conjugates for Use in an HPLC Assay to Assess Relative Binding of Biotin Derivatives with Avidin and Streptavidin," *Bioconjugate Chem.*, 2000, 11(4):584-598.

Woolley, et al., "Uptake of [CO-57]-Vitamin B-12 By Murine Tumours of Many Histologic Types," *Clinical Research*, 1993, Abstracts of National Meeting, Association of American Physicians, p. 73A.

Wu, et al., "Investigations of N-linked Macrocycles for $^{111}$In and $^{90}$Y Labeling of Proteins," *Nucl. Med. Biol.*, 1992, 19:239-244.

Wunderbaldinger et al., "New approaches for imaging in gene therapy," *Eur. J. Radiology*, 2002, 34: 156-165.

Yong et al., "In vitro and in vivo evaluation of a-corboranylalanine as a potential boran delivery agent for neutron capture therapy," *Anti-cancer Research*, 1995, 15:2033-2038.

U.S. Appl. No. 09/690,198, filed Oct. 16, 2000.

U.S. Appl. No. 10/028,857, filed Oct. 25, 2001.

U.S. Appl. No. 60/129,733, filed Apr. 16, 1999.

U.S. Appl. No. 60/159,753, filed Oct. 15, 1999.

U.S. Appl. No. 60/159,873, filed Oct. 15, 1999.

U.S. Appl. No. 60/159,874, filed Oct. 15, 1999.

Akine et al., "Neutron-capture therapy of murine ascites tumor with gadolinium-containing microcapsules," *J. Cancer Res. Clin. Oncol.*, 1992, 119:71-73.

Alvarez et al., "On a New Radiopharmaceutical for Kidney Imaging," *Int. J. Appl. Radiation and Isotopes*, 1974, 25(6):283-284.

Armitage et al., "Chemistry of the Vitamin $B_{12}$ Group. Part III. The Course of Hydrolytic Degradations," *J. Chem. Soc.*, 1953, 3849-3864.

Chaiet et al., "Biosynthesis of Radioactive Vitamin $B_{12}$ Containing Cobalt$^{60}$," *Science*, 1950, 3:601-602.

CTEP [Developing Cancer Therapies], "FDA Approved Anti-Cancer Drugs" Jan. 1, 1997 at http://ctep.info.nih.gov/handbook/HandBookText/fda_agen.htm, accessed Nov. 14, 2000.

"Current Status of Neutron Capture Therapy," *International Atomic Energy Agency*, May 2001.

Flodh, "Accumulation of Labeled Vitamin $B_{12}$ in Some Transplanted Tumours," *Distribution and Kinetics of Labeled Vitamin B12, Acta Radiologica*, 1968, Supplementum 284, pp. 55-60.

Gennaro, *Remington: The Science and Practice of Pharmacy*, 1995, 19th ed., vol. 2, Mack Publishing Co., pp. 1527-1529, 1561.

Gottlieb et al., "Rapid Charcoal Assay for Intrinsic Factor (IF), Gastric Juice Unsaturated $B_{12}$ Binding Capacity, Antibody to IF, and Serum Unsaturated $B_{12}$ Binding Capacity," *Blood*, 1965, 25(6):875-883.

Grossowicz et al., "Isotopic Determination of Vitamin B12 Binding Capacity and Concentration," *Proc. Soc. Exp. Biol. Med.*, 1962, 109:604-608.

Higashi et al., "In Vitro Assessment of 2-Fluoro-2-Deoxy-D-Glucose, L-Methionine and Thymidine as Agents to Monitor the Early Response of a Human Adenocarcinoma Cell Line to Radiotherapy," *J. Nucl. Med.*, 1993, 34:773-779.

Knudsen and Nielsen, "Application of peptide nucleic acid in cancer therapy," *Anti-Cancer Drug*, 1997, 8:113-118.

Kubota et al., "Tracer Feasibility for Monitoring Tumor Radiotherapy: A Quadruple Tracer Study with Fluorine-18-Fluorodeoxyglucose or Fluorine-18-Fluorodeoxyuridine, L-[Methyl-$^{14}$C]Methionine, [6-$^{3}$H]Thymidine, and Gallium-67," *J. Nucl. Med.*, 1991, 32(11):2118-2123.

Larrea et al., "Tumor necrosis factor alpha gene expression and the response to interferon in chronic hapatitis C," *Hepatology*, 1996, 23:210-217.

Masiakowski et al., "Gadolinium neutron capture therapy for brain tumors: A computer study," *Med. Phys.*, 1992, 19(5):1277-1284.

Nielsen et al., "Sequence-Selective Recognition of DNA by Strand Displacement with a Thymine-Substituted Polyamide," *Science*, 1991, 254:1497-1500.

Pisal et al., "Pluronic gels for delivery of Vitamin $B_{12}$. Part I: Preformulation study," *Int. J. Pharm.*, 2004, 270:37-45.

Rao et al., "TC-99M labeled peptide for imaging infection," *Proc. of the 46th Annual Meeting of the Society of Nuclear Medicine* Los Angeles, California, Jun. 6-10, 1999, Abstract No. 1398.

Ruiz et al., "Influence of Average Molecular Weights of Poly($_{DL}$-Lactic Acid-Co-Glycolic Acid) Copolymers 50/50 on Phase Separation and in Vitro Drug Release from Microspheres," *Pharm. Res.*, 1990, 7(9):928-934.

Shih and Brugger, "Gadolinium as a neutron capture therapy agent," *Med. Phys.*, 1992, 19:733-744.

Svanvik et al., "Light-Up Probes: Thiazole Orange-Conjugated Peptide Nucleic Acid for Detection of Target Nucleic Acid in Homogeneous Solution," *Analyt. Biochem.*, 2000, 281:26-35.

The Merck Index An Encyclopedia of Chemicals, Drugs, And Biologicals, 1989, Eleventh Edition Budavari et al. (eds.), p. 1577.

The Merck Index An Encyclopedia of Chemicals, Drugs, And Biologicals, 1996, Twelfth Edition Budavari et al. (eds.), p. 1710.

van Eijkeren et al., "Measurement of Short-Term $^{11}$C-Thymidine Activity in Human Head and Neck Tumours Using Positron Emission Tomography (PET)," *Acta Oncologica*, 1992, 31(5):539-543.

Wierzbicki et al., "Measurement of augmentation of $^{252}$Cf implant by $^{10}$B and $^{157}$Gd neutron capture," *Med. Phys.*, 1994, 21(6):787-790.

Yamada and Hogenkamp, "The Synthesis of a 5'-Deoxyadenosylcobalamin-agarose Adsorbent and Its Utility in the Purification of Ribonucleotide Reductase," *J. Biol. Chem.*, 1972, 247:6266-6270.

\* cited by examiner

Synthesis of adenosyltrifluoromethylamidocobalamins

CNCbl COOH (b, d, and e)

↓ WSC
Hydroxybenzotriazole          (1, 2, and 3)
F₃CCH₂N⁺H₃Cl⁻

(4, 5, and 6)

↓ NaBH₄
5'-CHLORO-5'-DEOXYADENOSINE (8 and 9)

Synthesis of adenosyltrifluoroethylamidocobalamins

Synthesis of cyano-b-trifluoroacetamidobutylamidocobalamin

Synthesis of cyanotrifluoroacetyl polylysine cobalamin

FIG. 6

TRANSCOBALAMIN RECEPTOR BINDING CONJUGATES USEFUL FOR TREATING ABNORMAL CELLULAR PROLIFERATION

This application is a continuation of U.S. application Ser. No. 10/027,593, filed Oct. 25, 2001, now abandoned, which claims priority to U.S. provisional application No. 60/243,082 and U.S. provisional application No. 60/243,112, both filed on Oct. 25, 2000.

FIELD OF THE INVENTION

The present invention includes compounds, compositions and methods for the treatment, prophylaxis and/or diagnosis of abnormal cellular proliferation.

BACKGROUND OF THE INVENTION

Cellular differentiation, growth, function and death are regulated by a complex network of mechanisms at the molecular level in a multicellular organism. In the healthy animal or human, these mechanisms allow the cell to carry out its designed function and then die at a programmed rate.

Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. In normal skin the time required for a cell to move from the basal layer to the upper granular layer is about five weeks. In psoriasis, this time is only 6 to 9 days, partially due to an increase in the number of proliferating cells and an increase in the proportion of cells which are dividing (G. Grove, Int. J. Dermatol. 18:111, 1979). Approximately 2% of the population the United States have psoriasis, occurring in about 3% of Caucasian Americans, in about 1% of African Americans, and rarely in native Americans. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. The advanced lesions of atherosclerosis result from an excessive inflammatory-proliferative response to an insult to the endothelium and smooth muscle of the artery wall (Ross R., Nature 362:801-809 (1993)). Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic microangiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells (See, e.g., Harris, E. D., Jr., The New England Journal of Medicine, 322: 1277-1289 (1990)), and to be caused by autoantibodies produced against collagen and IgE.

Other disorders that can include an abnormal cellular proliferative component include Behcet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

A tumor, also called a neoplasm, is a new growth of tissue in which the multiplication of cells is uncontrolled and progressive. A benign tumor is one that lacks the properties of invasion and metastasis and is usually surrounded by a fibrous capsule. A malignant tumor (i.e., cancer) is one that is capable of both invasion and metastasis. Malignant tumors also show a greater degree of anaplasia (i.e., loss of differentiation of cells and of their orientation to one another and to their axial framework) than benign tumors.

Approximately 1.2 million Americans are diagnosed with cancer each year, 8,000 of which are children. In addition, 500,000 Americans die from cancer each year in the United States alone. Prostate and lung cancers are the leading causes of death in men while breast and lung cancer are the leading causes of death in women. It is estimated that cancer-related costs account for about 10 percent of the total amount spent on disease treatment in the United States.

Proliferative disorders are currently treated by a variety of classes of compounds including alkylating agents, antimetabolites, natural products, enzymes, biological response modifiers, miscellaneous agents, hormones and antagonists, such as those listed below.

Alkylating Agents

Nitrogen Mustards: Mechlorethamine (Hodgkin's disease, non-Hodgkin's lymphomas), Cyclophosphamide Ifosfamide (acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas), Melphalan (L-sarcolysin) (multiple myeloma, breast, ovary), Chlorambucil (chronic lymphoctic leukemia, primary macroglobulinemia, Hodgkin's disease, non-Hodgkin's lymphomas).

Ethylenimines and Methylmelamines: Hexamethylmelamine (ovary), Thiotepa (bladder, breast, ovary).

Alkyl Sulfonates: Busulfan (chronic granuloytic leukemia).

Nitrosoureas: Carmustine (BCNU) (Hodgkin's disease, non-Hodgkin's lymphomas, primary brain tumors, multiple myeloma, malignant melanoma), Lomustine (CCNU) (Hodgkin's disease, non-Hodgkin's lymphomas, primary brain tumors, small-cell lung), Semustine (methyl-CCNU) (primary brain tumors, stomach, colon), Streptozocin (streptozocin) (malignant pancreatic insulinoma, malignant carcinoin).

Triazenes: Dacarbazine (DTIC; dimethyltriazenoimidazolecarboxamide) (malignant melanoma, Hodgkin's disease, soft-tissue sarcomas).

Antimetabolites

Folic Acid Analogs: Methotrexate(amethopterin) (acute lymphocytic leukemia, choriocarcinoma, mycosis fungoides, breast, head and neck, lung, osteogenic sarcoma).

Pyrimidine Analogs: Fluorouracil (5-fluorouracil; 5-FU) Floxuridine (fluorodeoxyuridine; FUdR) (breast, colon, stomach, pancreas, ovary, head and neck, urinary bladder, premalignant skin lesions) (topical), Cytarabine(cytosine arabinoside) (acute granulocytic and acute lymphocytic leukemias).

Purine Analogs and Related Inhibitors: Mercaptopurine (6-mercaptopurine; 6-MP) (acute lymphocytic, acute granulocytic and chronic granulocytic leukemia), Thioguanine (6-thioguanine: TG) (acute granulocytic, acute lymphocytic and chronic granulocytic leukemia), Pentostatin (2'-deoxycyoformycin) (hairy cell leukemia, mycosis fungoides, chronic lymphocytic leukemia).

Vinca Alkaloids: Vinblastine (VLB) (Hodgkin's disease, non-Hodgkin's lymphomas, breast, testis), Vincristine (acute lymphocytic leukemia, neuroblastoma, Wilms' tumor, rhabdomyosarcoma, Hodgkin's disease, non-Hodgkin's lymphomas, small-cell lung).

Epipodophyl-lotoxins: Etoposide (testis, small-cell lung and other lung, breast, Hodgkin's disease, non-Hodgkin's lymphomas, acute granulocytic leukemia, Kaposi's sarcoma), Teniposide (testis, small-cell lung and other lung, breast, Hodgkin's disease, non-Hodgkin's lymphomas, acute granulocytic leukemia, Kaposi's sarcoma).

Natural Products

Antibiotics: Dactinomycin (actinonmycin D) (choriocarcinoma, Wilms' tumor rhabdomyosarcoma, testis, Kaposi's sarcoma), Daunorubicin (daunomycin; rubidomycin) (acute granulocytic and acute lymphocytic leukemias), Doxorubicin (soft tissue, osteogenic, and other sarcomas; Hodgkin's disease, non-Hodgkin's lymphomas, acute leukemias, breast, genitourinary thyroid, lung, stomach, neuroblastoma), Bleomycin (testis, head and neck, skin and esophagus lung, and genitourinary tract, Hodgkin's disease, non-Hodgkin's lymphomas), Plicamycin (mithramycin) (testis, malignant hypercalcema), Mitomycin (mitomycin C) (stomach, cervix, colon, breast, pancreas, bladder, head and neck).

Enzymes: L-Asparaginase (acute lymphocytic leukemia).

Biological Response Modifiers: Interferon-alfa (hairy cell leukemia, Kaposi's sarcoma, melanoma, carcinoid, renal cell, ovary, bladder, non Hodgkin's lymphomas, mycosis fungoides, multiple myeloma, chronic granulocytic leukemia).

Hormones and Antagonists

Estrogens: Diethylstibestrol Ethinyl estradiol (breast, prostate)

Antiestrogen: Tamoxifen (breast).

Androgens: Testosterone propionate Fluxomyesterone (breast).

Antiandrogen: Flutamide (prostate).

Gonadotropin-Releasing Hormone Analog: Leuprolide (prostate).

Miscellaneous Agents

Platinum Coordination Complexes: Cisplatin (cis-DDP) Carboplatin (testis, ovary, bladder, head and neck, lung, thyroid, cervix, endometrium, neuroblastoma, osteogenic sarcoma).

Anthracenedione: Mixtozantrone (acute granulocytic leukemia, breast).

Substituted Urea: Hydroxyurea (chronic granulocytic leukemia, polycythemia vera, essential thrombocytosis, malignant melanoma).

Methylhydrazine Derivative: Procarbazine (N-methylhydrazine, MIH) (Hodgkin's disease).

Adrenocortical Suppressant: Miotane (o,p'-DDD) (adrenal cortex), Aminoglutethimide (breast).

Adrenorticosteriods: Prednisone (acute and chronic lymphocytic leukemias, non-Hodgkin's lymphomas, Hodgkin's disease, breast).

Progestins: Hydroxprogesterone caproate, Medroxyprogersterone acetate, Megestrol acetate (endometrium, breast).

Toxicity associated with therapy for abnormally proliferating cells, including cancer, is due in part to a lack of selectivity of the drug for diseased versus normal cells. To overcome this limitation, therapeutic strategies that increase the specificity and thus reduce the toxicity of drugs for the treatment of proliferative disorders are being explored. One such strategy that is being aggressively pursued is drug targeting.

An objective of treatment and/or image targeting is to deliver a therapeutic and/or diagnostic agent to a specific site of action through a carrier system. Targeting achieves at least two major aims of drug delivery. The first is to deliver the maximum dose of therapeutic agent to diseased cells. The second is the avoidance of uptake by normal, healthy cells. Thus, targeted drug delivery systems result in enhancing drug accumulation in the proliferative cells while decreasing exposure to healthy tissues. As such, the efficacy is increased while the toxicity is decreased, giving a better therapeutic index.

Two classes of compounds that are known to localize in malignant tumors are the porphyrins and the related phthalocyanines. The biochemical basis by which these compounds achieve elevated concentration in malignant tumors is unknown, but this observation has served as the rationale for the use of hematoporphyrin derivatives in the photodyamic therapy of cancer (Dougherty, T. J. et al., *Porphyrin Photosensitization*, 3-13, New York: Plenum Publishing Corp. (1981)).

Cells undergoing rapid proliferation have been shown to increase uptake of thymidine and methionine. (See, for example, M. E. van Eijkeren et al., *Acta Oncologica*, 31, 539 (1992); K. Kobota et al., *J. Nucl. Med.*, 32, 2118 (1991) and K. Higashi et al., *J. Nucl. Med.*, 34, 773 (1993)). Since methylcobalamin is directly involved with methionine synthesis and indirectly involved in the synthesis of thymidylate and DNA, methyl-cobalamin as well as Cobalt-57-cyanocobalamin have also been shown to have increased uptake in rapidly dividing tissue (for example, see, B. A. Cooper et al., *Nature*, 191, 393 (1961); H. Flodh, *Acta Radiol. Suppl.*, 284, 55 (1968); L. Bloomquist et al., *Experientia*, 25, 294 (1969)). Additionally, upregulation in the number of transcobalamin II receptors has been demonstrated in several malignant cell lines during their accelerated thymidine incorporation and DNA synthesis. See, J. Lindemans et al., *Exp. Cell. Res.*, 184, 449 (1989); T. Amagasaki et al., *Blood*, 26, 138 (1990) and J. A. Begly et al., *J. Cell Physiol.*, 156, 43 (1993). Bacteria naturally insert Cobalt-59 into the corrin ring of vitamin $B_{12}$. Commercially this has been exploited by the fermentative production of Co-56, Co-57, Co-58, and Co-60 radiolabeled vitamin $B_{12}$. For example, see Chaiet et al., *Science*, 111, 601 (1950). Unfortunately Cobalt-57, with a half life of 270.9 days, makes Co-57-cyanocobalamin unsuitable for clinical tumor imaging. Other metal ions (cobalt, copper and zinc) have been chemically inserted into naturally occurring descobaltocorrinoids produced by *Chromatium* and *Streptomyces olivaceous*. Attempts to chemically insert other metal ions in these cobalt free corrinoid rings have been unsuccessful. The placement of metals (cobalt, nickel, palladium, platinum, rhodium, zinc, and lithium) into a synthetic corrin ring has not presented any major difficulties. However, their instability and cost to produce makes them impractical for biological assays. Although Co-59 has a weakly paramagnetic quadrapolar nucleus in the $2^+$ oxidation state, Co-59 exists in the $3^+$ oxidation state within the corrin ring of vitamin $B_{12}$ and is diamagnetic. Therefore, insertion of either a radioactive or paramagnetic metal ion other than cobalt into the corrin ring does not seem feasible at this time.

The structure of various forms of vitamin $B_{12}$ is shown in FIG. 1, wherein X is CN, OH, $CH_3$ or 5'-deoxyadenosyl, respectively. The term cobalamin is sometimes used to refer to the entire molecule except the X group. The fundamental ring system without cobalt (Co) or side chains is called corrin and the octadehydrocorrin is called corrole. FIG. 1 is adapted from *The Merck Index*, Merck & Co. (11th ed. 1989), wherein X is above the plane defined by the corrin ring and the nucleotide is below the plane of the ring. The corrin ring has attached seven amidoalkyl ($H_2NC(O)Alk$) substituents, at the 2, 3, 7, 8, 13, 18 and 23 positions, which can be designated a-g respectively. See D. L. Anton et al., *J. Amer. Chem. Soc.*, 102, 2215 (1980). The 2, 3, 7, 8 and 13 positions are shown in FIG. 1 as positions a-e, respectively.

For several years after the isolation of vitamin $B_{12}$ as cyanocobalamin in 1948, it was assumed that cyanocobalamin and possibly hydroxocobalamin, its photolytic breakdown product, occurred in man. Since then it has been recognized that cyanocobalamin is an artifact of the isolation of vitamin $B_{12}$ and that hydroxocobalamin and the two coenzyme forms, methylcobalamin and adenosylcobalamin, are the naturally occurring forms of the vitamin.

Vitamin $B_{12}$ (adenosyl-, cyano-, hydroxo- or methylcobalamin) must be bound by the transport protein Transcobalamin I, II, or III ("TC") to be biologically active, and by Intrinsic Factor ("IF") if administered orally. Gastrointestinal absorption of vitamin $B_{12}$ occurs when the intrinsic factor-vitamin $B_{12}$ complex is bound to the intrinsic factor receptor in the terminal ileum. Likewise, intravascular transport and subsequent cellular uptake of vitamin $B_{12}$ throughout the body typically occurs through the transcobalamin transport protein (I, II or III) and the cell membrane transcobalamin receptors, respectively. After the transcobalamin vitamin $B_{12}$ complex has been internalized in the cell, the transport protein undergoes lysozymal degradation, which releases vitamin $B_{12}$ into the cytoplasm. All forms of vitamin $B_{12}$ can then be interconverted into adenosyl-, hydroxo- or methylcobalamin depending upon cellular demand. See, for example, A. E. Finkler et al., *Arch. Biochem. Biophys.*, 120, 79 (1967); C. Hall et al., *J. Cell Physiol.*, 133, 187 (1987); M. E. Rappazzo et al., *J. Clin. Invest.*, 51, 1915 (1972) and R. Soda et al., *Blood*, 65, 795 (1985).

A process for preparing $^{125}$I-vitamin $B_{12}$ derivatives is described in Niswender et al. (U.S. Pat. No. 3,981,863). In this process, vitamin $B_{12}$ is first subjected to mild hydrolysis to form a mixture of monocarboxylic acids, which Houts, infra, disclosed to contain mostly the (e)-isomer. The mixture is then reacted with a p-(aminoalkyl)phenol to introduce a phenol group into the $B_{12}$ acids (via reaction with one of the free carboxylic acid groups). The mixed substituent $B_{12}$ derivatives are then iodinated in the phenol-group substituent. This U.S. patent teaches that the mixed $^{125}$I-$B_{12}$ derivatives so made are useful in the radioimmunoassay of $B_{12}$, using antibodies raised against the mixture.

T. M. Houts (U.S. Pat. No. 4,465,775) reported that the components of the radiolabeled mixture of Niswender et al. did not bind with equal affinity to IF. Houts disclosed that radioiodinated derivatives of the pure monocarboxylic (d)-isomer are useful in assays of $B_{12}$ in which IF is used.

U.S. Pat. Nos. 5,739,313; 6,004,533; 6,096,290 and PCT Publication WO 97/18231 listing Collins and Hogenkamp as inventors disclose radionuclide labeling of vitamin $B_{12}$ through the propionamide moieties on naturally occurring vitamin $B_{12}$. The inventors converted the propionamide moieties at the b-, d-, and e-positions of the corrole ring to monocarboxylic acids, through a mild hydrolysis, and separated the carboxylic acids by column chromatography. The inventors then attached a bifunctional linking moiety to the carboxylate function through an amide linkage, and a chelating agent to the linking moiety again through an amide linkage. The chelating moiety was then used to attach a radionuclide to the vitamin that can be used for therapeutic and/or diagnostic purposes. See also PCT Publications WO 00/62808; WO 01/28595 and WO 01/28592.

PCT Publication WO 98/08859 listing Grissom et al as inventors discloses conjugates containing a bioactive agent and an organocobalt complex in which the bioactive agent is covalently bound directly or indirectly, via a spacer, to the cobalt atom. The organocobalt complex can be cobalamin and the bioactive agent can be a chemotherapeutic agent. However, only one bioactive agent (i.e., chemotherapeutic agent) is attached to the organocobalt complex (i.e., cobalamin) and the attachment is solely through the cobalt atom (i.e., the 6-position of cobalamin). The bioactive agent is released from the bioconjugate by the cleavage of the weak covalent bond between the bioactive agent and the cobalt atom as a result of normal displacement by cellular nucleophiles or enzymatic action, or by application of an external signal (e.g., light, photoexcitation, ultrasound, or the presence of a magnetic field).

U.S. Pat. Nos. 5,428,023; 5,589,463 and 5,807,823 to Russell-Jones et al. discloses a vitamin $B_{12}$ conjugate for delivering oral hormone formulations. Russell-Jones teaches that the vitamin $B_{12}$ conjugate must be capable of binding in vivo to intrinsic factor, enabling uptake and transport of the complex from the intestinal lumen of a vertebrate host to the systemic circulation of the host. The hormones are attached to the vitamin $B_{12}$ through a hydrolyzed propionamide linkage on the vitamin. The patent states that the method is useful for orally administering hormones, bioactive peptides, therapeutic agents, antigens, and haptens, and lists as therapeutic agents neomycin, salbutamol cloridine, pyrimethamine, penicillin G, methicillin, carbenicillin, pethidine, xylazine, ketamine hydrochloride, mephanesin and iron dextran. U.S. Pat. No. 5,548,064 to Russell-Jones et al. discloses a vitamin $B_{12}$ conjugate for delivering erythropoietin and granulocyte-colony stimulating factor, using the same approach as the '023 patent.

U.S. Pat. No. 5,449,720 to Russell-Jones et al discloses vitamin $B_{12}$ linked through a polymer to various active agents wherein the conjugate is capable of binding to intrinsic factor for systemic delivery. In particular, the document discloses the attachment of various polymeric linkers to the propionamide positions of the vitamin $B_{12}$ molecule, and the attachment of various bioactive agents to the polymeric linker. Exemplary bioactive agents include hormones, bioactive peptides and polypeptides, antitumor agents, antibiotics, antipyretics, analgesics, antiinflammatories, and haemostatic agents. Exemplary polymers include carbohydrates and branched chain amino acid polymers. The linkers used in '720 are polymeric. Importantly, the linkers are described as exhibiting a mixture of molecular weights, due to the polymerization process by which they are made. See in particular, page 11, lines 25-26 wherein it is stated that the polymer used in that invention is of uncertain size and/or structure.

PCT Publication WO 99/65930 to Russell-Jones et al. discloses the attachment of various agents to the 5'-OH position on the vitamin $B_{12}$ ribose ring. The publication indicates that the system can be used to attach polymers, nanoparticles, therapeutic agents, proteins and peptides to the vitamin. See also, U.S. Pat. No. 6,262,253 "Vitamin $B_{12}$ conjugates with GCSF, analogues thereof and pharmaceutical compositions;" U.S. Pat. No. 6,221,397 "Surface cross-linked particles suitable for controlled delivery;" U.S. Pat. No. 6,159,502 "Oral delivery systems for microparticles;" U.S. Pat. No. 6,150,341 "Vitamin $B_{12}$ derivatives and methods for their preparation;" U.S. Pat. No. 5,869,466 "Vitamin $B_{12}$ mediated oral delivery systems for GCSF;" and U.S. Pat. No. 5,548,064 "Vitamin $B_{12}$ conjugates with EPO, analogues thereof and pharmaceutical compositions."

U.S. Pat. No. 5,574,018 to Habberfield et al. discloses conjugates of vitamin $B_{12}$ in which a therapeutically useful protein is attached to the primary hydroxyl site of the ribose moiety. The patent lists erythropoietin, granulocyte-colony stimulating factor and human intrinsic factor as therapeutically useful proteins, and indicates that the conjugates are particularly well adapted for oral administration.

U.S. Pat. No. 5,840,880 to Morgan, Jr. et al. discloses vitamin $B_{12}$ conjugates to which are linked receptor modulating agents, which affect receptor trafficking pathways that govern the cellular uptake and metabolism of vitamin $B_{12}$. The receptor modulating agents are linked to the vitamin at the b-, d-, or e-position.

Other patent filings which describe uses of Vitamin $B_{12}$ include U.S. Pat. No. 3,936,440 to Nath (Method of Labeling Complex Metal Chelates with Radioactive Metal Isotopes); U.S. Pat. No. 4,209,614 to Bernstein et al., (Vitamin $B_{12}$ Derivatives Suitable for Radiolabeling); U.S. Pat. No. 4,279,859 (Simultaneous Radioassay of Folate and Vitamin $B_{12}$); U.S. Pat. No. 4,283,342 to Yollees (Anticancer Agents and Methods of Manufacture); U.S. Pat. No. 4,301,140 to Frank et al (Radiopharmaceutical Method for Monitoring Kidneys); U.S. Pat. No. 4,465,775 to Houts (Vitamin $B_{12}$ and labeled Derivatives for Such Assay); U.S. Pat. No. 5,308,606 to Wilson et al (Method of Treating and/or Diagnosing Soft Tissue Tumors); U.S. Pat. No. 5,405,839 (Vitamin $B_{12}$ Derivative, Preparation Process Thereof, and Use Thereof); U.S. Pat. No. 5,449,720 to Russell-Jones et al., (Amplification of the Vitamin $B_{12}$ Uptake System Using Polymers); U.S. Pat. No. 5,589,463 to Russell Jones (Oral Delivery of Biologically Active Substances Bound to Vitamin $B_{12}$); U.S. Pat. No. 5,608,060 to Axworthy et al (Biotinidase-Resistant Biotin-DOTA Conjugates); U.S. Pat. No. 5,807,832 to Russell-Jones et al (Oral Delivery of Biologically Active Substances Bound to Vitamin $B_{12}$); U.S. Pat. No. 5,869,465 to Morgan et al (Method of Receptor Modulation and Uses Therefor); U.S. Pat. No. 5,869,466 to Russell-Jones et al (vitamin $B_{12}$ Mediated Oral Delivery systems for GCSF).

See also Ruma Banerjee, *Chemistry and Biochemistry of $B_{12}$* John Wiley & Sons, Inc. (1999), and in particular Part II, Section 15 of that book, entitled "Diagnostics and Therapeutic Analogues of Cobalamin," by H. P. C. Hogenkamp, Douglas A. Collins, Charles B. Grissom, and Frederick G. West.

Despite the above findings, there remains a need for new compounds, compositions and methods to administer therapeutic and/or diagnostic agents that have improved specificity, i.e., which can localize the active agent efficiently in proliferating cells in high concentration compared to normal cells.

It is therefore an object of the invention to provide new compounds and compositions for the treatment, prophylaxis and/or diagnosis of abnormal cellular proliferation.

It is another object of the present invention to provide new methods, including surgical and medical methods, for the treatment, prophylaxis and/or diagnosis of proliferative conditions.

SUMMARY OF THE INVENTION

It has been discovered that an agent for the treatment, prophylaxis and/or diagnosis of a proliferative disorder is highly and effectively absorbed into a site of unwanted proliferation by direct or indirect attachment to a compound that binds to a transport protein for vitamin $B_{12}$, i.e. transcobalamin I, II or m, or intrinsic factor, (the TC- or IF-binding carrier) in a manner that ultimately allows binding to a transcobalamin receptor (TR).

The TC- or IF-binding carrier and therapeutic and/or diagnostic agent useful to treat and/or image sites of proliferative disease in the body, such as cancerous tumors, can optionally be joined by means of a di- or multi-valent linking moiety. The linker used to join the TC- or IF-binding carrier and the active agent preferably has a single molecular weight, and does not exhibit a molecular weight distribution, for example as found in most polymers. The linker can range in size from small to large molecular weight, as long as there is not a distribution of weights in the linker. It is important to strictly control the uniformity of size of the conjugate for predictability of therapeutic performance.

The linkers preferably have a molecular weight below about 2000, more preferably below about 1900 or 1800, and even more preferably below about 1500 or 1000.

Thus, in one embodiment the invention provides a therapeutic and/or diagnostic conjugate having a high specificity for abnormally proliferative cells, comprising (1) a TC- or IF-binding carrier, and (2) a therapeutic and/or diagnostic agent linked directly or through a linker to the TC- or IF-binding carrier, wherein the linker has either (i) a unimodal (i.e., single) and defined molecular weight, or (ii) a molecular weight less than about 2000, and preferably, below 1900, 1800, or 1500.

In one embodiment, the TC- or IF-binding carrier is any moiety that will bind to a transcobalamin receptor, optionally when complexed with the transport protein, and can be linked to a therapeutic and/or diagnostic agent. Methods for the assessment of whether a moiety binds the TC receptor are known, and include those described by Pathare, et al., (1996) *Bioconjugate Chem.* 7, 217-232; and Pathare, et al., *Bioconjugate Chem.* 8, 161-172. An assay that assesses binding to a mixture of transcobalamin I and II receptors is found in Chaiken, et al, *Anal. Biochem.* 201, 197 (1992). An unsaturated vitamin $B_{12}$ binding capacity (UBBC) assay to assess the in vitro binding of the conjugate to the transcobalamin transport proteins is described by D. A. Collins and H. P. C. Hogenkamp in *J. Nuclear Medicine*, 1997, 38, 717-723. See also Fairbanks, V. F. *Mayo Clinical Proc.* 83, Vol 58, 203-204.

In a particular embodiment of the present invention, the TC binding carrier or IF binding carrier is represented by formula (I).

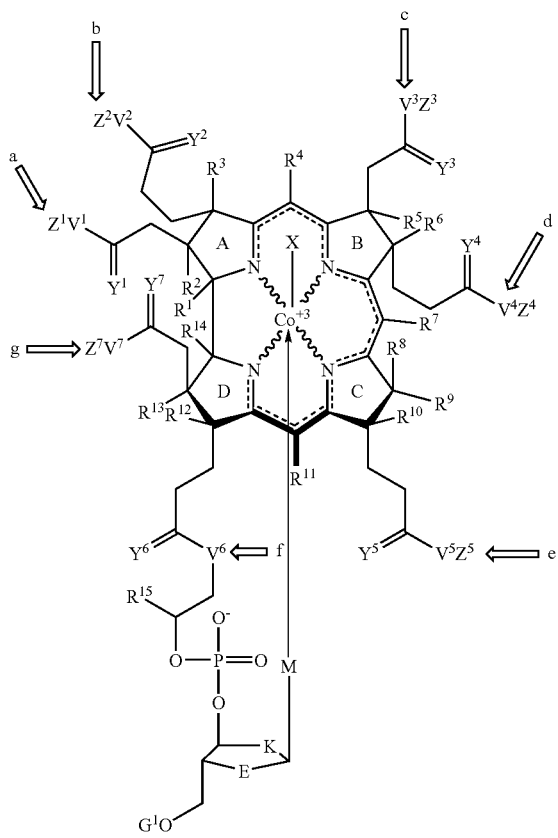

or its enantiomer, diastereomer or its pharmaceutically acceptable salt or prodrug, wherein:

(i) the wavy line in the chemical structure indicates either a dative or covalent bond such that there are three dative Co—N bonds and one covalent Co—N bond, wherein, in the case of the dative bond, the valence of nitrogen is completed either with a double bond with an adjacent ring carbon or with a hydrogen;

(ii) the dotted line in the chemical structure indicates either a double or single bond such that the double bond does not over-extend the valence of the element (i.e. to give pentavalent carbons) and, in the case of a single bond, the valence is completed with hydrogen; wherein, in a preferred embodiment, the bonding and stereochemistry of the compound is the same as that of vitamin $B_{12}$ as it exists in nature;

(iii) X is hydrogen, cyano, halogen (Cl, F, Br or I), haloalkyl (including $CF_3$, $CF_2CF_3$, $CH_2CF_3$ and $CF_2Cl$), NO, $NO_2$, $NO_3$, phosphonate(including alkyl-$P(O)_2$ $OR^{15}$), $PR^{15}R^{16}R^{17}$, $NH_2$, $NR^{15}R^{16}$, OH, $OR^{15}$, $SR^{15}$, SCN, $N_3$, $OC(O)R^{15}$, $C(O)_2R^{15}$, $C(O)R^{15}$, $OC(O)NR^{15}R^{16}$, $C(O)_2NR^{15}R^{16}$, $C(O)NR^{15}R^{16}$, $P(O)_2OR^{15}$, $S(O)_2OR^{15}$, a purine or pyrimidine nucleoside or nucleoside analog, including adenosyl (preferably linked through a 5'-deoxy linkage) and 5-FU, alkyl, alkenyl, alkynyl, aryl, aralkyl, alkaryl, amino acid, peptide, protein, carbohydrate, heteroalkyl, heterocycle, heteroaryl or alkylheteroaryl (in one embodiment that is less preferred, X is L-T);

(iv) M is a monovalent heterocycle or heteroaromatic, which is capable of binding to the adjacent sugar ring, and forming a dative bond with $Co^{+3}$, and is preferably a benzimidazole, a 5- and/or 6-substituted benzimidazole, such as 5,6-dimethylbenzimidazole, 5-methyl-benzimidazole, 5-hydroxy-benzimidazole, 5-methoxy-benzimidazole, naphth-imidazole, 5-hydroxy-6-methyl-benzimidazole or 5-methoxy-6-methyl-benz-imidazole; or a purine or pyrimidine including but not limited to adenine, 2-methyladenine, 2-methylmercaptoadenine, e-methylsulfinyladenine, 2-methyl-sulfonyladenine and guanine; or a phenol, such as phenol or p-cresol;

(v) K is O, S, $NJ^1$, $C(OH)H$, $CR^{100}R^{101}$ or $C(R^{100})V^8Z^8$;

(vi) E is O or S;

(vii) $G^1$ is hydrogen, alkyl, acyl, silyl, phosphate or L-T;

(viii) $Y^1$, $Y^2$, $Y^3$, $Y^4$, $Y^5$, $Y^6$ and $Y^7$ independently are O, S or $NJ^2$;

(ix) $V^1$, $V^2$, $V^3$, $V^4$, $V^5$, $V^6$, $V^7$ and $V^8$ independently are O, S, $NJ^3$, $CR^{102}R^{103}$ or a direct bond;

(x) $Z^1$, $Z^2$, $Z^3$, $Z^4$, $Z^5$, $Z^7$ and $Z^8$ independently are $R^{104}$ or L-T;

(xi) each L is independently a direct bond or a linker to one or more T moieties, and that does not significantly impair the ability of the TC- or IF-binding carrier to bind to a transcobalamin receptor, optionally when bound to a transport protein;

(xii) each T independently comprises the residue of a therapeutic and/or diagnostic agent, optionally bound though a chelating moiety if necessary or desired (in one embodiment, T is a therapeutic and/or diagnostic agent for the treatment, prophylaxis and/or diagnosis of a proliferative disorder other than cancer);

(xiii) at least one of $Z^1$, $Z^2$, $Z^3$, $Z^4$, $Z^5$, $Z^7$, $Z^8$, K and $G^1$ is L-T (in a preferred embodiment, $Z^2$ comprises the sole L-T in the TC- or IF-binding carrier);

(xiv) $J^1$, $J^2$ and $J^3$ independently are hydrogen, alkyl, alkenyl, alkynyl, alkaryl, cycloalkyl, aryl, cycloaryl, heteroalkyl, heterocycle, heteroaryl, hydroxyl, alkoxy or amine;

(xv) $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ independently are hydrogen, lower alkyl, lower alkenyl, lower alkynyl, lower cycloalkyl, heteroalkyl, heterocyclic, lower alkoxy, azido, amino, lower alkylamino, halogen, thiol, $SO_2$, $SO_3$, carboxylic acid, $C_{1-6}$ carboxyl, hydroxyl, nitro, cyano, oxime or hydrazine;

(xvi) $R^{13}$ and $R^{14}$ optionally can form a double bond;

(xvii) $R^{15}$, $R^{16}$ and $R^{17}$ are independently hydrogen, alkyl, alkenyl, alkynyl, aryl, alkaryl or aralkyl group, heteroalkyl, heterocycle or heteroaromatic; and (xviii) $R^{100}$, $R^{101}$, $R^{102}$, $R^{103}$, and $R^{104}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl or amino.

In a preferred embodiment, L is a linker, and in particular a polymer linker, of singular molecular weight.

In naturally occurring vitamin $B_{12}$, there is an α-D-5,6-dimethylbenzimidazolyl ribose 3'-phosphate that is bound through the phosphate to the $B_{12}$ moiety and coordinated to the cobalt ion. In a modified vitamin $B_{12}$ TC- or IF-binding carrier, the M-sugar component is likewise in an α-D configuration, although other configurations (i.e., α-L, β-D and β-L) are possible.

One of the biologically active forms of vitamin $B_{12}$ has a 5'-deoxyadenosyl moiety in the X position. Vitamin $B_{12}$ catalysis occurs via the detachment and reattachment of the methylene radical at the 5'-deoxy position of the adenosyl moiety. In one embodiment, the selected substituent in the X position is capable of similar catalysis.

In one particular embodiment the linker used to attach the TC- or IF-binding carrier and the therapeutic and/or diagnostic agent is a polyamine such as spermine or spermidine.

In another embodiment X comprises the residue of 5'-deoxyadenosine.

In one embodiment, the TC- or IF-binding carrier comprises one or more therapeutic and/or diagnostic agents at each of one or more of the b-, d-, or e-cobalamin positions, linked directly or through a linker, and preferably through the b-position.

In another embodiment the TC- or IF-binding carrier of the present invention comprises one or more therapeutic and/or diagnostic agents at M, K or $G^1$.

The present invention also provides a method of imaging a disorder characterized by abnormal cell proliferation in an animal, preferably a human, comprising administering to the animal an effective amount of a TC- or IF-binding carrier of the present invention.

The invention also provides the use of a compound of the present invention for the manufacture of a medicament for the treatment, prophylaxis and/or diagnosis of a disorder characterized by abnormal cellular proliferation in an animal (e.g., a human).

In one embodiment, the compound of formula I can be understood to exclude compounds (and therapeutic methods using such compounds) in which:
  (i) X is cyano, hydroxyl, methyl, adenosine or L-T;
  (ii) M is the residue of 5,6-dimethylbenzimidazole;
  (iii) E is O;
  (iv) K is C(OH)H;
  (v) $G^1$ is hydrogen;
  (vi) $Y^1, Y^2, Y^3, Y^4, Y^5, Y^6$ and $Y^7$ are O;
  (vii) L is a direct bond or a multivalent linker derived from a dicarboxylic acid (C(O)OH-alkylene-C(O)OH), a diamine ($NH_2$-alkylene-$NH_2$), an amino-carboxylic acid (C(O)OH-alkylene-$NH_2$), an amino acid, a peptide or a polymer of one or amino acids;
  (viii) $J^1$, $J^2$ and $J^3$ are all hydrogen;
  (ix) all of $R^1$, $R^2$, $R^4$, $R^5$, $R^8$, $R^9$, $R^{11}$, $R^{12}$ and $R^{15}$ are methyl and all of $R^3$, $R^6$, $R^7$, $R^{10}$, $R^{13}$ and $R^{14}$ are hydrogen; and/or
  (x) $V^1Z^1$, $V^3Z^3$, $V^6Z^6$ and $V^7Z^7$ are amino.

The present invention includes at least the following:
(a) a TC- or IF-binding carrier of the present invention linked directly or via a linker to one or more therapeutic and/or diagnostic agent(s), or the pharmaceutically acceptable salt or prodrug thereof, for the treatment, prophylaxis and/or diagnosis of a proliferative disorder;
(b) a pharmaceutical composition for the treatment, prophylaxis and/or diagnosis of a proliferative disorder comprising an effective amount of a TC- or IF-binding carriers of the present invention linked directly or via a linker to one or more therapeutic and/or diagnostic agent(s), or the pharmaceutically acceptable salt or prodrug thereof, in combination with a pharmaceutically acceptable carrier of diluent;
(c) a pharmaceutical composition for the treatment, prophylaxis and/or diagnosis of a proliferative disorder comprising an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent, in combination with one or more other effective therapeutic and/or diagnostic agent(s), or the pharmaceutically acceptable salt or prodrug thereof;
(d) a method for the treatment, prophylaxis and/or diagnosis of a proliferative disorder in a host, and in particular a human, comprising administering an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent;
(e) a method for the treatment, prophylaxis and/or diagnosis of a proliferative disorder in a host, and in particular a human, comprising administering an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent in combination or alternation with one or more other effective therapeutic and/or diagnostic agent(s), or its pharmaceutically acceptable salt or prodrug thereof;
(f) use of an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent, for the treatment, prophylaxis and/or diagnosis of a proliferative disorder in a host, and in particular a human;
(g) use of an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent, in combination or alternation with one or more other effective therapeutic and/or diagnostic agent(s), or the pharmaceutically acceptable salt or prodrug thereof, for the treatment, prophylaxis and/or diagnosis of a proliferative disorder;
(h) use of an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent, in the manufacture of a medicament for the treatment, prophylaxis and/or diagnosis of a proliferative disorder in a host, and in particular a human; and
(i) use of an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent, in combination or alternation with one or more other effective therapeutic and/or diagnostic agent(s), or the pharmaceutically acceptable salt or prodrug thereof, in the manufacture of a medicament for the treatment, prophylaxis and/or diagnosis of a proliferative disorder.

In a preferred embodiment, a therapeutic and/or diagnostic agent and the TC- or IF-binding carrier, or a pharmaceutically acceptable salt or prodrug thereof, is delivered to the site of unwanted proliferation in a manner that bypasses, or at least does not rely on, the gastrointestinal route of absorption via the vitamin $B_{12}$ intrinsic factor binding protein. Preferred modes of administration are parenteral, intraperitoneal, intravenous, intradermal, epidural, intraspinal, intrastemal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter. In one embodiment, the agent and carrier are administered in a slow release formulation such as a direct tissue injection or bolus, implant, microparticle, microsphere, nanoparticle or nanosphere.

It is preferred that the TC- or IF-binding carrier and the therapeutic and/or diagnostic agent be administered parenterally and not orally to increase the effectiveness of the agent, for example, in the case of imaging, to decrease the exposure of normal cells to the diagnostic agent. It is known that the ileal receptor for intrinsic factor-cobalamin complex is present in the gastrointestinal tract in only very small quantities, and on oral delivery of vitamin $B_{12}$ into the alimentary system the ileal receptor can only absorb approximately two micrograms per day of vitamin $B_{12}$ for systemic delivery. Even assuming a small amount of systemic absorption via passive transport of a large oral dose, this level of administration is insufficient for the treatment, prophylaxis and/or diagnosis of a proliferative disorder.

In an alternative embodiment, it has been discovered that an agent for the treatment, prophylaxis and/or diagnosis of a proliferative disorder can be highly and effectively absorbed into a site of unwanted proliferation by direct or indirect attachment to a compound that binds to the intrinsic factor (IF-binding carrier), wherein the IF-binding carrier and therapeutic and/or diagnostic agent are administered using any of the methods listed above, for example, parenterally.

The TC- or IF-binding carrier and the therapeutic and/or diagnostic agent, or a pharmaceutically acceptable salt or prodrug thereof, can be administered in the course of surgical or medical treatment, prophylaxis and/or diagnosis of the afflicted site. For example, the TC- or IF-binding carrier and active agent can be positioned directly at the site of proliferation during the course of surgery either by painting the formulation (with or without a controlled release matrix) onto the surface of the afflicted area or by depositing a bolus of material in a suitable matrix that is released into the afflicted area over time. In another embodiment, the TC- or IF-binding carrier and the active agent are administered directly into the proliferative mass via injection or catheter.

In another embodiment, the TC- or IF-binding carrier and the therapeutic and/or diagnostic agent is combined with either intrinsic factor or a transcobalamin carrier protein, or both, and administered parenterally, for example, via intravenous, intramuscular, direct injection or catheter, to the afflicted location.

BRIEF DESCRIPTION OF THE FIGURES

FIG. 6 illustrates a synthesis of a compound of the present invention (11) wherein a residue of a compound of formula I is linked to a peptide residue that comprises a non-metallic radionuclide (e.g., Fluorine-18).

DETAILED DESCRIPTION OF THE INVENTION

Figure 1:
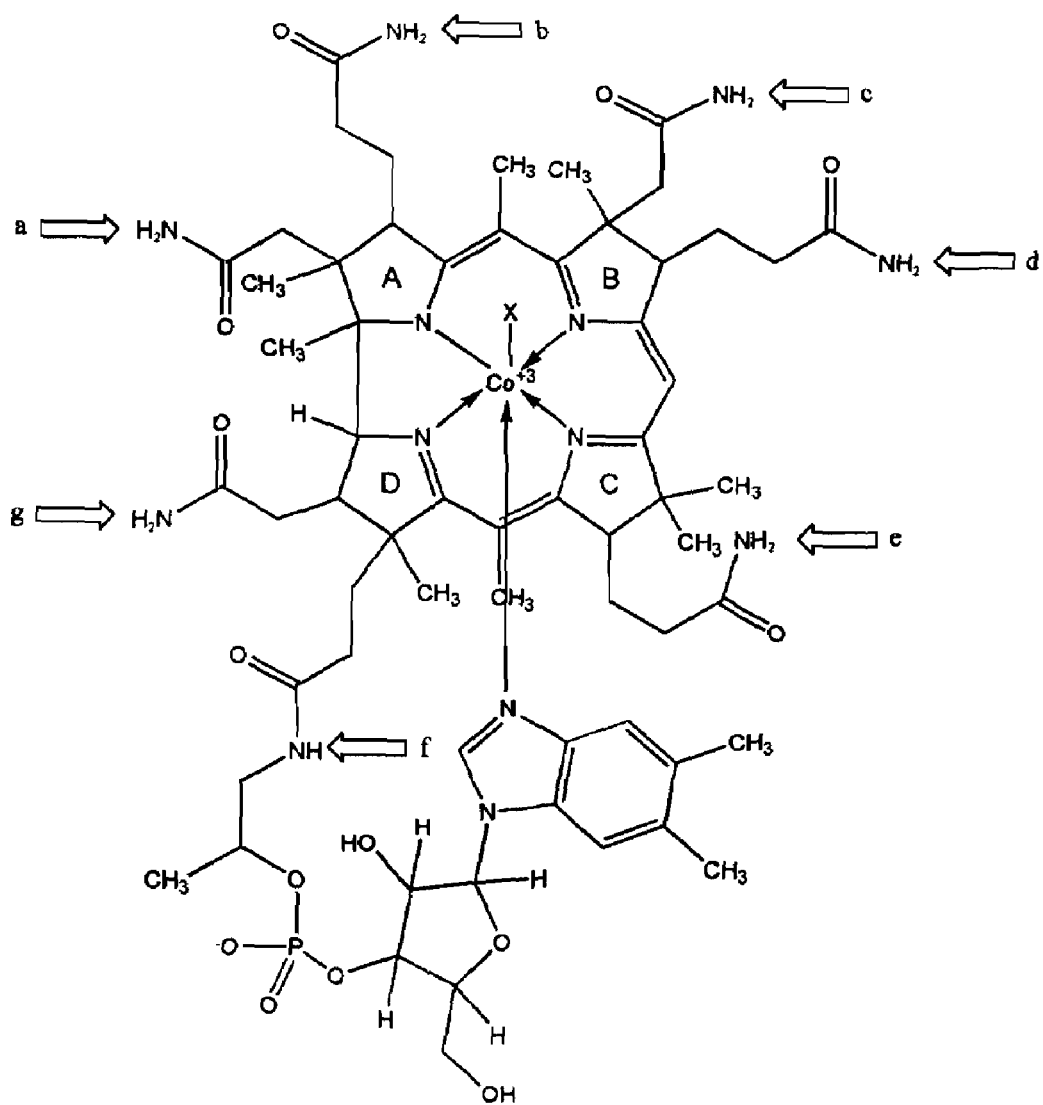
FIG. 1 illustrates a compound of formula I, wherein X is CN, OH, $CH_3$, adenosyl or a residue of a peptide or amino acid. The compound of formula I can be cyanocobalamin (X is CN), hydroxocobalamin (X is OH), methylcobalamin (X is $CH_3$), adenosylcobalamin (X is adenosyl), or a cobalamin conjugate (X is a residue of a peptide or amino acid).
Figure 2:
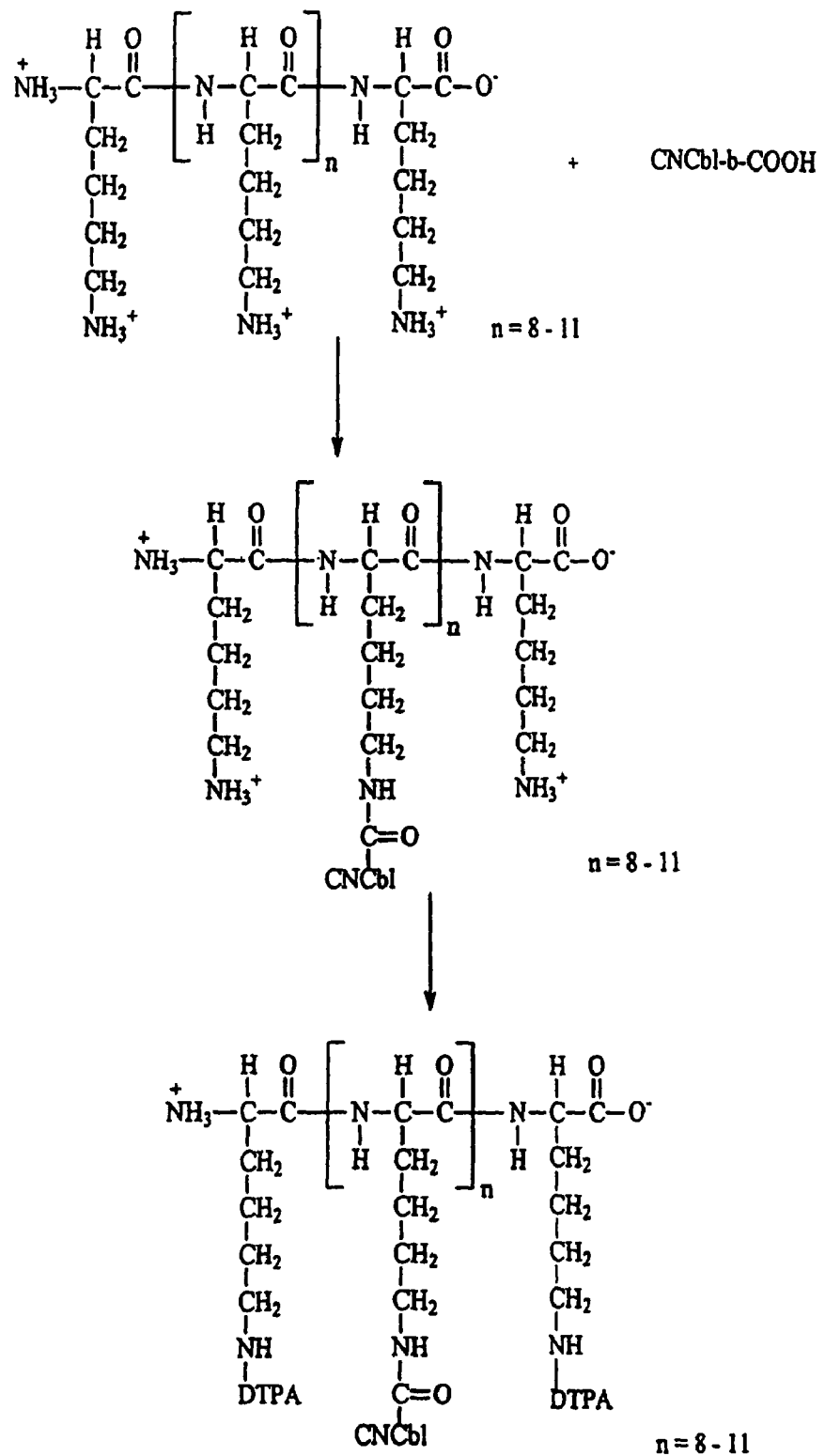
FIG. 2 illustrates a synthesis of a compound wherein a residue of a compound of formula I is linked to poly-L-lysine, 8 units to 11 units, linked to DTPA.

It has been discovered that an agent for the treatment, prophylaxis and/or diagnosis of a proliferative disorder is highly and effectively absorbed into a site of unwanted proliferation by direct or indirect attachment to a compound that binds to a transport protein for vitamin $B_{12}$, i.e. transcobalamin I, II or III, or intrinsic factor, (the TC- or IF-binding carrier) in a manner that ultimately allows binding to a transcobalamin receptor (TR).

Therefore, the present invention includes at least the following:

(a) a TC- or IF-binding carrier of the present invention linked directly or via a linker to one or more therapeutic and/or diagnostic agent(s), or the pharmaceutically acceptable salt or prodrug thereof, for the treatment, prophylaxis and/or diagnosis of a proliferative disorder;

(b) a pharmaceutical composition for the treatment, prophylaxis and/or diagnosis of a proliferative disorder comprising an effective amount of a TC- or IF-binding carriers of the present invention linked directly or via a linker to one or more therapeutic and/or diagnostic agent(s), or the pharmaceutically acceptable salt or prodrug thereof, in combination with a pharmaceutically acceptable carrier of diluent;

(c) a pharmaceutical composition for the treatment, prophylaxis and/or diagnosis of a proliferative disorder comprising an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent, in combination with one or more other effective therapeutic and/or diagnostic agent(s), or the pharmaceutically acceptable salt or prodrug thereof;

(d) a method for the treatment, prophylaxis and/or diagnosis of a proliferative disorder in a host, and in particular a human, comprising administering an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent;

(e) a method for the treatment, prophylaxis and/or diagnosis of a proliferative disorder in a host, and in particular a human, comprising administering an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent in combination or alternation with one or more other effective therapeutic and/or diagnostic agent(s), or its pharmaceutically acceptable salt or prodrug thereof;

(f) use of an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent, for the treatment, prophylaxis and/or diagnosis of a proliferative disorder in a host, and in particular a human;

(g) use of an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent, in combination or alternation with one or more other effective therapeutic and/or diagnostic agent(s), or the pharmaceutically acceptable salt or prodrug thereof, for the treatment, prophylaxis and/or diagnosis of a proliferative disorder;

(h) use of an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent, in the manufacture of a medicament for the treatment, prophylaxis and/or diagnosis of a proliferative disorder in a host, and in particular a human; and (i) use of an effective amount of a TC- or IF-binding carrier of the present invention linked directly or via a linker to one or more therapeutic and/or diagnostic agent(s), or the pharmaceutically acceptable salt or prodrug thereof, optionally with a pharmaceutically acceptable carrier or diluent, in combination or alternation with one or more other effective therapeutic and/or diagnostic agent(s), or the pharmaceutically acceptable salt or prodrug thereof, in the manufacture of a medicament for the treatment, prophylaxis and/or diagnosis of a proliferative disorder.

The TC-or IF-binding carrier and therapeutic and/or diagnostic agent useful to treat and/or image sites of proliferative disease in the body, such as cancerous tumors, can optionally be joined by means of a di- or multi-valent linking moiety. The linker used to join the TC- or IF-binding carrier and the active agent preferably has a single molecular weight, and does not exhibit a molecular weight distribution, for example as found in most polymers. The linker can range in size from small to large molecular weight, as long as there is not a distribution of weights in the linker. It is important to strictly control the uniformity of size of the conjugate for predictability of therapeutic performance.

The linkers preferably have a molecular weight below about 2000, more preferably below about 1900 or 1800, and even more preferably below about 1500 or 1000.

Thus, in one embodiment the invention provides a non-oral or oral pharmaceutical formulation comprising a therapeutic and/or diagnostic conjugate having a high specificity for abnormally proliferative cells, comprising (1) a transcobalamin (TC) or intrinsic factor (IF) binding carrier, and (2) a therapeutic and/or diagnostic agent linked directly or through a linker to the TC- or IF-binding carrier.

In a particular embodiment the invention provides a therapeutic and/or diagnostic conjugate having a high specificity for abnormally proliferative cells, comprising (1) a transcobalamin (TC) or intrinsic factor (IF) binding carrier, and (2) a therapeutic and/or diagnostic agent linked directly or through a linker to the TC- or IF-binding carrier, wherein the linker has either (i) a unimodal (i.e., single) and defined molecular weight, or (ii) a molecular weight less than about 2000, and preferably, below 1900, 1800 or 1500.

I. Definitions

The following definitions and term construction are intended, unless otherwise indicated:

Specific and preferred values listed below for radicals, substituents and ranges, are for illustration only; they do not exclude other defined values or other values within defined ranges for the radicals and substituents.

Halo is fluoro, chloro, bromo or iodo.

Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

The term heterocycle or heterocyclic, as used herein except where noted represents a stable 5- to 7-membered monocyclic or stable 8- to 11-membered bicyclic heterocyclic ring which is either saturated or unsaturated, and which consists of carbon atoms and from one to three heteroatoms selected from the group consisting of N, O and S; and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom that results in the creation of a stable structure.

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The terms "alkenyl" and "alkynyl" refer to alkyl moieties wherein at least one saturated C—C bond is replaced by a double or triple bond. Thus, $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. Similarly, $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkylene" refers to a saturated, straight chain, divalent alkyl radical of the formula —$(CH_2)_n$—, wherein n can be 1, 2, 3, 4, 5, 6, 7, 8, 9, or 10.

As used herein, with exceptions as noted, "aryl" is intended to mean any stable monocyclic, bicyclic or tricyclic carbon ring of up to 8 members in each ring, wherein at least one ring is aromatic as defined by the Huckel 4n+2 rule. Examples of aryl ring systems include phenyl, naphthyl, tetrahydronaphthyl and biphenyl. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercapto-pyrimidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diamino-purine and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl and t-butyldiphenylsilyl, trityl, alkyl groups, and acyl groups such as acetyl and propionyl, methanesulfonyl, and p-toluenesulfonyl.

The term heteroalkyl refers to an alkyl group that contains a heteroatom in the alkyl chain, including O, S, N, or P, and wherein the heteroatom can be attached to other substituents (including $R^{15}$) to complete the valence. Nonlimiting examples of heteroalkyl moieties include polyoxyalkylene, and when divalent, $-(CH_2O)n-$ wherein n is an integer of from 0 to 20.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term heteroaryl or heteroaromatic, as used herein, refers to an aromatic moiety that includes at least one sulfur, oxygen, nitrogen or phosphorus in the aromatic ring. The term heterocyclic refers to a nonaromatic cyclic group wherein there is at least one heteroatom, such as oxygen, sulfur, nitrogen or phosphorus in the ring. Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-aza-uracilyl, triazolopyridinyl, imidazolopyridinyl, pyrrolopyrimidinyl, pyrazolopyrimidinyl, adenine, N6-alkylpurines, N6-benzylpurine, N6-halopurine, N6-vinylpurine, N6-acetylenic purine, N6-acyl purine, N6-hydroxyalkyl purine, N6-thioalkyl purine, thymine, cytosine, 6-azapyrimidine, 2-mercaptopyrmidine, uracil, N5-alkyl-pyrimidines, N5-benzyl-pyrimidines, N5-halopyrimidines, N5-vinyl-pyrimidine, N5-acetylenic pyrimidine, N5-acyl pyrimidine, N5-hydroxyalkyl purine, and N6-thioalkyl purine, and isoxazolyl. The heteroaromatic and heterocyclic moieties can be optionally substituted as described above for aryl, including substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. As a nonlimiting example, dihydropyridine can be used in place of pyridine. Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl.

The term aralkyl, as used herein, and unless otherwise specified, refers to an aryl group as defined above linked to the molecule through an alkyl group as defined above. The term alkaryl, as used herein, and unless otherwise specified, refers to an alkyl group as defined above linked to the molecule through an aryl group as defined above.

The term alkoxy, as used herein, and unless otherwise specified, refers to a moiety of the structure —O-alkyl, wherein alkyl is as defined above.

The term amino, as used herein, refers to a moiety represented by the structure $-NR_2$, and includes primary amines, and secondary, and tertiary amines substituted by alkyl (i.e. alkylamino). Thus, $R_2$ may represent two hydrogens, two alkyl moieties, or one hydrogen and one alkyl moiety.

The term amido, as used herein, refers to a moiety represented by the structure $-C(O)NR_2$, wherein $R_2$ is as defined for amino.

As used herein, an "amino acid" is a natural amino acid residue (e.g. Ala, Arg, Asn, Asp, Cys, Glu, Gln, Gly, His, Hyl, Hyp, Ile, Leu Lys, Met, Phe, Pro, Ser, Thr, Trp, Tyr, and Val) in D or L form, or an unnatural amino acid (e.g. phosphoserine; phosphothreonine; phosphotyrosine; gamma-carboxyglutamate; hippuric acid; octahydroindole-2-carboxylic acid; statine; 1,2,3,4,-tetrahydroisoquinoline-3-carboxylic acid; penicillamine; ornithine; citrulline; α-methyl-alanine; para-benzoylphenylalanine; phenylglycine; propargyl-glycine; sarcosine; and tert-butylglycine) residue having one or more open valences. Other unnatural amino acids include those represented by the formula $NH_2$ $(CH_2)_y$ COOH, wherein y=2-20, and preferably 2-12, and include the aminoalkanoic acids such as e-amino caproic acid ($H_2N-(CH_2)_5-COOH$).

The term also comprises natural and unnatural amino acids bearing amino protecting groups such as acetyl, acyl, trifluoroacetyl, and benzyloxycarbonyl), as well as natural and unnatural amino acids protected at carboxy with protecting groups such as a $C_1$-$C_6$ alkyl, phenyl or benzyl ester or amide. Other suitable amino and carboxy protecting groups are known to those skilled in the art. See for example, T. W.

Greene, *Protecting Groups in Organic Synthesis*; Wiley: New York, 1981; D. Voet, Biochemistry, Wiley: New York, 1990; L. Stryer, *Biochemistry*, (3$^{rd}$ Ed), W. H. Freeman and Co.: New York, 1975; J. March, *Advanced Organic Chemistry, Reactions, Mechanisms and Structure*, (2$^{nd}$ Ed.), McGraw Hill: New York, 1977; F. Carey and R. Sundberg, *Advanced Organic Chemistry, Part B: Reactions and Synthesis*, (2$^{nd}$ Ed.), Plenum: New York, 1977; and references cited therein.

As used herein, a "peptide" is a sequence of 2 to 25 amino acids (e.g. as defined hereinabove) or peptidic residues having one or more open valences. The sequence may be linear or cyclic. For example, a cyclic peptide can be prepared or may result from the formation of disulfide bridges between two cysteine residues in a sequence.

The term "residue" is used throughout the specification to describe any pharmaceutically acceptable form of a therapeutic and/or diagnostic agent, which, upon administration to a patient, does not inhibit the action of the active agent. As a non-limiting example, a pharmaceutically acceptable residue of an active agent is one that is modified to facilitate binding to the TC- or IF-binding agent, covalently, ionically or through a chelating agent, such that the modification does not inhibit the biological action of the active agent, in that it does not inhibit the drugs ability to modulate abnormal cellular proliferation. In a preferred embodiment, the residue refers to the active agent with an open valence state such that covalent bonding to the compound is possible. This open valence state can be achieved by any means known in the art, including the methodology described herein. In a preferred embodiment, the open valence state is achieved through the removal of an atom, such as hydrogen, to activate a functional group.

As used herein, the term "substantially free of" or "substantially in the absence of" refers to a composition that includes at least 85 or 90% by weight, preferably 95% to 98% by weight, and even more preferably 99% to 100% by weight, of the designated enantiomer of that TC- or IF-binding agent. In a preferred embodiment, in the methods and compounds of this invention, the compounds are substantially free their enantiomers.

Similarly, the term "isolated" refers to a composition that includes at least 85 or 90% by weight, preferably 95% to 98% by weight, and even more preferably 99% to 100% by weight, of the TC- or IF-binding agent, the remainder comprising other chemical species, including diastereomers or enantiomers.

The term "independently" is used herein to indicate that the variable that is independently applied varies independently from application to application. Thus, in a compound such as R"XYR", wherein R" is "independently carbon or nitrogen," both R" can be carbon, both R" can be nitrogen, or one R" can be carbon and the other R" nitrogen.

The term "host," as used herein, refers to a multicellular organism in which proliferative disorders can occur, including animals, and preferably a human. Alternatively, the host is any abnormally proliferating cell, whose replication or function can be altered by the compounds of the present invention. The term host specifically refers to any cell line that abnormally proliferates, either from natural or unnatural causes (for example, from genetic mutation or genetic engineering, respectively), and animals, in particular, primates (including chimpanzees) and humans. In most animal applications of the present invention, the host is a human patient. Veterinary applications, in certain indications, however, are clearly anticipated by the present invention (such as bovine viral diarrhea virus in cattle, hog cholera virus in pigs, and border disease virus in sheep).

II. TC- or IF-Binding Carrier

In one embodiment, the TC- or IF-binding carrier is any ligand that will bind effectively to a vitamin $B_{12}$ transport protein (i.e. transcobalamin I, II or III or intrinsic factor) and which when appropriately linked to a therapeutic and/or diagnostic agent and bound to a transport protein, will fit into a transcobalamin receptor. Suitable carriers may be ascertained using any one of several means known in the art, including competitive binding assays with the receptor modulating agent competing with native vitamin $B_{12}$. Methods for the assessment of whether a moiety binds the TC receptor are known, and include those described by Pathare et al., *Bioconjugate Chem.* 1996, 7, 217-232; and Pathare, et al., *Bioconjugate Chem.* 8, 161-172. An assay that assesses binding to a mixture of transcobalamin I and II receptors is found in Chaiken, et al, *Anal. Biochem.* 1992, 201, 197. An unsaturated Vitamin $B_{12}$ binding capacity (UBBC) assay to assess the in vitro binding of the conjugate to the transcobalamin proteins is described by D. A. Collins and H. P. C. Hogenkamp in *J. Nuclear Medicine*, 1997, 38, 717-723. See also Fairbanks, V. F. *Mayo Clinical Proc.* 83, Vol 58, 203-204. See also Fairbanks, V. F. *Mayo Clinical Proc.* 83, Vol 58, 203-204. The TC- or IF-binding carrier preferably displays a binding affinity of at least 50% of the binding affinity displayed by vitamin $B_{12}$, more preferably at least 75% and even more preferably at least 90%.

In one embodiment, the therapeutic and/or diagnostic agent is bound directly or indirectly through an amide residue at the b-position, as illustrated in FIG. 1.

In another embodiment, the TC- or IF-binding carrier of the present invention is represented by formula (I),

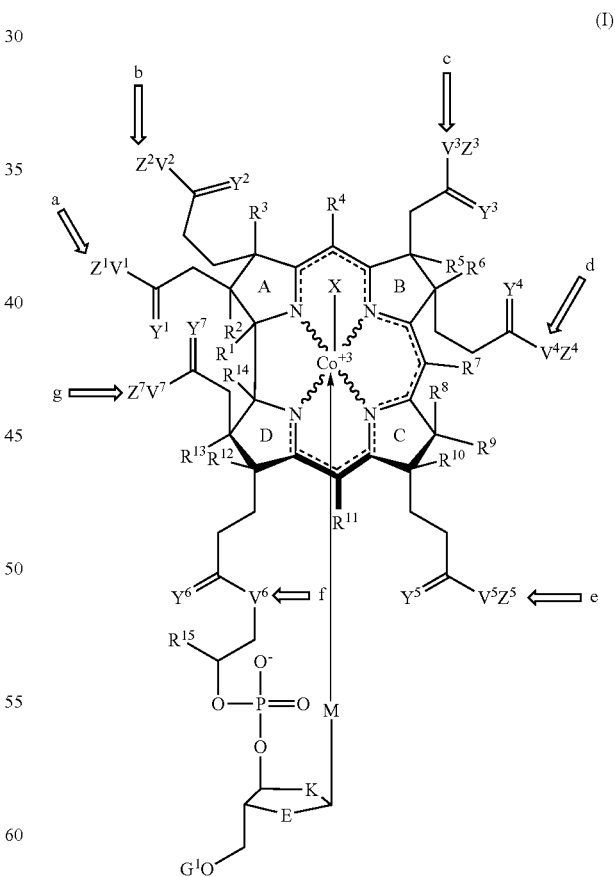

or its enantiomer, diastereomer or its pharmaceutically acceptable salt or prodrug, wherein:

(i) the wavy line in the chemical structure indicates either a dative or covalent bond such that there are three dative Co—N bonds and one covalent Co—N bond, wherein, in the case of the dative bond, the valence of nitrogen is completed either with a double bond with an adjacent ring carbon or with a hydrogen;

(ii) the dotted line in the chemical structure indicates either a double or single bond such that the double bond does not over-extend the valence of the element (i.e. to give pentavalent carbons) and, in the case of a single bond, the valence is completed with hydrogen; wherein, in a preferred embodiment, the bonding and stereochemistry of the compound is the same as that of vitamin $B_{12}$ as it exists in nature;

(iii) X is hydrogen, cyano, halogen (Cl, F, Br or I), haloalkyl (including $CF_3$, $CF_2CF_3$, $CH_2CF_3$ and $CF_2Cl$), NO, $NO_2$, $NO_3$, phosphonate (including alkyl-$P(O)_2$ $OR^{15}$), $PR^{15}R^{16}R^{17}$, $NH_2$, $NR^{15}R^{16}$, OH, $OR^{15}$, $SR^{15}$, SCN, $N_3$, $OC(O)R^{15}$, $C(O)_2R^{15}$, $C(O)R^{15}$, $OC(O)NR^{15}R^{16}$, $C(O)_2NR^{15}R^{16}$, $C(O)NR^{15}R^{16}$, $P(O)_2OR^{15}$, $S(O)_2R^{15}$, a purine or pyrimidine nucleoside or nucleoside analog, including adenosyl (preferably linked through a 5'-deoxy linkage) and 5-FU, alkyl, alkenyl, alkynyl, aryl, aralkyl, alkaryl, amino acid, peptide, protein, carbohydrate, heteroalkyl, heterocycle, heteroaryl or alkylheteroaryl (in one embodiment that is less preferred, X is L-T);

(iv) M is a monovalent heterocycle or heteroaromatic, which is capable of binding to the adjacent sugar ring, and forming a dative bond with $Co^{+3}$, and is preferably a benzimidazole, a 5- and/or 6-substituted benzimidazole, such as 5,6-dimethylbenzimidazole, 5-methyl-benzimidazole, 5-hydroxy-benzimidazole, 5-methoxy-benzimidazole, naphth-imidazole, 5-hydroxy-6-methyl-benzimidazole or 5-methoxy-6-methyl-benz-imidazole; or a purine or pyrimidine including but not limited to adenine, 2-methyladenine, 2-methylmercaptoadenine, e-methylsulfinyladenine, 2-methyl-sulfonyladenine and guanine; or a phenol, such as phenol or p-cresol;

(v) K is O, S, $NJ^1$, $C(OH)H$, $CR^{100}R^{101}$ or $C(R^{100})V^8Z^8$;

(vi) E is O or S;

(vii) $G^1$ is hydrogen, alkyl, acyl, silyl, phosphate or L-T;

(viii) $Y^1, Y^2, Y^3, Y^4, Y^5, Y^6$ and $Y^7$ independently are O, S or $NJ^2$;

(ix) $V^1, V^2, V^3, V^4, V^5, V^6, V^7$ and $V^8$ independently are O, S, $NJ^3$, $CR^{102}R^{103}$ or a direct bond;

(x) $Z^1, Z^2, Z^3, Z^4, Z^5, Z^7$ and $Z^8$ independently are $R^{104}$ or L-T;

(xi) each L is independently a direct bond or a linker to one or more T moieties, and that does not significantly impair the ability of the TC- or IF-binding carrier to bind to a transcobalamin receptor, optionally when bound to a transport protein;

(xii) each T independently comprises the residue of a therapeutic and/or diagnostic agent, optionally bound though a chelating moiety if necessary or desired (in one embodiment, T is a therapeutic and/or diagnostic agent for the treatment, prophylaxis and/or diagnosis of a proliferative disorder other than cancer);

(xiii) at least of $Z^1, Z^2, Z^3, Z^4, Z^5, Z^7, Z^8$, K and $G^1$ is L-T (in a preferred embodiment, $Z^2$ comprises the sole L-T in the TC- or IF-binding carrier);

(xiv) $J^1, J^2$ and $J^3$ independently are hydrogen, alkyl, alkenyl, alkynyl, alkaryl, cycloalkyl, aryl, cycloaryl, heteroalkyl, heterocycle, heteroaryl, hydroxyl, alkoxy or amine;

(xv) $R^1, R^2, R^3, R^4, R^5, R^6, R^7, R^8, R^9, R^{10}, R^{11}, R^{12}, R^{13}$ and $R^{14}$ independently are hydrogen, lower alkyl, lower alkenyl, lower alkynyl, lower cycloalkyl, heteroalkyl, heterocyclic, lower alkoxy, azido, amino, lower alkylamino, halogen, thiol, $SO_2$, $SO_3$, carboxylic acid, $C_{1-6}$ carboxyl, hydroxyl, nitro, cyano, oxime or hydrazine;

(xvi) $R^{13}$ and $R^{14}$ optionally can form a double bond;

(xvii) $R^{15}$, $R^{16}$ and $R^{17}$ are independently hydrogen, alkyl, alkenyl, alkynyl, aryl, alkaryl or aralkyl group, heteroalkyl, heterocycle or heteroaromatic; and (xviii) $R^{100}$, $R^{101}$, $R^{102}$, $R^{103}$, and $R^{104}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl or amino.

In a preferred embodiment, L is a linker, and in particular a polymer linker, of singular molecular weight.

In naturally occurring vitamin $B_{12}$, there is an α-D-5,6-dimethylbenzimidazolyl ribose 3'-phosphate that is bound through the phosphate to the $B_{12}$ moiety and coordinated to the cobalt ion. In a modified vitamin $B_{12}$ TC- or IF-binding carrier, the M-sugar component is likewise in an α-D configuration, although other configurations (i.e., α-L, β-D and β-L) are possible.

One of the biologically active forms of vitamin $B_{12}$ has a 5'-deoxyadenosyl moiety in the X position. Coenzyme $B_{12}$ catalysis occurs via the detachment and reattachment of the methylene radical at the 5'-deoxy position of the vitamin.

In one particular embodiment the linker used to conjugate the TC- or IF-binding carrier and the therapeutic and/or diagnostic agent is a polyamine such as spermine or spermidine.

Because vitamin $B_{12}$ is preferentially taken up by abnormally proliferating cells, the TC- or IF-binding carrier/active agent of the present invention provides a delivery system capable of targeting abnormally proliferative cells, and selectively treating and/or imaging a greater proportion of such cells in relation to healthy cells. A wide range of analogs and derivatives are capable of attaining these properties, as reflected by the above referenced chemical structure and variables.

The TC- or IF-binding carrier can be modified in any manner that does not interfere with its fundamental ability to bind a transcobalamin transport protein, and thereafter bind the TC receptor. In one embodiment, however, each variable on the vitamin $B_{12}$ structure independently either (i) retains its natural vitamin $B_{12}$ structure, (ii) imparts imaging and/or anti-proliferative properties to the cobalamin conjugate, (iii) renders the cobalamin conjugate more water soluble, or more stable, (iv) increases the bioavailability of the carrier; (v) increases or at least does not decrease the binding affinity of the carrier for the TC-binding or IF-binding protein over vitamin $B_{12}$; or (vi) imparts another characteristic that is desired for pharmaceutical or diagnostic performance.

The therapeutic and/or diagnostic agent can be linked to the TC-binding or IF-binding moiety through a number of positions, including any of the V-Z moieties, the X moiety, the M moiety, the K moiety and/or the $G^1$ moiety, though as mentioned above at least one of $Z^1, Z^2, Z^3, Z^4, Z^5, Z^7, Z^8$, M, K and $G^1$ moieties comprises a therapeutic and/or diagnostic agent. In one embodiment a therapeutic and/or diagnostic agent is linked to the TC- or IF-binding carrier through $Z^2, Z^4$, and/or $Z^5$ (i.e. one or more of $Z^2, Z^4$, and $Z^5$ is L-T, and T is a therapeutic and/or diagnostic agent). In a more particular embodiment a therapeutic and/or diagnostic agent is linked to the TC- or IF-binding carrier through the $Z^2$ moiety (i.e. $Z^2$ is L-T, and T is a therapeutic and/or diagnostic agent). In each of the foregoing embodiments, the Z moiety or moieties not containing a therapeutic and/or diagnostic agent preferably retain its natural vitamin $B_{12}$ configuration, in which VZ is $NH_2$. Alternatively, the Z moieties not containing a therapeutic and/or diagnostic agent may comprise a secondary or tertiary amino analog of $NH_2$ substituted by one or two of $J^1$.

In any $Z^1, Z^2, Z^3, Z^4, Z^5, Z^6, Z^7 Z^8$ X, M, K, or $G^1$ moieties through which a therapeutic and/or diagnostic agent is linked, it will be understood that such moiety may comprise more than one therapeutic and/or diagnostic agent, or a combination of therapeutic and/or diagnostic agents, i.e., each T can independently comprise the residue of one or more therapeutic and/or diagnostic agents bound to L through one or more chelating moieties. More specifically, in a series of embodiments, each T can comprise 1, 2, 3, 4, 5, 6, 7, 8, 9 or 10 therapeutic and/or diagnostic agents bound through one or more chelating moieties.

$R^1, R^2, R^3, R^4, R^5, R^6, R^7, R^8, R^9, R^{10}, R^{11}, R^{12}$, and $R^{13}$ independently represent moieties that do not interfere with binding between the compound and the transcobalamin transport protein or receptor. Vitamin $B_{12}$ can be modified through these moieties to modulate physical properties of the molecule, such as water solubility, stability or $\lambda_{max}$. Preferred groups for enhancing water solubility include heteroalkyl, amino, $C_{1-6}$ alkylamino, $C_{1-6}$ alcohol, $C_{1-6}$ carboxylic acid and $SO_3^-$.

In another embodiment, one, some or all of $R^1, R^2, R^3, R^4, R^5, R^6, R^7, R^8, R^9, R^{10}, R^{11}, R^{12}$, and $R^{13}$ independently assume their natural roles in vitamin $B_{12}$. Thus, one, some, or all of $R^1, R^2, R^4, R^5, R^8, R^9, R^{11}, R^{12}$ and $R^{15}$ are independently methyl in one embodiment, and one, some, or all of $R^3, R^6, R^7, R^{10}, R^{13}$ and $R^{14}$ are independently hydrogen.

In another embodiment, one, some, or all of $Y^1, Y^2, Y^3, Y^4, Y^5, Y^6$ and $Y^7$ assume their natural roles in vitamin $B_{12}$, and are O. Similarly, in another embodiment $V^6$ assumes its natural role in vitamin $B_{12}$, and is NH, or a primary amine analog thereof substituted by $J^1$.

In still another embodiment, position X assumes its natural role in vitamin $B_{12}$, i.e. as cyano, hydroxyl, methyl or 5'-deoxyadenosyl, most preferably 5'-deoxyadenosyl.

In another embodiment M is the radical of a purine or pyrimidine base. In another embodiment M is the radical of adenosine, guanine, cytosine, uridine or thymine. In still another embodiment M is the radical of 5,6-dimethylbenzimidazole.

In still another embodiment K is CH(OH).

In yet another embodiment E is O.

In another embodiment $G^1$ is OH.

In still another embodiment, all constituents of the conjugate assume their natural roles in vitamin $B_{12}$, except for the moieties through which any therapeutic and/or diagnostic agents are linked. The therapeutic and/or diagnostic agent(s) are preferably linked to the vitamin $B_{12}$ structure through $Z^2$, $Z^4$ and/or $Z^5$, and even more preferably through the $Z^2$ moieties.

In still another embodiment, T is not a residue of a therapeutic agent selected from the group consisting of hormone, growth factor, interleukin, cytokines, lymphokines, GCSF, EPO, interferon ($\alpha$, $\beta$, $\gamma$), calcitonin, TRH, vasopressin, desmopressin [Folia Endocrinologica Japonica 54, No. 5, p. 676-691 (1978)], oxytocin, insulin, Growth Hormone, testosterone, somatotrophin, somatostatin (U.S. Pat. Nos. 4,087,390 and 4,100,117), SCGF, (stem cell growth factor), CGRP, Erythropoietin, Colony Stimulating factors (GCSF, GM-CSF, CSF), pregnant mare serum gonadotrophin (PMSG), human chorionic gonadotrophin (HCG), Inhibin, PAI-2; neomycin, salbutamol, pyrimethamine, penicillin G, methicillin, carbenicillin, pethidine, xylazine, ketamine, mephenesin, GABA, iron dextran, nucleotide analogues or ribozyme, prolactin, adrenocorticotropic hormone (ACTH), melanocyte stimulating hormone (MSH), thyroid hormone releasing hormone (TRH) (U.S. Pat. No. 4,100,152), thyroid stimulating hormone (TSH), luteinizing hormone (LH), luteinizing hormone releasing hormone (LHRH), follicle stimulating hormone (FSH), oxytocin, calcitonin, parathyroid hormone, glucagon, gastrin, secretin, pancreozymin, cholecystokinin angiotensin, human placental lactogen, human chorionic gonadotropin (HCG), enkephalin [U.S. Pat. No. 4,277,394, European patent application Publication No. 31567], endorphin, kyotorphin, interleukins (I, II, and III), tuftsin, thymopoietin, thymosin, thymostimulin, thymic humoral factor (TFH), serum thymic factor (FTS) (U.S. Pat. No. 4,229,438), thymic factors [Medicine in Progress 125, No. 10, p. 835-843 (1983)], tumor necrosis factor (TNF), colony stimulating factor (CSF), motilin, dinorphin, bombesin, neurotensin, cerulein, bradykinin, urokinase, asparaginase, kallikrein, substance P analogue and antagonist, nerve growth factor, blood coagulation factors VIII and IX, lysozyme chloride, polymixin B, colistin, gramicidin, bacitracin, protein synthesis stimulating peptides (British patent No. 8232082), gastric inhibitory polypeptide (GIP), vasoactive intestinal polypeptide (VIP), platelet-derived growth factor (PDGF), growth hormone factor (GRF, somatocrinin), bone morphogenetic protein (BMP), epidermal growth factor (EGF), bleomycin, methotrexate, actinomycin D, mitomycin C, vinblastine sulfate, vincristine sulfate, daunorubicin, adriamycin, neocarzinostatin, cytosine arabinoside, fluorouracil, tetrahydroftiryl-5-fluorouracil, krestin, picibanil, lentinan, levamisole, bestatin, azimexon, glycyrrhizin, poly I:C, poly A:U and poly ICLC, gentamicin, dibekacin, kanendomycin, lividomycin, tobramycin, amikacin, fradiomycin, sisomicin, tetracycline hydrochloride, oxytetracycline hydrochloride, rolitetracycline, doxycycline hydrochloride, ampicillin, piperacillin, ticarcillin, cephalothin, cephaloridine, cefotiam, cefsulodin, cefmenoxime, cefmetazole, cefazolin, cefotaxime, cefoperazone, ceftizoxime, moxolactam, latamoxef, thienamycin, sulfazecin, azthreonam, sodium salicylate, sulpyrine, sodium flufenamate, sodium diclofenac, sodium indomethacin, morphine hydrochloride, pethidine, levorphanol tartrate, oxymorphone, ephedrine, methylephedrine, noscapine, codeine phosphate, dihydrocodeine, phosphate, alloclamide, chlophedianol, picoperidamine, cloperastine, protokylol, isoproterenol, salbutamol, terbutaline sulfate, chlorpromazine, prochlorperazine, trifluoperazine, atropine sulfate, scopolamine methylbromide, pridinol methanesulfonate, tubocurarine chloride and pancuronium bromide, sodium phenytoin, ethosuximide, sodium acetazolamide, chlordiazepoxide hydrochloride, metoclopramide and L-histidine monohydrochloride, irnipramine, clomipramine, noxiptiline, phenelzine sulfate, diphenhydramine, chlorpheniramine maleate, tripelenamine, methdilazine, clemizole, diphenylpyraline, methoxyphenamine, trans-p-oxocamphor, theophyllol, aminophylline, etilefrine, propranolol, alprenolol, bufetolol, oxyprenolol, oxyfedrine, diltiazem, tolazoline, hexobendine, bamethan sulfate, hexamethonium bromide, pentolinium, mecamlamine, ecarazine, clonidine, sodium glymidine, glypizide, phenformin, buformin, metformin, sodium heparin, sodium citrate, thromboplastin, thrombin, menadione sodium bisulfite, acetomenaphthone, .epsilon.-amino-caproic acid, tranexamic acid, carbazochrome sodium sulfonate, adrenochrome monoaminoguanidine methanesulfonate, isoniazid, ethambutol, sodium p-aminosalicylate, prednisolone succinate, prednisolone sodium phosphate, dexamethasone sodium sulfate, betamethasone sodium phosphate, hexestrol phosphate, hexestrol acetate, methimazole, levallorphan tartrate, nalorphine hydrochloride and naloxone hydrochloride; a protein derived from or immunogens against influenza, measles, Rubella, smallpox, yellow fever, diphtheria, tetanus, cholera, plague, typhus, BCG, tuberculosis causing agents, *Haemophilus influenzae, Neisseria catarrhalis, Klebsiella pneumoniae*, pneumococci, streptococci; a secretory product derived from diphtheria, tetanus, cholera, plague, typhus, tuberculosis causing agents, *Haemophilus influenzae, Neisseria catarrhalis, Klebsiella pneumoniae*, pneumococci, streptococci, *Streptococcus mutans*, or is derived from a malarial parasite or the causative agent of coccidiosis in chickens.

The above discussion has demonstrated how the various variables associated with the cobalamin conjugates of the present invention can be independently varied to more particularly define specific classes of cobalamin conjugates encompassed by this invention. It is to be understood that the modification of one variable can be made independently of the modification of any other variable. Moreover, any number of embodiments can be defined by modifying two or more of the variables in such embodiments. A few of such embodiments are described below for purposes of exemplification.

Subembodiment 1: X is 5'-deoxyadenosyl; M is a monovalent heterocycle that is capable of binding to the adjacent sugar ring, and forming a dative bond with $Co^{+3}$, optionally substituted by L-T; K is O, S, $NJ^1$, $CR^{100}R^{101}$, or $C(R^{100})V^8Z^8$; E is O or S; $G^1$ is hydrogen, alkyl, acyl, silyl, phosphate, or L-T; $Y^1, Y^2, Y^3, Y^4, Y^5, Y^6$ and $Y^7$ independently are O, S or $NJ^2$; $V^1, V^2, V^3, V^4, V^5, V^6, V^7$ and $V^8$ independently are O, S or $NJ^3$; $CR^{102}R^{103}$, or a direct bond; $Z^1, Z^2, Z^3, Z^4, Z^5, Z^7$ and $Z^8$ independently are $R^{104}$ or L-T; each L is independently a direct bond or the residue of a multivalent moiety that does not significantly impair the ability of the compound to bind transcobalamin or intrinsic factor proteins; each T independently comprises the residue of one or more radionuclides; at least one of $Z^1, Z^2, Z^3, Z^4, Z^5, Z^7$ and $Z^8$, M, K, or $G^1$ comprises a radionuclide; $J^1, J^2$ and $J^3$ independently are hydrogen, alkyl, alkenyl, alkynyl, alkaryl, cycloalkyl, aryl, cycloaryl, heterocycle, heteroaryl, hydroxyl, alkoxy, or amine; $R^1, R^2, R^3, R^4, R^5, R^6, R^7, R^8, R^9, R^{10}, R^{11}, R^{12}, R^{13}, R^{14}$ and $R^{15}$ retain their natural vitamin $B_{12}$ configuration; and $R^{100}, R^{101}, R^{102}, R^{103}$, and $R^{104}$ are independently hydrogen, alkyl, alkenyl, alkynyl, hydroxyl, alkoxy, cyano, azido, halogen, nitro, $SO_2$, $SO_3$, thioalkyl, or amino.

Subembodiment 2: X is 5'-deoxyadenosyl; M, K, E and $G^1$ retain their natural vitamin B12 configuration; $Y^1, Y^2, Y^3, Y^4, Y^5, Y^6$ and $Y^7$ independently are O, S or $NJ^2$; $V^1, V^2, V^3, V^4, V^5, V^6, V^7$ and $V^8$ independently are O, S or $NJ^3$; $CR^{102}R^{103}$, or a direct bond; $Z^1, Z^2, Z^3, Z^4, Z^5, Z^7$ and $Z^8$ independently are $R^{104}$ or L-T; each L is independently a direct bond or the residue of a multivalent moiety that does not significantly impair the ability of the compound to bind transcobalamin or intrinsic factor proteins; each T independently comprises the residue of one or more radionuclides; at least one of $Z^1, Z^2, Z^3, Z^4, Z^5, Z^7$ and $Z^8$, M, K, or $G^1$ comprises a radionuclide; $J^1, J^2$ and $J^3$ independently are hydrogen, alkyl, alkenyl, alkynyl, alkaryl, cycloalkyl, aryl, cycloaryl, heterocycle, heteroaryl, hydroxyl, alkoxy, or amine; $R^1, R^2, R^3, R^4, R^5, R^6, R^7, R^8, R^9, R^{10}, R^{11}, R^{12}, R^{13}, R^{14}$ and $R^{15}$ independently are hydrogen, lower alkyl, lower alkenyl, lower alkynyl, lower cycloalkyl, heterocyclic, lower alkoxy, azido, amino, lower alkylamino, halogen, thiol, $SO_2$, $SO_3$, carboxylic acid, $C_{1-6}$ carboxyl, hydroxyl, nitro, cyano, oxime or hydrazine; $R^{13}$ and $R^{14}$ optionally can come together to form a double bond; and $R^{100}, R^{101}, R^{102}, R^{103}$, and $R^{104}$ are independently hydrogen, alkyl, alkenyl, alkynyl, hydroxyl, alkoxy, cyano, azido, halogen, nitro, $SO_2$, $SO_3$, thioalkyl, or amino.

Subembodiment 3: X is 5'-deoxyadenosyl; M is a monovalent heterocycle that is capable of binding to the adjacent sugar ring, and forming a dative bond with $Co^{+3}$, optionally substituted by L-T; K is O, S, $NJ^1$, $CR^{100}R^{101}$, or $C(R^{100})V^8Z^8$; E is O or S; $G^1$ is hydrogen, alkyl, acyl, silyl, phosphate, or L-T; $Y^1, Y^2, Y^3, Y^4, Y^5, Y^6$ and $Y^7$ independently are O, S or $NJ^2$; $V^1, V^2, V^3, V^4, V^5, V^6, V^7$ and $V^8$ independently are O, S or $NJ^3$; $CR^{102}R^{103}$, or a direct bond; $Z^1, Z^2, Z^3, Z^4, Z^5, Z^7$ and $Z^8$ independently are $R^{104}$ or L-T; each L is independently a direct bond or the residue of a multivalent moiety that does not significantly impair the ability of the compound to bind transcobalamin or intrinsic factor proteins; each T independently comprises the residue of one or more radionuclides; at least one of $Z^2, Z^4$, or $Z^5$ comprises a radionuclide, the remaining Z moieties retaining their natural vitamin $B_{12}$ configuration; $J^1, J^2$ and $J^3$ independently are hydrogen, alkyl, alkenyl, alkynyl, alkaryl, cycloalkyl, aryl, cycloaryl, heterocycle, heteroaryl, hydroxyl, alkoxy, or amine; $R^1, R^2, R^3, R^4, R^5, R^6, R^7, R^8, R^9, R^{10}, R^{11}, R^{12}, R^{13}, R^{14}$ and $R^{15}$ independently are hydrogen, lower alkyl, lower alkenyl, lower alkynyl, lower cycloalkyl, heterocyclic, lower alkoxy, azido, amino, lower alkylamino, halogen, thiol, $SO_2$, $SO_3$, carboxylic acid, $C_{1-4}$ carboxyl, hydroxyl, nitro, cyano, oxime or hydrazine; $R^{13}$ and $R^{14}$ optionally can come together to form a double bond; and $R^{100}, R^{101}, R^{102}, R^{103}$, and $R^{104}$ are independently hydrogen, alkyl, alkenyl, alkynyl, hydroxyl, alkoxy, cyano, azido, halogen, nitro, $SO_2$, $SO_3$, thioalkyl, or amino.

Subembodiment 4: X is hydrogen, cyano, amino, amido, hydroxyl, 5'-deoxyadenosyl, L-T, alkyl, alkenyl, alkynyl, cycloalkyl, aryl, aralkyl, heterocycle, or heteroaryl, or alkylheteroaryl; M, K, E and $G^1$ retain their natural vitamin $B_{12}$ configuration; $Y^1, Y^2, Y^3, Y^4, Y^5, Y^6$ and $Y^7$ independently are O, S or $NJ^2$; $V^1, V^2, V^3, V^4, V^5, V^6, V^7$ and $V^8$ independently are O, S or $NJ^3$; $CR^{102}R^{103}$, or a direct bond; $Z^1, Z^2, Z^3, Z^4, Z^5, Z^7$ and $Z^8$ independently are $R^{104}$ or L-T; each L is independently a direct bond or the residue of a multivalent moiety that does not significantly impair the ability of the compound to bind transcobalamin or intrinsic factor proteins; each L is independently a direct bond or the residue of a multivalent moiety that does not significantly impair the ability of the compound to bind transcobalamin or intrinsic factor proteins; each T independently comprises the residue of one or more radionuclides; at least one of $Z^1, Z^2, Z^3, Z^4, Z^5, Z^7, Z^8$, M, K, and $G^1$ comprises a radionuclide; $J^2$ and $J^3$ independently are hydrogen, alkyl, alkenyl, alkynyl, alkaryl, cycloalkyl, aryl, cycloaryl, heterocycle, heteroaryl, hydroxyl, alkoxy, or amine; $R^1, R^2, R^3, R^4, R^5, R^6, R^7, R^8, R^9, R^{10}, R^{11}, R^{12}, R^{13}, R^{14}$ and $R^{15}$ retain their natural vitamin $B_{12}$ configuration; and $R^{100}, R^{101}, R^{102}, R^{103}$, and $R^{104}$ are independently hydrogen, alkyl, alkenyl, alkynyl, hydroxyl, alkoxy, cyano, azido, halogen, nitro, $SO_2$, $SO_3$, thioalkyl, or amino.

Subembodiment 5: X is hydrogen, cyano, amino, amido, hydroxyl, 5'-deoxyadenosyl, L-T, alkyl, alkenyl, alkynyl, cycloalkyl, aryl, aralkyl, heterocycle, or heteroaryl, or alkylheteroaryl; M, K, E and $G^1$ retain their natural vitamin $B_{12}$ configuration; $Y^1, Y^2, Y^3, Y^4, Y^5, Y^6$ and $Y^7$ independently are O, S or $NJ^2$; $V^1, V^2, V^3, V^4, V^5, V^6, V^7$ and $V^8$ independently are O, S or $NJ^3$; $CR^{102}R^{103}$, or a direct bond; $Z^1, Z^2, Z^3, Z^4, Z^5, Z^7$ and $Z^8$ independently are $R^{104}$ or L-T; each L is independently a direct bond or the residue of a multivalent moiety that does not significantly impair the ability of the compound to bind transcobalamin or intrinsic factor proteins; each L is independently a direct bond or the residue of a multivalent moiety that does not significantly impair the ability of the compound to bind transcobalamin or intrinsic factor proteins; each T independently comprises the residue of one or more radionuclides; at least one of $Z^2, Z^4$, or $Z^5$ comprises a radionuclide, the remaining Z moieties retaining their natural vitamin $B_{12}$ configuration; $J^1, J^2$ and $J^3$ independently are hydrogen, alkyl, alkenyl, alkynyl, alkaryl, cycloalkyl, aryl, cycloaryl, heterocycle, heteroaryl, hydroxyl, alkoxy, or amine; $R^1, R^2, R^3, R^4, R^5, R^6, R^7, R^8, R^9, R^{10}, R^{11}, R^{12}, R^{13}, R^{14}$ and $R^{15}$ independently are hydrogen, lower alkyl, lower alkenyl, lower alkynyl, lower cycloalkyl, heterocyclic, lower alkoxy, azido, amino, lower alkylamino, halogen, thiol, $SO_2$, $SO_3$, carboxylic acid, $C_{1-6}$ carboxyl, hydroxyl, nitro, cyano, oxime or hydrazine; $R^{13}$ and $R^{14}$ optionally can come together to form a double bond; and $R^{100}, R^{101}, R^{102}, R^{103}$, and $R^{104}$ are independently hydrogen, alkyl, alkenyl, alkynyl, hydroxyl, alkoxy, cyano, azido, halogen, nitro, $SO_2$, $SO_3$, thioalkyl, or amino.

Subembodiment 6: X is hydrogen, cyano, amino, amido, hydroxyl, 5'-deoxyadenosyl, L-T, alkyl, alkenyl, alkynyl, cycloalkyl, aryl, aralkyl, heterocycle, or heteroaryl, or alkyl-heteroaryl; M, K, E and $G^1$ retain their natural vitamin $B_{12}$ configuration; $Y^1, Y^2, Y^3, Y^4, Y^5, Y^6$ and $Y^7$ independently are O, S or $NJ^2$; $V^1, V^2, V^3, V^4, V^5, V^6, V^7$ and $V^8$ independently are O, S or $NJ^3$; $CR^{102}R^{103}$, or a direct bond; $Z^1, Z^2, Z^3, Z^4, Z^5, Z^7$ and $Z^8$ independently are $R^{104}$ or L-T; each L is independently a direct bond or the residue of a multivalent moiety that does not significantly impair the ability of the compound to bind transcobalamin or intrinsic factor proteins; each L is independently a direct bond or the residue of a multivalent moiety that does not significantly impair the ability of the compound to bind transcobalamin or intrinsic factor proteins; each T independently comprises the residue of one or more radionuclides; at least one of $Z^2, Z^4$, or $Z^5$ comprises a radionuclide, the remaining Z moieties retaining their natural vitamin $B_{12}$ configuration; $J^1, J^2$ and $J^3$ independently are hydrogen, alkyl, alkenyl, alkynyl, alkaryl, cycloalkyl, aryl, cycloaryl, heterocycle, heteroaryl, hydroxyl, alkoxy, or amine; $R^1, R^2, R^3, R^4, R^5, R^6, R^7, R^8, R^9, R^{10}, R^{11}, R^{12}, R^{13}, R^{14}$ and $R^{15}$ independently are hydrogen, lower alkyl, lower alkenyl, lower alkynyl, lower cycloalkyl, heterocyclic, lower alkoxy, azido, amino, lower alkylamino, halogen, thiol, $SO_2$, $SO_3$, carboxylic acid, $C_{1-6}$ carboxyl, hydroxyl, nitro, cyano, oxime or hydrazine; $R^{13}$ and $R^{14}$ optionally can come together to form a double bond; and $R^{100}, R^{101}, R^{102}, R^{103}$ and $R^{104}$ are independently hydrogen, alkyl, alkenyl, alkynyl, hydroxyl, alkoxy, cyano, azido, halogen, nitro, $SO_2$, $SO_3$, thioalkyl, or amino.

Subembodiment 7: X is 5'-deoxyadenosyl; M, K, E and $G^1$ retain their natural vitamin $B_{12}$ configuration; $Y^1, Y^2, Y^3, Y^4, Y^5, Y^6$ and $Y^7$ independently are O, S or $NJ^2$; $V^1, V^2, V^3, V^4, V^5, V^6, V^7$ and $V^8$ independently are O, S or $NJ^3$; $CR^{102}R^{103}$, or a direct bond; $Z^1, Z^2, Z^3, Z^4, Z^5, Z^7$ and $Z^8$ independently are $R^{104}$ or L-T; each L is independently a direct bond or the residue of a multivalent moiety that does not significantly impair the ability of the compound to bind transcobalamin or intrinsic factor proteins; each L is independently a direct bond or the residue of a multivalent moiety that does not significantly impair the ability of the compound to bind transcobalamin or intrinsic factor proteins; each T independently comprises the residue of one or more radionuclides; at least one of $Z^1, Z^2, Z^3, Z^4, Z^5, Z^7, Z^8$, M, K, and $G^1$ comprises a radionuclide; $J^2$ and $J^3$ independently are hydrogen, alkyl, alkenyl, alkynyl, alkaryl, cycloalkyl, aryl, cycloaryl, heterocycle, heteroaryl, hydroxyl, alkoxy, or amine; $R^1, R^2, R^3, R^4, R^5, R^6, R^7, R^8, R^9, R^{10}, R^{11}, R^{12}, R^{13}, R^{14}$ and $R^{15}$ retain their natural vitamin $B_{12}$ configuration; and $R^{100}, R^{101}, R^{102}, R^{103}$, and $R^{104}$ are independently hydrogen, alkyl, alkenyl, alkynyl, hydroxyl, alkoxy, cyano, azido, halogen, nitro, $SO_2$, $SO_3$, thioalkyl, or amino.

Subembodiment 8: X is 5'-deoxyadenosyl; M, K, E, and $G^1$ retain their natural vitamin $B_{12}$ configuration; $Y^1, Y^2, Y^3, Y^4, Y^5, Y^6$ and $Y^7$ independently are O, S or $NJ^2$; $V^1, V^2, V^3, V^4, V^5, V^6, V^7$ and $V^8$ independently are O, S or $NJ^3$; $CR^{102}R^{103}$, or a direct bond; $Z^1, Z^2, Z^3, Z^4, Z^5, Z^7$ and $Z^8$ independently are $R^{104}$ or L-T; each L is independently a direct bond or the residue of a multivalent moiety that does not significantly impair the ability of the compound to bind transcobalamin or intrinsic factor proteins; each L is independently a direct bond or the residue of a multivalent moiety that does not significantly impair the ability of the compound to bind transcobalamin or intrinsic factor proteins; each T independently comprises the residue of one or more radionuclides; at least one of $Z^2, Z^4$, or $Z^5$ comprises a radionuclide, the remaining Z moieties retaining their natural vitamin $B_{12}$ configuration; $J^1, J^2$ and $J^3$ independently are hydrogen, alkyl, alkenyl, alkynyl, alkaryl, cycloalkyl, aryl, cycloaryl, heterocycle, heteroaryl, hydroxyl, alkoxy, or amine; $R^1, R^2, R^3, R^4, R^5, R^6, R^7, R^8, R^9, R^{10}, R^{11}, R^{12}, R^{13}, R^{14}$ and $R^{15}$ independently are hydrogen, lower alkyl, lower alkenyl, lower alkynyl, lower cycloalkyl, heterocyclic, lower alkoxy, azido, amino, lower alkylamino, halogen, thiol, $SO_2$, $SO_3$, carboxylic acid, $C_{1-6}$ carboxyl, hydroxyl, nitro, cyano, oxime or hydrazine; $R^{13}$ and $R^{14}$ optionally can come together to form a double bond; and $R^{100}R^{101}, R^{102}, R^{103}$, and $R^{104}$ are independently hydrogen, alkyl, alkenyl, alkynyl, hydroxyl, alkoxy, cyano, azido, halogen, nitro, $SO_2$, $SO_3$, thioalkyl, or amino.

Subembodiment 9: X is hydrogen, cyano, amino, amido, hydroxyl, 5'-deoxyadenosyl, L-T, alkyl, alkenyl, alkynyl, cycloalkyl, aryl, aralkyl, heterocycle, or heteroaryl, or alkyl-heteroaryl; M, K, E, and $G^1$ retain their natural vitamin $B_{12}$ configuration; $Y^1, Y^2, Y^3, Y^5, Y^6$ and $Y^7$ independently are O, S or $NJ^2$; $V^1, V^2, V^3, V^4, V^5, V^6, V^7$ and $V^8$ independently are O, S or $NJ^3$; $CR^{102}R^{103}$, or a direct bond; $Z^1, Z^2, Z^3, Z^4, Z^5, Z^7$ and $Z^8$ independently are $R^{104}$ or L-T; each L is independently a direct bond or the residue of a multivalent moiety that does not significantly impair the ability of the compound to bind transcobalamin or intrinsic factor proteins; each L is independently a direct bond or the residue of a multivalent moiety that does not significantly impair the ability of the compound to bind transcobalamin or intrinsic factor proteins; each T independently comprises the residue of one or more radionuclides; at least one of $Z^2, Z^4$, or $Z^5$ comprises a radionuclide, the remaining Z moieties retaining their natural vitamin $B_{12}$ configuration; $J^1, J^2$ and $J^3$ independently are hydrogen, alkyl, alkenyl, alkynyl, alkaryl, cycloalkyl, aryl, cycloaryl, heterocycle, heteroaryl, hydroxyl, alkoxy, or amine; $R^1, R^2, R^3, R^4, R^5, R^6, R^7, R^8, R^9, R^{10}, R^{11}, R^{12}, R^{13}, R^{14}$ and $R^{15}$ all retain their natural vitamin $B_{12}$ configuration; and $R^{100}, R^{101}, R^{102}, R^{103}$, and $R^{104}$ are independently hydrogen, alkyl, alkenyl, alkynyl, hydroxyl, alkoxy, cyano, azido, halogen, nitro, $SO_2$, $SO_3$, thioalkyl, or amino.

Subembodiment 10: X is 5'-deoxyadenosyl; M, K, E, and $G^1$ retain their natural vitamin $B_{12}$ configuration; $Y^1, Y^2, Y^3, Y^4, Y^5, Y^6$ and $Y^7$ independently are O, S or $NJ^2$, $V^1, V^2, V^3, V^4, V^5, V^6, V^7$ and $V^8$ independently are O, S or $NJ^3$; $CR^{102}R^{103}$, or a direct bond; $Z^1, Z^2, Z^3, Z^4, Z^5, Z^7$ and $Z^8$ independently are $R^{104}$ or L-T; each L is independently a direct bond or the residue of a multivalent moiety that does not significantly impair the ability of the compound to bind transcobalamin or intrinsic factor proteins; each L is independently a direct bond or the residue of a multivalent moiety that does not significantly impair the ability of the compound to bind transcobalamin or intrinsic factor proteins; each T independently comprises the residue of one or more radionuclides; at least one of $Z^2, Z^4$, or $Z^5$ comprises a radionuclide, the remaining Z moieties retaining their natural vitamin $B_{12}$ configuration; $J^1, J^2$ and $J^3$ independently are hydrogen, alkyl, alkenyl, alkynyl, alkaryl, cycloalkyl, aryl, cycloaryl, heterocycle, heteroaryl, hydroxyl, alkoxy, or amine; $R^1, R^2, R^3, R^4$, $R^5$, $R^6$, $R^7$, $R^8$, $R^9$, $R^{10}$, $R^{11}$, $R^{12}$, $R^{13}$, $R^{14}$ and $R^{15}$ all retain their natural vitamin $B_{12}$ configuration; and $R^{100}$, $R^{101}$, $R^{102}$, $R^{103}$ and $R^{104}$ are independently hydrogen, alkyl, alkenyl, alkynyl, hydroxyl, alkoxy, cyano, azido, halogen, nitro, $SO_2$, $SO_3$, thioalkyl, or amino.

III. Linkers

The TC- or IF-binding carrier and therapeutic and/or diagnostic agent useful to treat and/or image sites of proliferative disease in the body, such as cancerous tumors, can be combined by means of a di- or multi-valent linking moiety. The linker used to join the TC binding carrier and the therapeutic and/or diagnostic agent preferably has a single molecular weight, and does not exhibit a molecular weight distribution, for example as found in most polymers. The linker can range in size from small to large molecular weight, as long as there is not a distribution of weights in the linker. It is important to strictly control the uniformity of size of the conjugate for predictability of therapeutic performance.

The linkers preferably have a molecular weight below about 2000, more preferably below about 1000, and even more preferably below about 500.

As noted above, L is the residue of a linker molecule that conjugates one or more therapeutic and/or diagnostic agents to the TC or IF-binding carrier. The structure of the linker from which L is derived (in any one of the $Z^1$, $Z^2$, $Z^3$, $Z^4$, $Z^5$, $Z^6$, $Z^7$, X, M, K or $G^1$ moieties) is not crucial, provided it does not significantly impair the ability of the conjugate to bind to the transcobalamin or IF transport protein or receptor. L is preferably any multivalent molecule (divalent or greater) that does not significantly impair the ability of the TC carrier to bind to the transcobalamin transport protein or receptor. The ability of vitamin $B_{12}$ or any other TC-binding carrier to bind to the transcobalamin transport protein or receptor is "significantly impaired" when attaching a linking moiety to the $B_{12}$ or TC-binding carrier lessens the affinity of the vitamin $B_{12}$ or the TC-binding carrier for the transcobalamin transport protein to which the vitamin $B_{12}$ or TC-binding carrier is most readily bound by 50% or more. The unsaturated vitamin $B_{12}$ binding capacity (UBBC) assay described by D. A. Collins and H. P. C. Hogenkamp in *J. Nuclear Medicine*, 1997, 38, 717-723 can be used to compare the relative affinities of ligands for this receptor.

In one embodiment the linker is of precise molecular weight and does not posses a molecular weight distribution. In one embodiment, the linker has a molecular weight less than about 2,500, 2,000, 1900, 1800, 1,500, 1,000 or 500.

A particularly preferred linker is one having multiple sites for conjugation to one or more therapeutic and/or diagnostic agents, wherein the linker has a unimodal molecular weight. Recombinant protein production techniques can be employed to obtain poly(amino acid) linkers of substantially constant molecular weight.

In one embodiment the linker is an amino acid, or a polymer or peptide formed from a plurality of amino acids. The polymer or peptide can be derived from one or more amino acids. The amino acid, poly(amino acid) or peptide can link T to V through the carboxy terminus or the amino terminus. The amino acid residue, peptide residue, or poly(amino acid) residue can conveniently be linked to V and T through an amide (e.g., —N(R)C(=O)— or —C(=O)N(R)—), ester (e.g., —OC(=O)— or —C(=O)O—), ether (e.g., —O—), ketone (e.g., —C(=O)—), thioether (e.g., —S—), sulfinyl (e.g., —S(O)—), sulfonyl (e.g., —S(O)$_2$—), or a direct (e.g., C—C bond) linkage, wherein each R is independently H or ($C_1$-$C_{14}$) alkyl.

Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right, but are meant to also include the opposite flow. Particularly suitable peptides and poly(amino acids) comprise from 2 to about 20 amino acids, from 2 to about 15 amino acids, or from 2 to about 12 amino acids.

One exemplary poly(amino acid) is poly-L-lysine ((—NHCH(($CH_2$)$_4$—$NH_2$)CO—)$_m$-Q, wherein Q is H, ($C_1$-$C_{14}$)alkyl, or a suitable carboxy protecting group, and m is from 2 to about 20, from about 5 to about 15, or from about 8 to about 11. The polylysine offers multiple primary amine sites to which anti-proliferative agents can be readily attached. Alternatively, the linkers can be formed with multiple cysteines, to provide free thiols, or multiple glutamates or aspartates, to provide free carboxyls for conjugation using suitable carbodiimides. Similarly the linker can contain multiple histidines or tyrosines for conjugation. Other exemplary poly(amino acid) linkers are poly-L-glutamic acid, poly-L-aspartic acid, poly-L-histidine, poly-L-ornithine, poly-L-serine, poly-L-threonine, poly-L-tyrosine, poly-L-lysine-L-phenylalanine or poly-L-lysine-L-tyrosine. When the linker is derived from a poly(amino acid) other than polylysine, the linker is, in a series of embodiments, prepared from 2 to about 30 amino acids, 5 to about 20 amino acids, or 8 to about 15 amino acids.

In another particular embodiment L is a polyamine residue (having at least three amino moieties) of the following chemical structure: NR'(alkylene-NR')$_n$alkyleneNR', wherein n is from 1 to 20, the carbon length of alkylene can vary within the n units, and each R' is independently hydrogen, lower alkyl, or T. N is preferably from 1 to 10. Moreover, L preferably has a backbone along its longest length of no more than 100, 75, 50, 40, 30, 20 or 15 atoms. Exemplary polyamines from which L can be derived include spermine ($H_2N(CH_2)_3NH(CH_2)_4NH(CH_2)_3NH_2$), spermidine ($H_2N(CH_2)_3NH(CH_2)_4NH_2$), decamethylene tetraamine, and pentamethylene hexamine. These linkers are a definite size and thus provide consistent and predictable targeting by the cobalamin conjugate, in addition to multiple binding sites for the therapeutic and/or diagnostic agent.

In another embodiment L is a diamine represented by the formula $NH_2$ ($CH_2$)$_x$ $NH_2$, in which x is 2-20, and preferably 2-12. Thus, the linker can be prepared from 1,6-diaminohexane, 1,5-diaminopentane, 1,4-diaminobutane and 1,3-diaminopropane.

Other suitable linkers are formed from the covalent linkage of various water soluble molecules with amino acids, peptides, poly(amino acids), polyamines, polyoxyalkylenes, polyanhydrides, polyesters, polyamides, polyglycolides and diamines. Suitable water soluble molecules include, for example, polyethylene glycol, and dicarboxylic monosaccharides such as glucaric acid, galactaric acid and xylaric acid.

Other suitable linkers include those represented by the formula HO(O)C($CH_2$)$_x$C(O)OH, in which x is 2-20, and preferably 2-12. Thus, the linker can be prepared from succinic acid, glutaric acid, adipic acid, suberic acid, sebacic acid, azelaic acid or maleic acid. Still other suitable linkers comprise carboxylic acid derivatives that yield an amide upon reaction with an amine. Such reactive groups include, by way of example, carboxylic acid halides such as acid chlorides and bromides; carboxylic acid anhydrides such as acetic anhydrides and trifluoroacetic anhydrides; esters such as p-nitrophenyl esters and N-hydroxysuccinimide esters; and imidazolides. Techniques for using such linkers are described in detail in Bodanszky, Principles of Peptide Synthesis, Springer Verlag, Berlin, 1984.

In one embodiment, the linker is modified to facilitate its conjugation either to V and/or T. Suitable molecules for modifying the linker include: disuccinimidyl suberate (DSS), bis (sulfosuccinimidyl)suberate (BSS), ethylene glycolbis(succinimidylsuccinate) (EGS), ethylene glycolbis (sulfosuccinimidyl-succinate) (Sulfo-EGS), p-aminophenylacetic acid, dithiobis(succinimidyl-propionate) (DSP), 3,3'-dithiobis-(sulfosuccinimidyl-propionate) (DTSSP), disuccinimidyl tartarate (DST), disulfosuccinimidyl tartarate (Sulfo-DST), bis(2-(succinimidooxycarbonyloxy)-ethylene) sulfone (BSOCOES), bis(2-(sulfo-succinimidooxycarbonyloxy)-ethylene)sulfone (Sulfo-BSOCOES), dimethyl adipimidate 2HCl (DMA), dimethyl pimelimidate 2HCl (DMP), and dimethyl suberimidate 2HCl (DMS).

In a particular embodiment, nonmetallic radioisotopes can conveniently be linked to the vitamin $B_{12}$ structure through a residue of a peptide having the following formula:

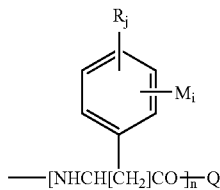

wherein each M is independently a non-metallic radionuclide; each R is independently $(C_1-C_{14})$alkyl, $(C_2-C_{14})$alkenyl, $(C_2-C_{14})$alkynyl, $(C_1-C_{14})$alkoxy, hydroxy, cyano, nitro, halo, trifluoromethyl, $N(R_a)(R_b)$, $(C_1-C_{14})$alkanoyl, $(C_2-C_{14})$alkanoyloxy, $(C_6-C_{10})$aryl, or $(C_3-C_8)$cycloalkyl wherein $R_a$ and $R_b$ are each independently H or $(C_1-C_{14})$ alkyl; P; Q is H, $(C_1-C_{14})$alkyl, or a suitable carboxy protecting group; n is 2 to about 20; I is 1-5, j is 0-4 and I+j is $\leq 5$; or a pharmaceutically acceptable salt thereof. Specifically, i can be 1, j can be 0, M can be a positron emitter such as Fluorine-18, Bromine-76 or Iodine-124, or a gamma emitter such as Iodine-123 or Iodine-131, and n can be about 6 to about 12.

Biodegradable Linkers

Various degradable linkers can be used to link the TC-binding or IF-binding moiety to the antiproliferative agent. The desired linkers can degrade under biological conditions such as by enzymatic cleavage or by systemic pH or temperature. Alternatively, these linkers can be induced to degrade by external manipulation such as changes in pH, temperature, ultrasound, magnetic field, radiation (i.e. UV radiation) or light.

U.S. Pat. No. 5,639,885 entitled "Redox amino acids and peptides containing them;" U.S. Pat. No. 5,637,601 entitled "Anticholinergic compounds, compositions and methods of treatment;" U.S. Pat. No. 5,624,894 entitled "Brain-enhanced delivery of neuroactive peptides by sequential metabolism;" U.S. Pat. No. 5,618,826 entitled "Anticholinergic compounds, compositions and methods of treatment;" U.S. Pat. No. 5,618,803 entitled "Targeted drug delivery via phosphonate derivatives;" U.S. Pat. No. 5,610,188 entitled "Anticholinergic compounds, compositions and methods of treatment;" U.S. Pat. No. 5,525,727 entitled "Brain-specific drug delivery;" U.S. Pat. No. 5,418,244 entitled "Anticholinergic compounds, compositions and methods of treatment;" U.S. Pat. No. 5,413,996 entitled "Targeted drug delivery via phosphonate derivatives;" U.S. Pat. No. 5,389,623 entitled "Redox carriers for brain-specific drug delivery;" U.S. Pat. No. 5,296,483 entitled "Brain-specific analogues of centrally acting amines;" U.S. Pat. No. 5,258,388 entitled "Anticholinergic compounds, compositions and methods of treatment;" U.S. Pat. No. 5,231,089 entitled "Method of improving oral bioavailability of carbamazepine;" U.S. Pat. No. 5,223,528 entitled "Anticholinergic compounds, compositions and methods of treatment;" U.S. Pat. No. 5,187,158 Brain-specific drug delivery;" U.S. Pat. No. 5,177,064 entitled "Targeted drug delivery via phosphonate derivatives;" U.S. Pat. No. 5,155,227 entitled "Compounds for site-enhanced delivery of radionuclides;" U.S. Pat. No. 5,136,038 entitled "Radiopharmaceuticals and chelating agents useful in their preparation;" U.S. Pat. No. 5,087,618 entitled "Redox carriers for brain-specific drug delivery;" U.S. Pat. No. 5,079,366 entitled "Quaternary pyridinium salts;" U.S. Pat. No. 5,053,215 entitled "NMR-assayable ligand-labeled trifluorothymidine containing composition and method for diagnosis of HSV infection;" U.S. Pat. No. 5,024,998 entitled "Pharmaceutical formulations for parenteral use;" U.S. Pat. No. 5,017,618 entitled "Labile derivatives of ketone analogs of 3-substituted-1-alkylamino-2-propanols and their use as beta-adrenergic blockers;" U.S. Pat. No. 5,017,566 entitled "Redox systems for brain-targeted drug delivery;" U.S. Pat. No. 5,008,257 entitled "Brain-specific drug delivery;" U.S. Pat. No. 5,002,935 entitled "Improvements in redox systems for brain-targeted drug delivery;" U.S. Pat. No. 4,983,586 entitled "Pharmaceutical formulations for parenteral use;" U.S. Pat. No. 4,963,688 entitled "Compounds for site-enhanced delivery of radionuclides and uses thereof;" U.S. Pat. No. 4,963,682 entitled "Novel radiopharmaceuticals and chelating agents useful in their preparation;" U.S. Pat. No. 4,933,438 entitled "Brain-specific analogues of centrally acting amines;" U.S. Pat. No. 4,900,837 entitled "Brain-specific drug delivery of steroid sex hormones cleaved from pyridinium carboxylates and dihydro-pyridine carboxylate precursors;" U.S. Pat. No. 4,892,737 entitled "Composition and method for enhancing permeability of topical drugs;" U.S. Pat. No. 4,888,427 entitled "Amino acids containing dihydropyridine ring systems for site-specific delivery of peptides to the brain;" U.S. Pat. No. 4,880,921 entitled "Brain-specific drug delivery;" 35. U.S. Pat. No. 4,863,911 entitled "Method for treating male sexual dysfunction;" U.S. Pat. No. 4,829,070 entitled "Novel redox carriers for brain-specific drug delivery;" U.S. Pat. No. 4,824,850 entitled "Brain-specific drug delivery;" U.S. Pat. No. 4,801,597 entitled "Certain inositol-nicotinate ester derivatives and polyionic complexes therefore useful for treating diabetes meuitus, hyperlipidemia and lactic acidosis;" U.S. Pat. No. 4,771,059 entitled "Brain-specific analogues of centrally acting amines;" U.S. Pat. No. 4,727,079 entitled "Brain-specific dopaminergic activity involving dihydropyridine carboxamides, dihydroquinoline and isoquinoline carboxamides;" U.S. Pat. No. 4,540,564 entitled "Brain-specific drug delivery;" and U.S. Pat. No. 4,479,932 entitled "Brain-specific drug delivery" to Nicholas S. Bodor, et al., disclose several biodegradable linkers that target the brain. For example, a lipoidal form of dihydropyridine pyridinium salt redox carrier, DHC, linked to a centrally acting drug which can be reduced and biooxidized to pass through the blood brain barrier. The dihydropyridine nucleus readily and easily penetrates the blood brain barrier in increased concentrations; furthermore, the in vivo oxidation of the dihydropyridine moiety to the ionic pyridinium salts thereby prevents its elimination from the brain, while elimination from the general circulation is accelerated, resulting in a prolongedly sustained brain-specific drug activity.

This dihydropyridine can be incorporated into the linkers set forth above for biodegradation.

Additionally U.S. Pat. No. 4,622,218 entitled "Testicular-specific drug delivery," discloses linkers that can specifically deliver drugs to the testes in much the same manner, and which can be used in the linkers of the present invention. The lipoidal form [D-DHC] of a dihydropyridine pyridinium salt redox carrier, e.g. 1,4-dihydrotrigonelline, penetrates the blood-testis barrier. Oxidation of the dihydropyridine carrier moiety in vivo to the ionic pyridinium salt type drug/carrier entity $[D-QC]^+$ prevents elimination thereof from the testes, while elimination from the general circulation is accelerated, resulting in significant and prolongedly sustained testicular-specific drug activity.

Margerum, et al. in U.S. Pat. No. 5,976,493 discloses the use of polychelant compounds which are degradable in vivo to release excretable fragments for diagnostic imaging which also are suitable in the linkers of the present invention. These compounds contain a linker moiety which is metabolically cleavable to release macrocyclic monochelant fragments, wherein the macrocyclic skeleton preferably has 9 to 25 ring members, and a biotolerable polymer, preferably a substantially monodisperse polymer. Other suitable linkers are disclosed, for example, in Krejcarek et al. (Biochemical and Biophysical Research Communications 77: 581 (1977)) (mixed anhydrides), Hnatowich et al. (Science 220: 613 (1983))(cyclic anhydrides), U.S. Pat. No. 5,637,684 to Cook, et al. (Phosphoramidate and phosphorothioamidate oligomeric compounds).

Other suitable biodegradable polymers from which the linker can be formed are the polyanhydrides and polyorthoesters, which take advantage of labile backbone linkages (see: Domb et al. *Macromolecules*, 22, 3200, 1989; and Heller et al. *Biodegradable Polymers as Drug Delivery Systems*, Dekker, NY: 1990). Other linker materials include hydrogels, such as the PEG-oligoglycolyl-acrylates disclosed in U.S. Pat. No. 5,626,863 to Hubbell et al. Other biodegradable linkers are formed from oligoglycolic acid is a poly(a-hydroxy acid), polylactic acid, polycaprolactone, polyorthoesters, polyanhydrides and polypeptides.

Nonlimiting examples of U.S. Patents that describe controlled release formulations suitable for use as linking agents are: U.S. Pat. No. 5,356,630 to Laurencin et al. (Delivery System for Controlled Release of Bioactive Factors); U.S. Pat. No. 5,797,898 to Santini, Jr. et al. (Microchip Drug Delivery Devices); U.S. Pat. No. 5,874,064 to Edwards et al. (Aerodynamically Light Particles for Pulmonary Drug Delivery); U.S. Pat. No. 5,548,035 to Kim et al. (Biodegradable Copolymer as Drug Delivery Matrix Comprising Polyethyleneoxide and Aliphatic Polyester Blocks); U.S. Pat. No. 5,532,287 to Savage et al. (Radiation Cured Drug Release Controlling Membrane); U.S. Pat. No. 5,284,831 to Kahl et al. (Drug Delivery Porphyrin Composition and Methods); U.S. Pat. No. 5,741,329 to Agrawal et al. (Methods of Controlling the pH in the Vicinity of Biodegradable Implants); U.S. Pat. No. 5,820,883 to Tice et al. (Methods for Delivering Bioactive Agents into and Through the Mucosally-Associated Lymphoid Tissues and Controlling Their Release); U.S. Pat. No. 5,955,068 to Gouin et al. (Biodegradable Polyanhydrides Derived from Dimers of Bile Acids, and Use Thereof as Controlled Drug Release Systems); U.S. Pat. No. 6,001,395 to Coombes et al. (Polymeric Lamellar Substrate Particles for Drug Delivery); U.S. Pat. No. 6,013,853 to Athanasiou et al. (Continuous Release Polymeric Implant Carriers); U.S. Pat. No. 6,060,582 to Hubbell et al. (Photopolymerizable Biodegradable Hydrogels as Tissue Contacting Materials and Controlled Release Carriers); U.S. Pat. No. 6,113,943 to Okada et al. (Sustained-Release Preparation Capable of Releasing a Physiologically Active Substance); and PCT Publication No. WO 99/59548 to Oh et al. (Controlled Drug Delivery System Using the Conjugation of Drug to Biodegradable Polyester); U.S. Pat. No. 6,123,861 (Fabrication of Microchip Drug Delivery Devices); U.S. Pat. No. 6,060,082 (Polymerized Liposomes Targeted to M cells and Useful for Oral or Mucosal Drug Delivery); U.S. Pat. No. 6,041,253 (Effect of Electric Field and Ultrasound for Transdermal Drug Delivery); U.S. Pat. No. 6,018,678 (Transdermal protein delivery or measurement using low-frequency sonophoresis); U.S. Pat. No. 6,007,845 Nanoparticles And Microparticles Of Non-Linear Hydrophilic-Hydrophobic Multiblock Copolymers; U.S. Pat. No. 6,004,534 Targeted Polymerized Liposomes For Improved Drug Delivery; U.S. Pat. No. 6,002,961 Transdermal Protein Delivery Using Low-Frequency Sonophoresis; U.S. Pat. No. 5,985,309 Preparation Of Particles For Inhalation; U.S. Pat. No. 5,947,921 Chemical And Physical Enhancers And Ultrasound For Transdermal Drug Delivery; U.S. Pat. No. 5,912,017 Multiwall Polymeric Microspheres; U.S. Pat. No. 5,911,223 Introduction Of Modifying Agents Into Skin By Electroporation; U.S. Pat. No. 5,874,064 Aerodynamically Light Particles For Pulmonary Drug Delivery; U.S. Pat. No. 5,855,913 Particles Incorporating Surfactants For Pulmonary Drug Delivery; U.S. Pat. No. 5,846,565 Controlled Local Delivery Of Chemotherapeutic Agents For Treating Solid Tumors; U.S. Pat. No. 5,837,752 Semi-Interpenetrating Polymer Networks; U.S. Pat. No. 5,814,599 Transdermal Delivery Of Encapsulated Drugs; U.S. Pat. No. 5,804,178 Implantation Of Cell-Matrix Structure Adjacent Mesentery, Omentum Or Peritoneum Tissue; U.S. Pat. No. 5,797,898 Microchip Drug Delivery Devices; U.S. Pat. No. 5,770,417 Three-Dimensional Fibrous Scaffold Containing Attached Cells For Producing Vascularized Tissue In Vivo; U.S. Pat. No. 5,770,193 Preparation Of Three-Dimensional Fibrous Scaffold For Attaching Cells To Produce Vascularized Tissue In Vivo; U.S. Pat. No. 5,762,904 Oral Delivery Of Vaccines Using Polymerized Liposomes; U.S. Pat. No. 5,759,830 Three-Dimensional Fibrous Scaffold Containing Attached Cells For Producing Vascularized Tissue In Vivo; U.S. Pat. No. 5,749,847 Delivery Of Nucleotides Into Organisms By Electroporation; U.S. Pat. No. 5,736,372 Biodegradable Synthetic Polymeric Fibrous Matrix Containing Chondrocyte For In Vivo Production Of A Cartilaginous Structure; U.S. Pat. No. 5,718,921 Microspheres Comprising Polymer And Drug Dispersed There Within; U.S. Pat. No. 5,696,175 Preparation Of Bonded Fiber Structures For Cell Implantation; U.S. Pat. No. 5,667,491 Method For Rapid Temporal Control Of Molecular Transport Across Tissue; U.S. Pat. No. 5,654,381 Functionalized Polyester Graft Copolymers; U.S. Pat. No. 5,651,986 Controlled Local Delivery Of Chemotherapeutic Agents For Treating Solid Tumors; U.S. Pat. No. 5,629,009 Delivery System For Controlled Release Of Bioactive Factors; U.S. Pat. No. 5,626,862 Controlled Local Delivery Of Chemotherapeutic Agents For Treating Solid Tumors; U.S. Pat. No. 5,593,974 Localized Oligonucleotide Therapy; U.S. Pat. No. 5,578,325 Nanoparticles And Microparticles Of Non-Linear Hydrophilic-Hydrophobic Multiblock Copolymers; U.S. Pat. No. 5,562,099 Polymeric Microparticles Containing Agents For Imaging; U.S. Pat. No. 5,545,409 Delivery System For Controlled Release Of Bioactive Factors; U.S. Pat. No. 5,543,158 Biodegradable Injectable Nanoparticles; U.S. Pat. No. 5,514,378 Biocompatible Polymer Membranes And Methods Of Preparation Of Three Dimensional Membrane Structures; U.S. Pat. No. 5,512,600 Preparation Of Bonded Fiber Structures For Cell Implantation; U.S. Pat. No. 5,500,161 Method For Making Hydrophobic Polymeric Microparticles; U.S. Pat. No. 5,487,390 Gas-filled polymeric microbubbles for ultrasound imaging; U.S. Pat. No. 5,399,665 Biodegradable polymers for cell transplantation; U.S. Pat. No. 5,356,630

Delivery system for controlled release of bioactive factors; U.S. Pat. No. 5,330,768 Controlled drug delivery using polymer/pluronic blends; U.S. Pat. No. 5,286,763 Bioerodible polymers for drug delivery in bone; U.S. Pat. No. 5,149,543 Ionically cross-linked polymeric microcapsules; U.S. Pat. No. 5,128,420 Method of making hydroxamic acid polymers from primary amide polymers; U.S. Pat. No. 5,122,367 Polyanhydride bioerodible controlled release implants for administration of stabilized growth hormone; U.S. Pat. No. 5,100,668 Controlled release systems containing heparin and growth factors; U.S. Pat. No. 5,019,379 Unsaturated polyanhydrides; U.S. Pat. No. 5,010,167 Poly(amide-and imide-coanhydride) for biological application; U.S. Pat. No. 4,948,587 Ultrasound enhancement of transbuccal drug delivery; U.S. Pat. No. 4,946,929 Bioerodible articles useful as implants and prostheses having predictable degradation rates; U.S. Pat. No. 4,933,431 One step preparation of poly(amide-anhydride); U.S. Pat. No. 4,933,185 System for controlled release of biologically active compounds; U.S. Pat. No. 4,921,757 System for delayed and pulsed release of biologically active substances; U.S. Pat. No. 4,916,204 Pure polyanhydride from dicarboxylic acid and coupling agent; U.S. Pat. No. 4,906,474 Bioerodible polyanhydrides for controlled drug delivery; U.S. Pat. No. 4,900,556 System for delayed and pulsed release of biologically active substances; U.S. Pat. No. 4,898,734 Polymer composite for controlled release or membrane formation; U.S. Pat. No. 4,891,225 Bioerodible polyanhydrides for controlled drug delivery; U.S. Pat. No. 4,888,176 Controlled drug delivery high molecular weight polyanhydrides; U.S. Pat. No. 4,886,870 Bioerodible articles useful as implants and prostheses having predictable degradation rates; U.S. Pat. No. 4,863,735 Biodegradable polymeric drug delivery system with adjuvant activity; U.S. Pat. No. 4,863,611 Extracorporeal reactors containing immobilized species; U.S. Pat. No. 4,861,627 Preparation of multiwall polymeric microcapsules; U.S. Pat. No. 4,857,311 Polyanhydrides with improved hydrolytic degradation properties; U.S. Pat. No. 4,846,786 Bioreactor containing suspended, immobilized species; U.S. Pat. No. 4,806,621 Biocompatible, bioerodible, hydrophobic, implantable polyimino carbonate article; U.S. Pat. No. 4,789,724 Preparation of anhydride copolymers; U.S. Pat. No. 4,780,212 Ultrasound enhancement of membrane permeability; U.S. Pat. No. 4,779,806 Ultrasonically modulated polymeric devices for delivering compositions; U.S. Pat. No. 4,767,402 Ultrasound enhancement of transdermal drug delivery; U.S. Pat. No. 4,757,128 High molecular weight polyanhydride and preparation thereof; U.S. Pat. No. 4,657,543 Ultrasonically modulated polymeric devices for delivering compositions; U.S. Pat. No. 4,638,045 Non-peptide polyamino acid bioerodible polymers; U.S. Pat. No. 4,591,496 Process for making systems for the controlled release of macromolecules.

The above discussion has demonstrated how the various variables associated with the cobalamin conjugates of the present invention can be independently varied to more particularly define specific classes of cobalamin conjugates encompassed by this invention. It is to be understood that the modification of one variable can be made independently of the modification of any other variable. Moreover, any number of embodiments can be defined by modifying two or more of the variables in such embodiments. A few of such embodiments are described below for purposes of exemplification.

Subembodiments 11-20: Any one of subembodiments 1-10, wherein the linker has a substantially constant molecular weight.

Subembodiments 21-30: Any one of subembodiments 1-10, wherein the linker is a polyamine of the following chemical structure: NR'(alkylene-NR')$_n$alkyleneNR', wherein n is from 1 to 20, the carbon length of alkylene can vary within the n units, and each R' is independently hydrogen, lower alkyl, or T.

Subembodiments 31-40: Any one of subembodiments 1-10, wherein the linker is spermine, spermidine, decamethylene tetraamine or pentamethylene hexamine.

IV. Chelating Group

Chelating groups can be used to link radionuclides to the TC- or IF-binding carrier of the present invention, either directly or via a linker. Any suitable chelating group can be employed. Suitable chelating groups include those disclosed in U.S. Pat. No. 5,739,313. Other suitable chelating groups are the thiazoline derivatives disclosed in U.S. Pat. No. 6,083,966, the pyridinones disclosed in U.S. Pat. No. 5,892,029, and the catecholaurates disclosed in U.S. Pat. No. 5,514,695.

In one embodiment, the chelating group can be NTA, HEDTA, DCTA, RP414, MDP, DOTATOC, CDTA, HYNIC, EDTA, DTPA, TETA, DOTA, DOTMP, DCTA, 15N4, 9N3, 12N3, or MAG3 (or another suitable polyamino acid chelator), which are described herein below, or a phosphonate chelator (e.g. EDMT). In a preferred embodiment, the chelating group is DTPA.

DTPA is diethylenetriaminepentaacetic acid; TETA is 1,4,8,11-tetraaza-cyclo-tetradecane-N,N',N'',N'''-tetraacetic acid; DOTA is 1,4,7,10-tetraaza-cyclododecane-N,N',N'', N'''-tetraacetic acid; 15N4 is 1,4,8,12-tetraazacyclo-pentadecane-N,N',N'',N'''-tetra-acetic acid; 9N3 is 1,4,7-triazacyclononane-N,N',N''-triacetic acid; 12N3 is 1,5,9-triazacyclododecane-N,N',N''-triacetic acid; polyaminoacid chelators, such as MAG3 is (N—(N—(N-((benzoylthio)acetyl)glycyl) glycyl)glycine); and DCTA is a cyclohexane-based metal chelator of the formula

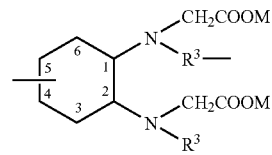

wherein $R^3$ may by $(C_1-C_4)$alkyl or $CH_2CO_2$—, which may be attached through positions 4 or 5, or through the group $R^3$ and which carries from 1 to 4 detectable metal or nonmetal cations (M*), monovalent cations, or the alkaline earth metals. Thus, with metals of oxidation state +1, each individual cyclohexane-based molecule may carry up to 4 metal cations (where both $R^3$ groups are $CH_2COOM^*$). As is more likely, with higher oxidation states, the number of metals will decrease to 2 or even 1 per cyclohexane skeleton. This formula is not intended to limit the molecule to any specific stereochemistry.

NTA, HEDTA and DCTA are disclosed in Poster Sessions, Proceedings of the 46th Annual Meeting, J. Nuc. Med., p. 316, No. 1386. RP414 is disclosed in Scientific Papers, Proceedings of the 46th Annual Meeting, J. Nuc. Med., p. 123, No. 499. MDP is disclosed in Scientific Papers, Proceedings of the 46th Annual Meeting, J. Nuc. Med., p. 102, No. 413. DOTATOC is disclosed in Scientific Papers, Proceedings of the 46th Annual Meeting, J. Nuc. Med., p. 102, No. 414 and Scientific Papers, Proceedings of the 46th Annual Meeting, J. Nuc. Med., p. 103, No. 415. CDTA is disclosed in Poster Sessions, Proceedings of the 46th Annual Meeting, J. Nuc. Med., p. 318, No. 1396. HYNIC is disclosed in Poster Sessions, Proceedings of the 46th Annual Meeting, J. Nuc. Med., p. 319, No. 1398.

Bifunctional chelators (i.e., chelating groups) based on macrocyclic ligands in which conjugation is via an activated arm attached to the carbon backbone of the ligand can also be employed as a chelating group, as described by M. Moi et al., J. Amer. Chem., Soc., 49, 2639 (1989) (2-p-nitrobenzyl-1,4, 7,10-tetraazacyclododecane-N,N',N'',N'''-tetraacetic acid); S. V. Deshpande et al., J. Nucl. Med., 31, 473 (1990); G. Kuser et al., Bioconj. Chem., 1, 345 (1990); C. J. Broan et al., J. C. S. Chem. Comm., 23, 1739 (1990); and C. J. Anderson et al., J. Nucl. Med. 36, 850 (1995) (6-bromoacetamido-benzyl-1, 4,8,11-tetraazacyclotetadecane-N,N',N'',N'''-tetraacetic acid (BAT)).

In addition, the chelator or chelating group can be any of the chelating groups disclosed in Scientific Papers, Proceedings of the 46th Annual Meeting, *J. Nuc. Med.*, Wednesday, Jun. 9, 1999, p. 124, No. 500.

Specifically, the chelating group can be any one of the carbonyl complexes disclosed in Waibel et al., *Nature Biotechnology*, 897-901, Vol. 17, September 1999; or Sattelberger et al., *Nature Biotechnology*, 849-850, Vol. 17, September 1999.

Specifically, the detectable chelating group can be any one of the carbonyl complexes disclosed in Waibel et al., *Nature Biotechnology*, 897-901, Vol. 17, September 1999; or Sattelberger et al., *Nature Biotechnology*, 849-850, Vol. 17, September 1999, further comprising a metallic radionuclide. More specifically, the detectable chelating group can be any one of the carbonyl complexes disclosed in Waibel et al., *Nature Biotechnology*, 897-901, Vol. 17, September 1999; or Sattelberger et al., *Nature Biotechnology*, 849-850, Vol. 17, September 1999, further comprising Technetium-99m, Rhenium-186, or Rhenium-188.

V. Detectable and/or Therapeutic Radionuclides

As used herein, a "detectable radionuclide" is any suitable radionuclide (i.e., radioisotope) capable of being detected in a diagnostic procedure in vivo or in vitro. Suitable detectable radionuclides include metallic radionuclides (i.e., metallic radioisotopes) and non-metallic radionuclides (i.e., non-metallic radioisotopes).

Suitable metallic radionuclides (i.e., metallic radioisotopes or metallic paramagnetic ions) include Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-67, Erbium-169, Europium-152, Gallium-64, Gallium-68, Gadolinium-153, Gadolinium-157 Gold-195, Gold-199, Hafnium-175, Hafnium-175-181, Holnium-166, Indium-110, Indium-111, Iridium-192, Iron-55, Iron-59, Krypton-85, Lead-210, Lutetium-177, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, and Zirconium-95.

The compounds of the invention can also comprise one or more (e.g., 1, 2, 3, or 4) non-metallic radionuclide which can be directly linked to a residue of the compound of formula I at any synthetically feasible site, or can be linked to a residue of the compound of formula I, by a linker, at any synthetically feasible site. Suitable linkers are described herein. In addition, suitable points of attachment of the compound of formula I for the non-metallic radionuclide, either directly or by a linker, are also described herein. The invention also provides compounds having more than one non-metallic radionuclide attached to a compound of formula I, either directly, or by a linker.

Specifically, the non-metallic radionuclide can be a non-metallic paramagnetic atom (e.g., Fluorine-19); or non-metallic positron emitting radionuclide (e.g., Carbon-11, Fluorine-18, Iodine-12 or Bromine-76), or a nonmetallic gamma emitting radionuclide such as Iodine-123 or Iodine-131. Fluorine-19 is a suitable non-metallic paramagnetic for use the compounds of the present invention in part because there is typically little or no background noise associated with the diagnostic use of fluorine in the body of a mammal (e.g., human).

As used herein, a "therapeutic chelating group" is a chelating group comprising a metallic radionuclide (e.g., a metallic radioisotope) that possesses therapeutic efficacy against cancer or other neoplastic cells in vivo or in vitro. Any suitable chelating group can be employed.

Specifically, the therapeutic chelating group can be any of the carbonyl complexes disclosed in Waibel et al., *Nature Biotechnology*, 897-901, Vol. 17, September 1999; or Sattelberger et al., *Nature Biotechnology*, 849-850, Vol. 17, September 1999, further comprising a metallic radionuclide. More specifically, the therapeutic chelating group can be any of the carbonyl complexes disclosed in Waibel et al., *Nature Biotechnology*, 897-901, Vol. 17, September 1999; or Sattelberger et al., *Nature Biotechnology*, 849-850, Vol. 17, September 1999, further comprising Rhenium-186 or Rhenium-188.

VI. Antiproliferative Agents

As used herein, the therapeutic agent is an antiproliferative agent that decreases the hyperproliferation of cells. Proliferative disorders are currently treated by a variety of classes of compounds includes alkylating agents, antimetabolites, natural products, enzymes, biological response modifiers, miscellaneous agents, hormones and antagonists, such as those listed in the Background of the Invention. Any of the antiproliferative agents listed in the Background, any listed below, or any other such agent known or discovered to exhibit an antiproliferative effect that can be more effectively delivered by conjugation to a TC- or IF-binding carrier can be used in accordance with this invention.

In an alternative embodiment, any of the antiproliferative agents listed in the Background or below or any other such known agents can be used in combination with a TC- or IF-binding carrier/therapeutic and/or agent to achieve a combination therapeutic effect.

The antiproliferative agent can be bound through a covalent bond, a dative bond, a coordination bond, complexation (such as found in a bound antibody/epitope), or ionic bond. Covalent bonding is preferred over ionic bonding, however, a tightly held ionic bond may be suitable. Below are nonlimiting examples of how agents can be attached to carriers. Other routine means are known to those skilled in the art, and are assumed included within the scope of the invention.

Free Amines or Amides

The following are non-limiting examples of antiproliferative agents that contain an amine group or an amide group, and thus can be linked to the TC or IF binding carrier through that functional moiety, using standard chemical reactions for covalent bond formation to a nitrogen atom.

Cyclophosphamide
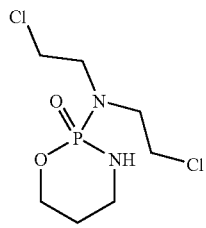
Ifosfamide
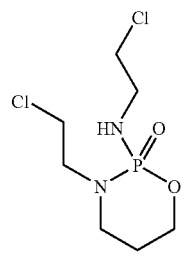
Carmustine (BCNU)
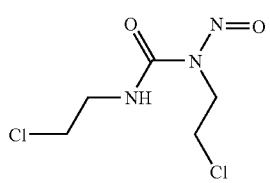
Lomustine (CCNU)
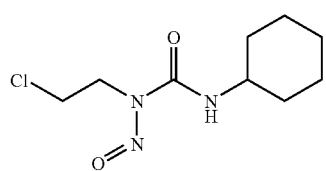
Semustine (methyl-CCNU)
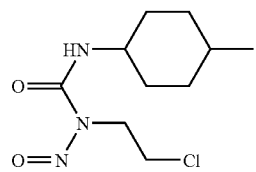
Fluorouracil (5-fluorouracil; 5-FU)
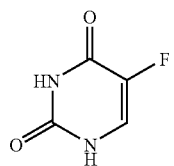
fluorodopan
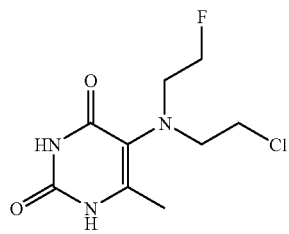
uracil nitrogen mustard (Desmethyldopan; Nordopan)
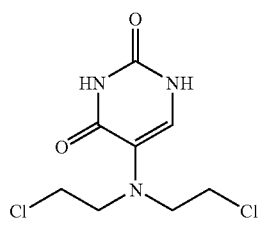
mitozolamide
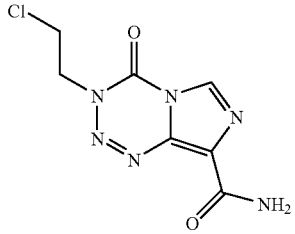
Dactinomycin (actinonmycin D)
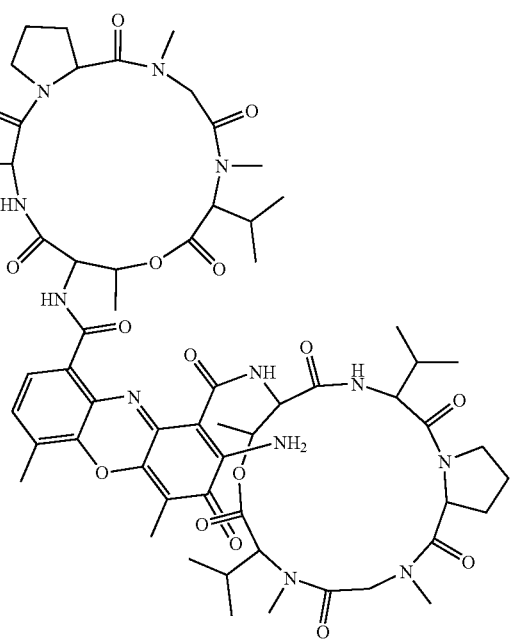

asaley
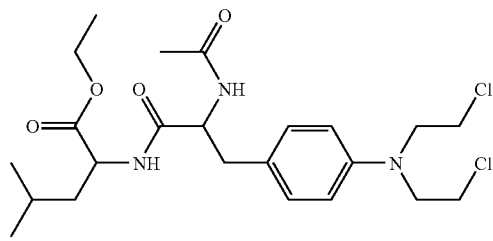
Cisplatin (cis-DDP)
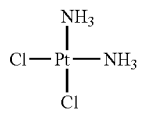
Carboplatin (CBDCA)
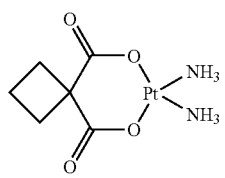
tetraplatin (Ormaplatin)
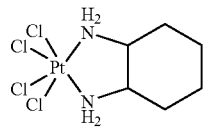
Hydroxyurea
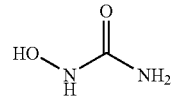
Procarbazine (N-methylhydrazine, MIH)
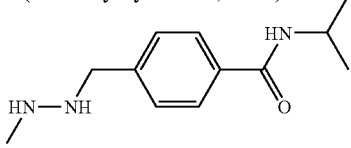
Aminoglutethimide
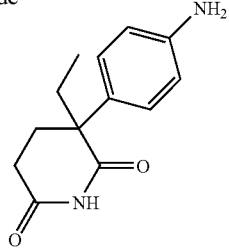
Flutamide
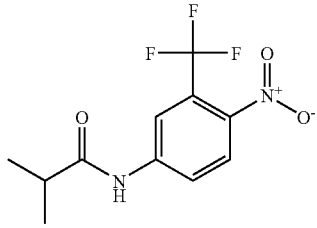
Leuprolide
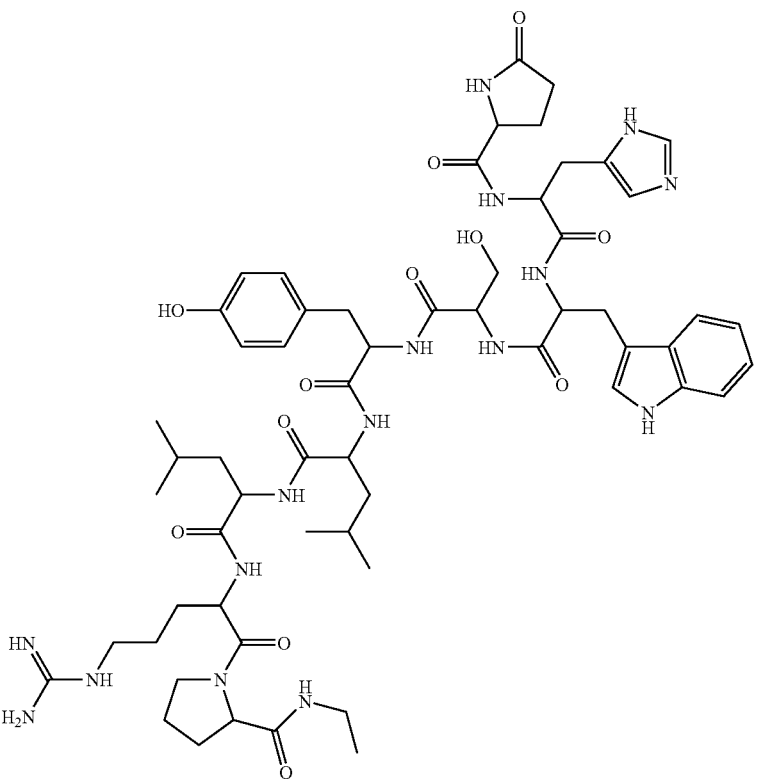

Diaziquone (AZQ)
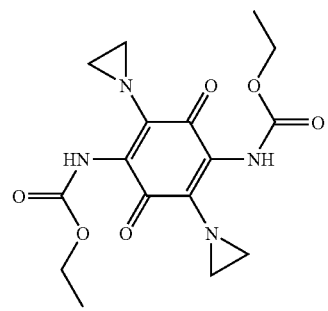
hepsulfam
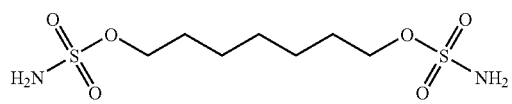
Mitomycin C (MMC)
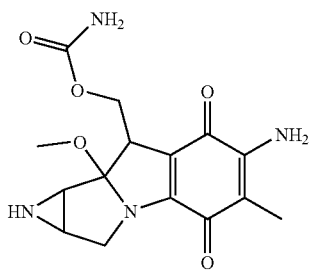
porfiromycin
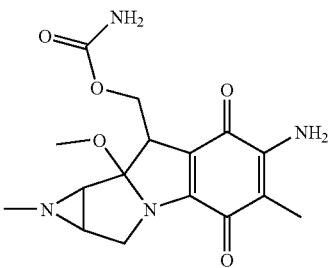
PCNU
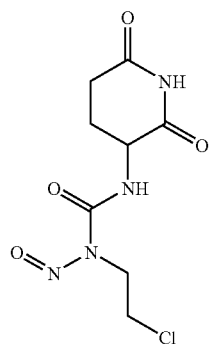
piperazine
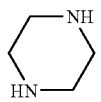
piperazinedione,
spirohydantoin mustard (Spiromustine; SHM)
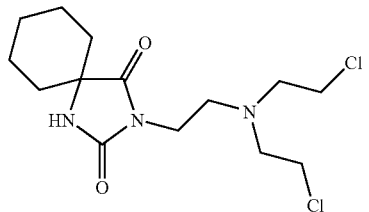
Yoshi-864
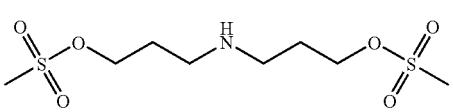
allocolchicine
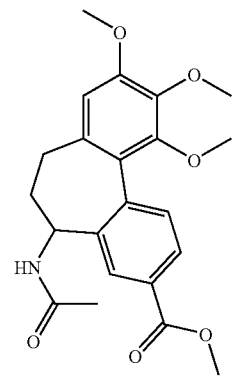
colchicine (and its Derivatives)
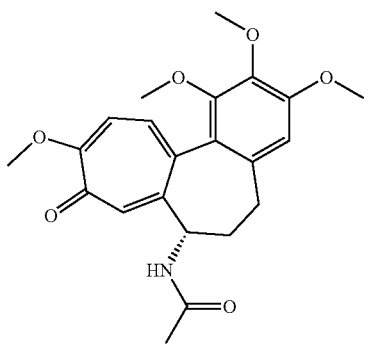

thiocolchicine
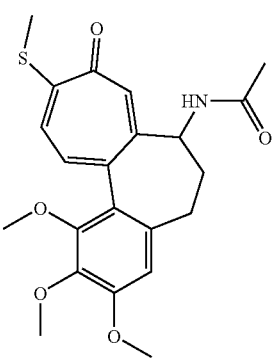
amsidine (m-AMSA)
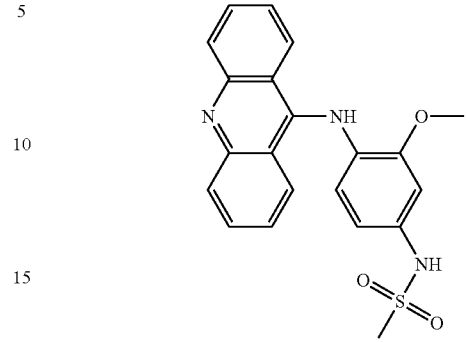
pyrazoloacridine
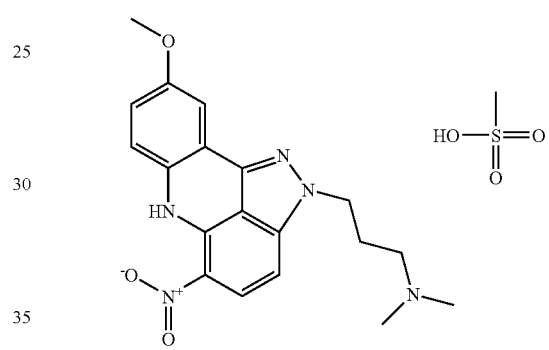
bisantrene HCl (CL 216942)
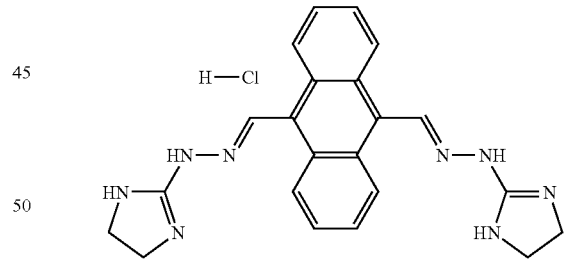
dolastatin 10
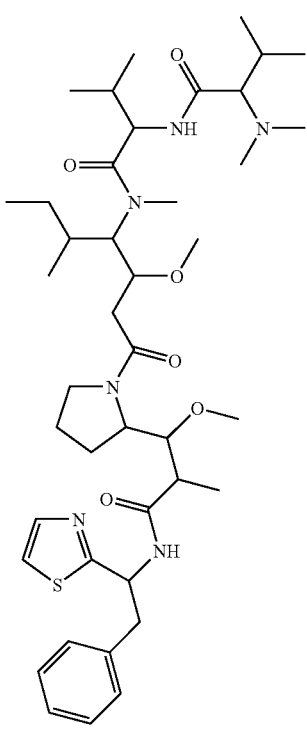
Dacarbazine (DTIC; DIC; DTIC-Dome; Dacatic; Deticene; DTIE; ICDMT; ICDT)
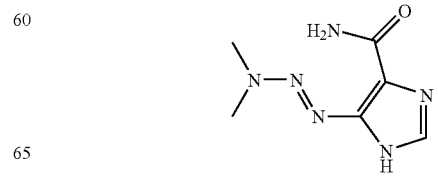
amonafide
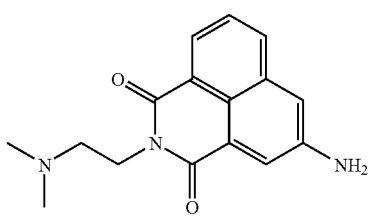

RU-486 (Mifepristone)

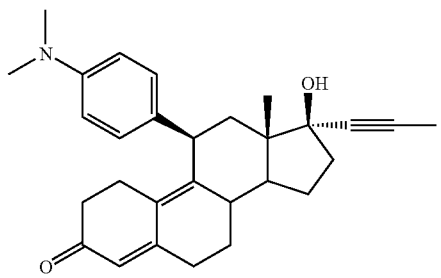

Thalidomide (K 17; Distaval; Softenon; Sedalis; Talimol; Pantosediv; Neurosedyn; Kevadon; Contergan; Synovir; NEO; neosedyn; neurodyn; nevrodyn; nibrol; pangul)

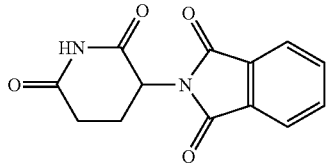

Carboxylic Acids

The following are non-limiting examples of antiproliferative agents that contain a carboxylic acid, and thus can be linked to the TC or IF binding carrier through that functional moiety, using standard chemical reactions for covalent bond formation by derivatization of a carboxylic acid.

Chlorambucil

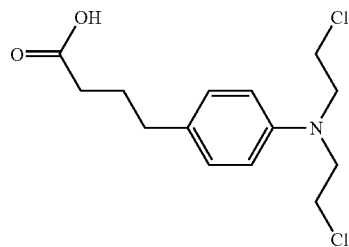

Methotrexate (amethopterin)

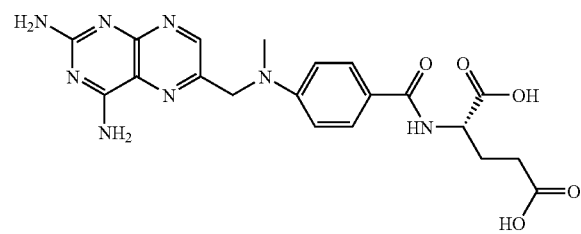

carboxyphthalatoplatinum

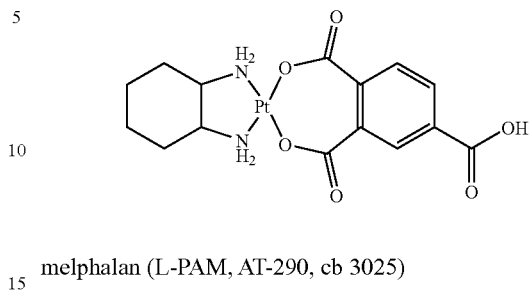

melphalan (L-PAM, AT-290, cb 3025)

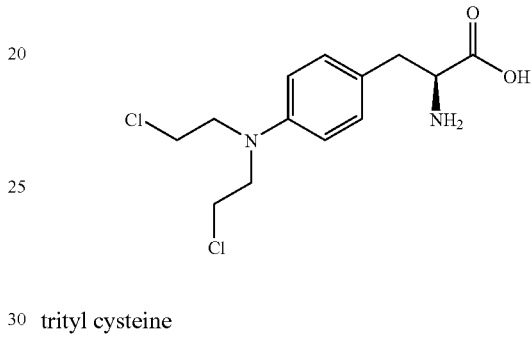

trityl cysteine

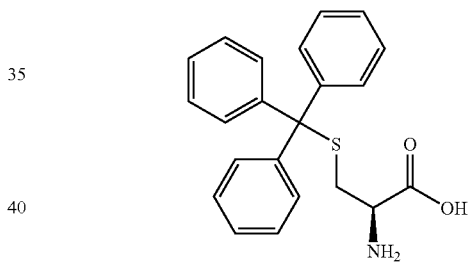

all-trans retinoic acid (vitamin A)

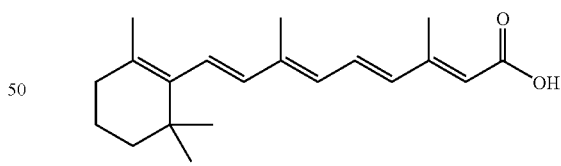

retinoids (e.g. tazarotene, or Tazorac), acitretin (Soriatane®)

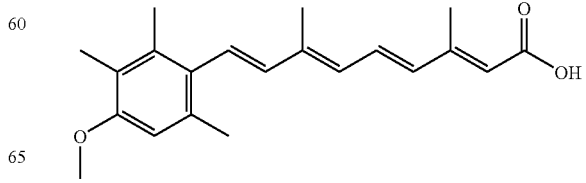

Methotrexate

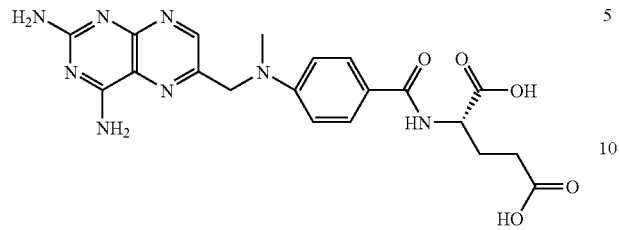

Benzyl carboxylic acids: aspirin, diclofenac, indomethacin, ketorolac, ketoprofen, naproxen, diflunisal, mefenamic acid, ioxoprofen, tolmefenamic acid, indoprofen, pirprofen, fenoprofen, zaltoprofen, sulindac, tolmetin, suprofen, flurbiprofen, pranoprofen, niflumic acid, flufenamic acid, zomopirac, bromfenac, fenclofenac, alcofenac, orpanoxin, etodolic acid, fleclozic acid, amfenac, emfenamic acid, benoxaprofen, fluoxaprofen, carprofen, isofezolac, aceloferac, fenpufen, fenclorac, meclofenamate, and clindac. Second line agents include gold salts, penicillamine, methotrexate, and antimalarials.

Free Hydroxyl/Mercapto Groups

The following are non-limiting examples of antiproliferative agents that contain a free hydroxyl or thiol group, and thus can be linked to the TC or IF binding carrier through that functional moiety, using standard chemical reactions for covalent bond formation by derivatization of a hydroxyl or thiol.

Prednisone

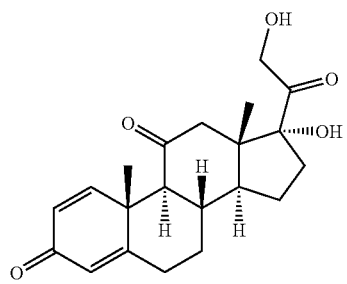

Corticosteroids (cortisone)

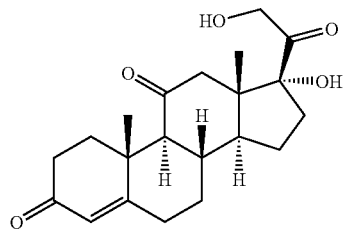

estradiol

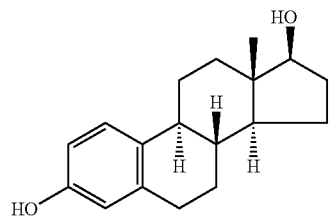

betamethasone sodium phosphate (betnesol)

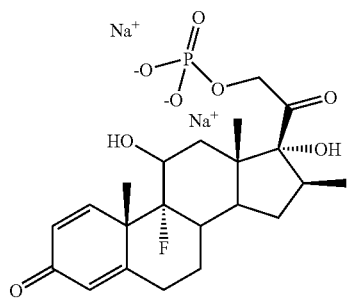

betamethasone acetate

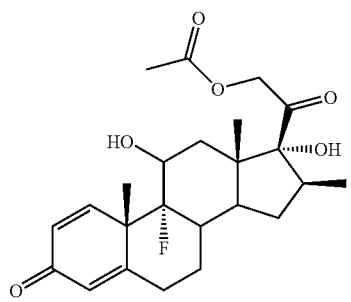

Floxuridine (fluorodeoxyuridine; FUdR)

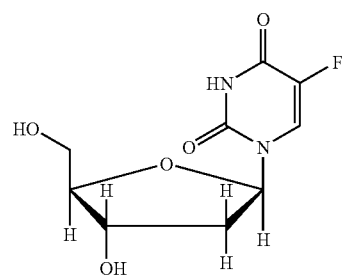

| 51 | 52 |
|---|---|
| Cytarabine (cytosine arabinoside) | Vinblastine (VLB) |
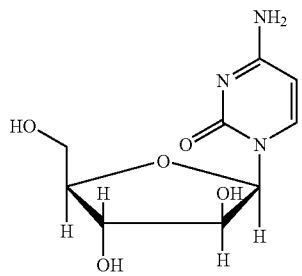
fludarabine phosphate
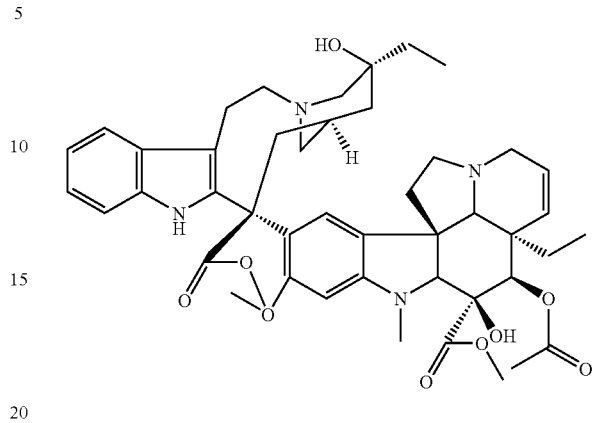
Vincristine
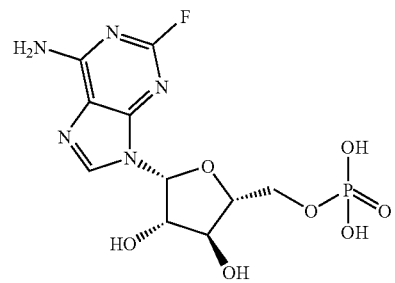
Pentostatin (2'-deoxycyoformycin)
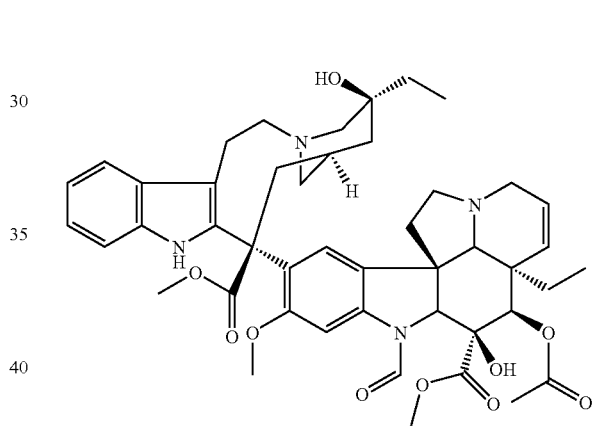
Etoposide
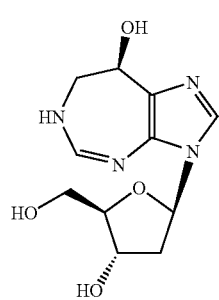
Mercaptopurine (6-mercaptopurine; 6-MP; Thioguanine, 6-thioguanine, TG)
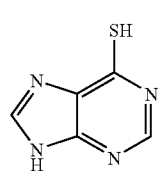

53
Teniposide
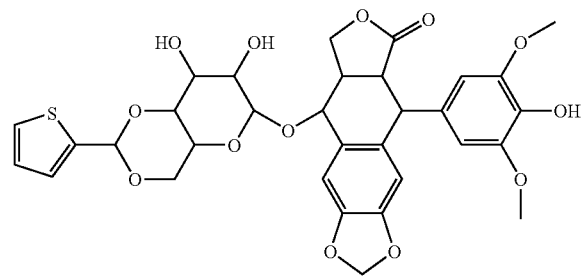
rubidazone (daunorubinicin, RP22050, RUB)
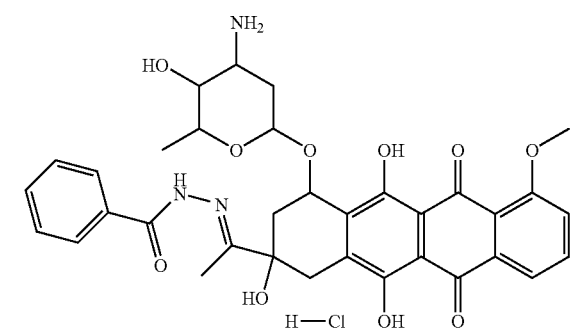
Daunorubinicin (daunomycin; rubidomycin)
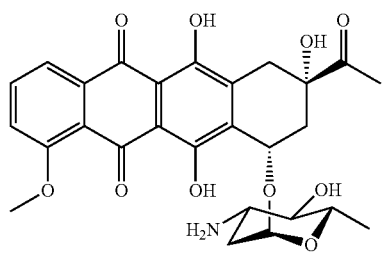
54
Doxorubicin
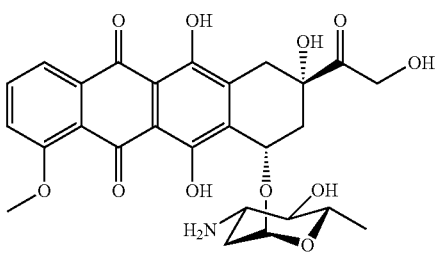
idarubicin (Idamycin; 4-demethoxy-daunorubicin)
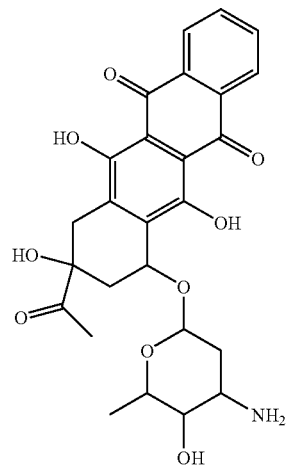
Bleomycin
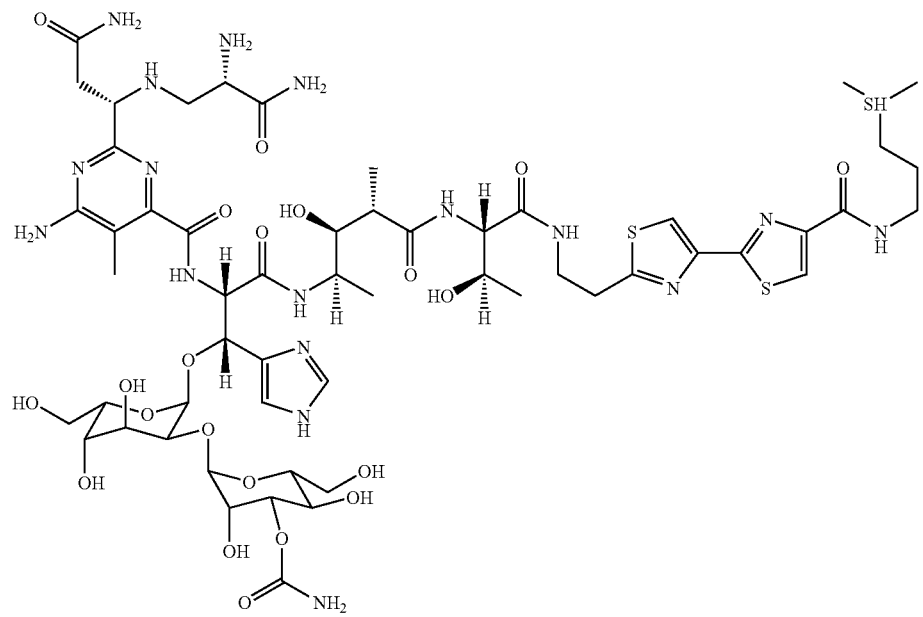

mitoxantrone
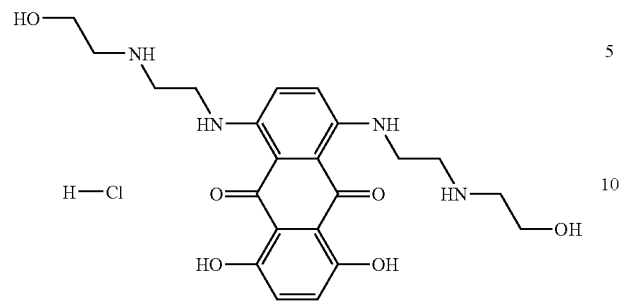
Plicamycin (mithramycin)
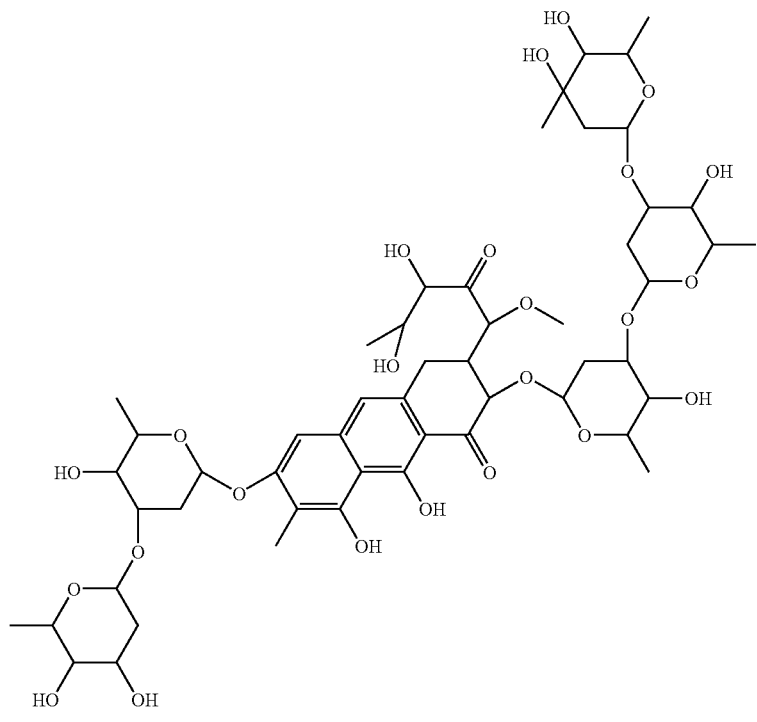
paclitaxel (taxol) and Derivatives
taxotere (docetaxel)
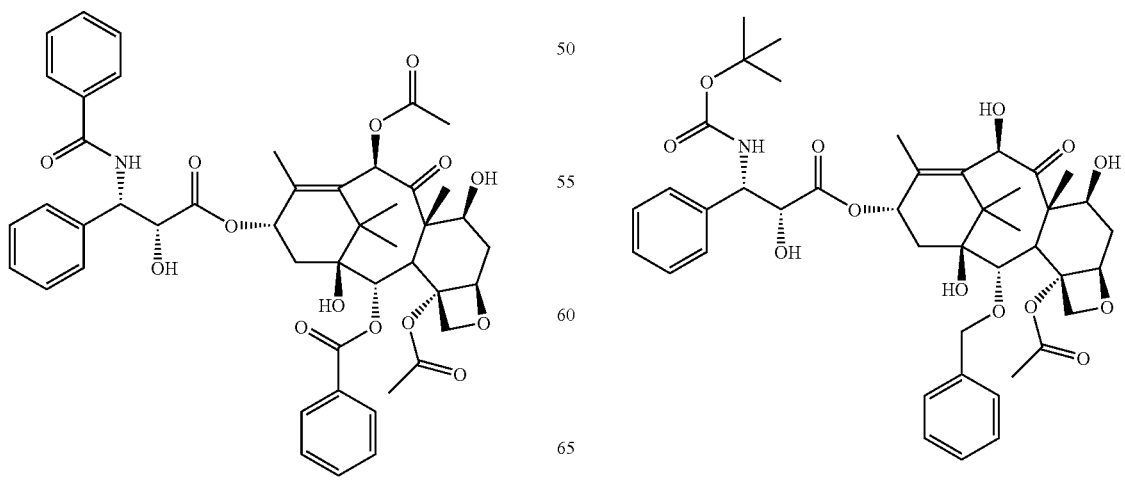

teniposide (VM-26)
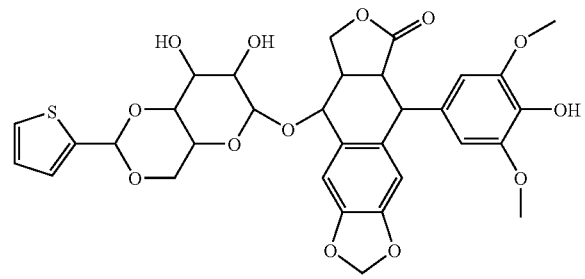
etoposide (vepesid, EPEG, VP-16, VP-16213)
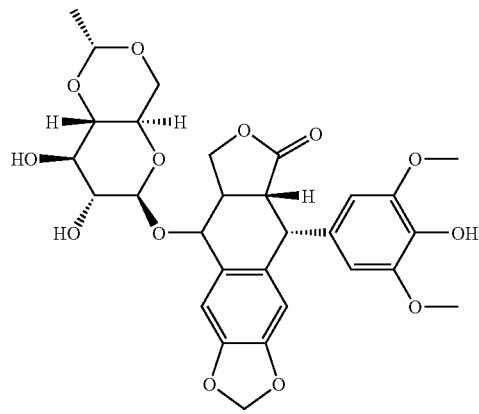
hycanthone
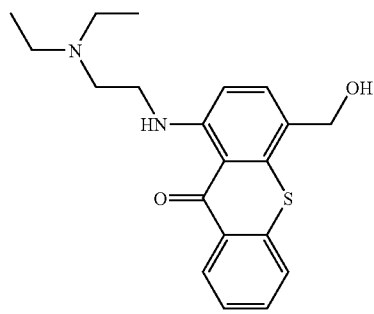
camptothecin (and its Derivatives)
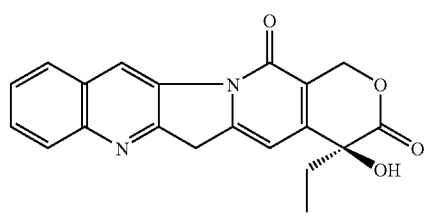
mitoxantron (DHAQ, CL-232315)
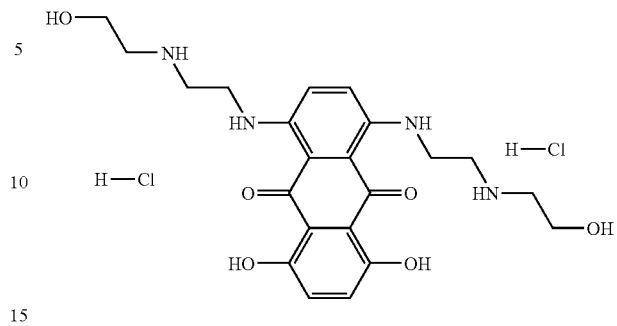
anthrapyrazole and its Derivatives
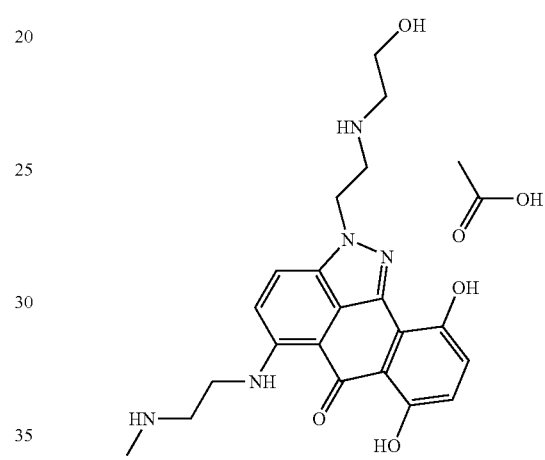
menogaril (7-OMEN, U-52047)
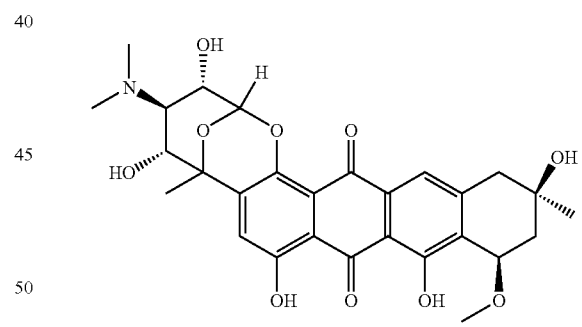
oxanthrazole (piroxantrone HCl)
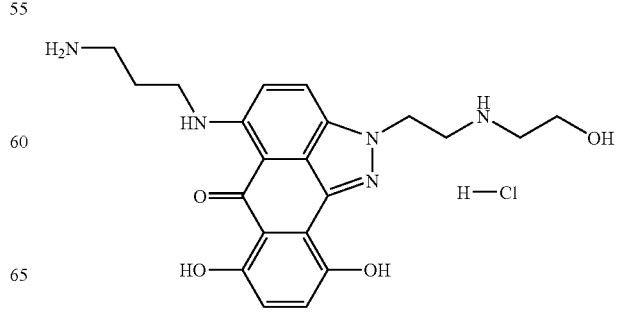

59
diethylstilbestrol diphosphate
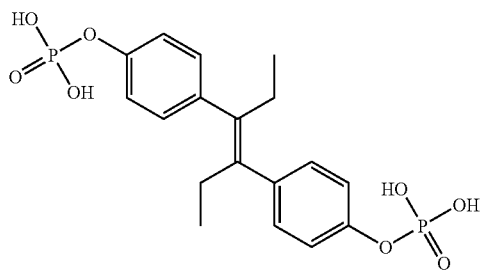
iproplatin (CHIP)
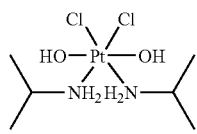
chlorozotocin (DCNU)
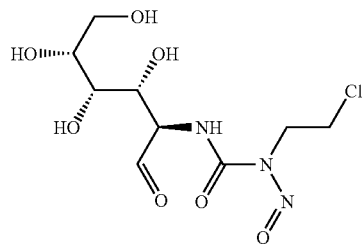
dianhydrogalactitol (DAD, DAG)
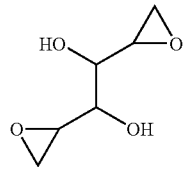
streptozotocin (STR)
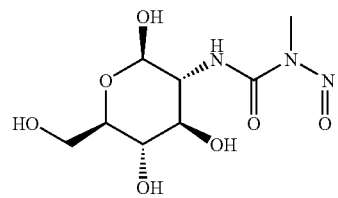
60
maytansine (MTS)
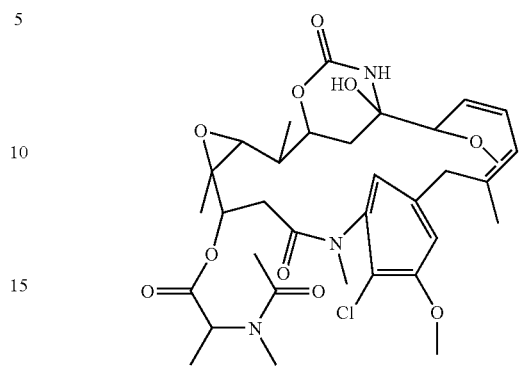
rhizoxin
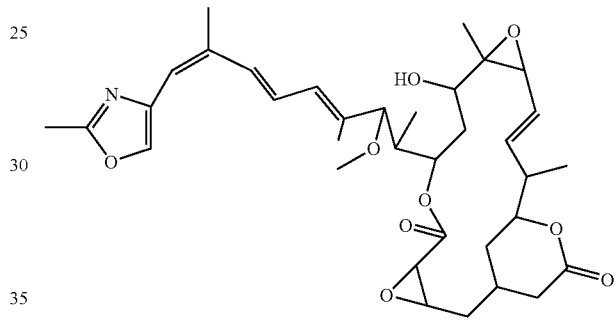
bromocresol green (BCG)
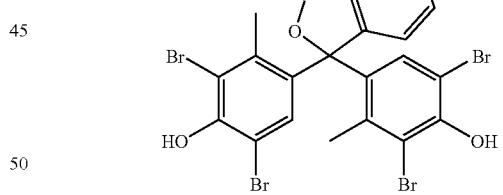
porfimer sodium (arfonad, photofrin)
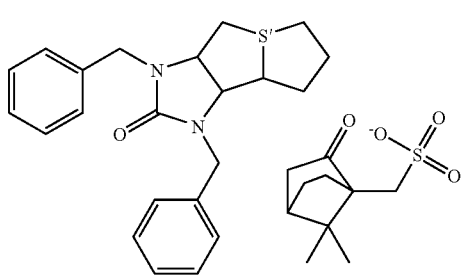

Anthralin (Dithranol, anthra-derm; Lasan; psoriacid-stift; batridrol; psoriacide; chrysodermol; cignolin; cygnolin; dermaline; derobin; DithraSal; Dithrocream; Psorin)

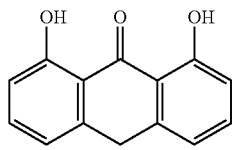

Biologics

The following are non-limiting examples of biologics that can be attached using known chemistry for attachment of such moieties, for example, through protein or peptide covalent bond formation, complexation such as through an antibody/epitope linkage, or other ionic or covalent bond formation.

Nonlimiting examples include: Cyclosporine (Neoral®), Calcipotriene (a synthetic form of vitamin $D_3$); Coal tar, gliadel, Halichondrin B, navelbine, cyclodisone, Mixtozantrone, alpha interferon, Interferon-alfa, interferon alfa-2b recombinant, interferon alfa-2a recombinant (aldesleukin), L-Asparaginase, filgrastim (neupogen, G-CSF), sagramostin (GM-CSF), interleukin-2, rocarbazine, droloxifene roloxifene, estramucine phosphate sodium, streptozoci, and goserelin acetate.

Miscelleneous

The following are non-limiting examples of antiproliferative agents that do not have readily available functional groups to derivatize for covalent attachment to the TC-binding or IF-binding carrier or linker, but can be attached through a suitable ionic bond with close salt formation, wherein the carrier or linker contains an appropriate counterion.

testolactone

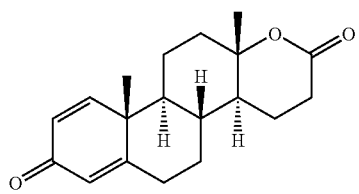

Megestrol acetate

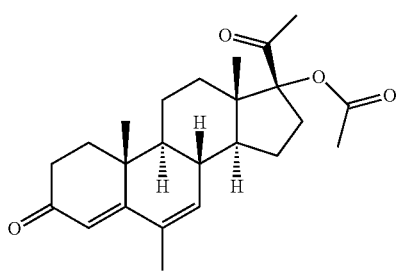

altretamine (Hexamethylmelamine; HMM)

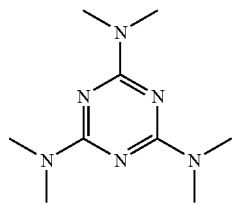

triethylenemelamine (triamelin, tetramine, TEM, TET, persistol)

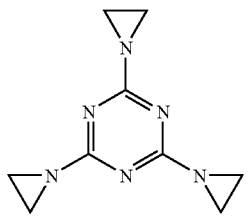

teroxirone (TGIC, TGT)

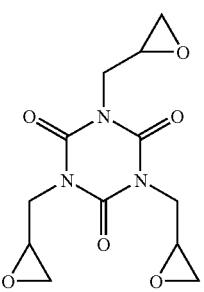

pipobroman

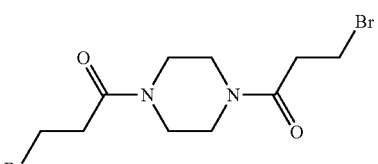

levamisole (ergamisol)

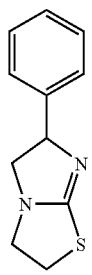

toremifene

Mechlorethamine (nitrogen mustard, MBA, Dichloren)

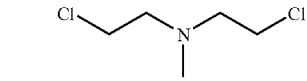

Thiotepa

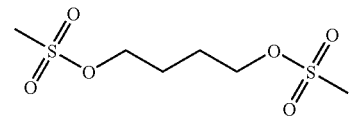

Busulfan

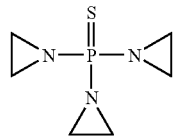

Tamoxifen

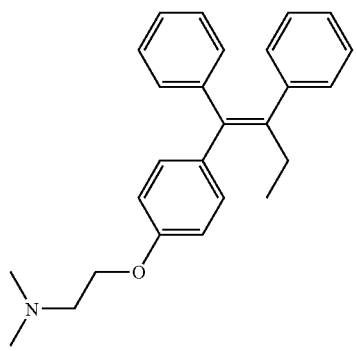

Mitotane (o,p'-DDD)

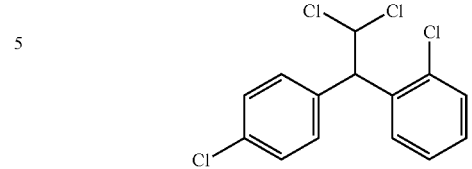

clomesone

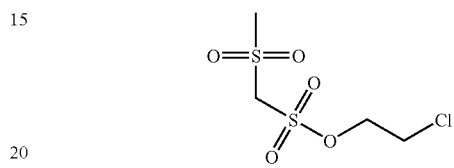

VII. Pharmaceutically Acceptable Salt or Prodrug Formulations

The term "pharmaceutically acceptable salt or prodrug" is used throughout the specification to describe any pharmaceutically acceptable form (such as an ester, mono-, di- or tri-phosphate ester, salt of an ester or a related group) of a TC- or IF-binding carrier, which, upon administration to a patient, provides the active compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess activity against infectious disease or are metabolized to a compound that exhibits such activity.

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts may also be formed, including, sulfate, nitrate, bicarbonate and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the TC- or IF-binding carriers described herein can be administered as a prodrug to increase the activity, bioavail-

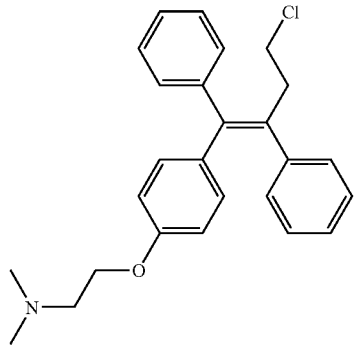

ability, stability or otherwise alter the properties of the carrier. A number of prodrug ligands are known. In general, alkylation, acylation or other lipophilic modification of the mono, di or triphosphate of the $G^1$ substituent on the five-membered "sugar-ring" moiety will increase the stability of the carrier. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1-17. Any of these can be used in combination with the disclosed carriers to achieve a desired effect.

The $G^1$ substituent of the active carrier can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses.* 6:491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hostetler, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine." *Antimicrob. Agents Chemother.* 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the TC- or IF-binding agent, preferably at the $G^1$ position of the carrier or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent applications that disclose lipophilic substituents that can be attached to the carrier of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

VIII. Stereoisomerism and Polymorphism

Compounds of the present invention having a chiral center may exist in and be isolated in optically active and racemic forms. Some compounds may exhibit polymorphism. The present invention encompasses racemic, optically-active, polymorphic, or stereoisomeric form, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution.

IX. Transport Proteins

In humans, the average daily intake (in a Western diet) of vitamin $B_{12}$ is about 4-5 g. Additional synthesis of cobalamin may be produced in the ileum and the right colon, but in an unknown amount. The total lumenal cobalamin that must be assimilated each day in humans is estimated at 7-14 g, the sum of the dietary and endogenous cobalamin. Intestinal epithelial cells possess carriers and transporters that are highly efficient in the uptake of the small products of digestion, such as vitamins, minerals and amino acids. These mechanisms are necessary for the uptake of these molecules, as the epithelial cell layer presents an almost impenetrable barrier to peptides larger than five or six amino acids in size. The cobalamins of the present invention are large molecules that are not absorbed directly from the intestine, as they are too big to diffuse across the intestinal wall. Therefore, the absorption of the cobalamins is dependent upon transport proteins. The uptake of vitamin B12 from the intestine to the blood is perhaps the most complex uptake mechanism of all the vitamins, involving at least four separate cobalamin binding proteins and receptors.

Three distinct groups of transport proteins are involved in the absorption and transport of cobalamins: intrinsic factor (IF), haptocorrin (HC; also called R-protein; in which transcobalamin I (TC-I) and transcobalamin m (TC-III) are members) and transcobalamin II (TC-II). Both IF and TC II deficiencies lead to abnormalities such as megaloblastic anemia and demyelinating disorder of the nervous system. Each protein only has one subunit and one binding site to cobalamin. IF is a 45 kDa (in humans) to 55 kDa (in hogs) plasma glycoprotein with 15% carbohydrate content. HC's are 58 kDa (in humans) to 60 kDa (in rabbits) plasma glycoproteins of 33-40% carbohydrate content with 16-19 sialic acid residues. Human TC-II is a 43 kDa plasma protein (in humans) with 0% carbohydrate content. Each binding protein has a separate affinity for cobalamin, as well as separate cell receptors. Generally, cobalamin is initially bound by HC in the stomach, followed by IF in the small intestine. An IF receptor is then involved in the uptake of the IF-cobalamin complex by the intestinal epithelial cell, leading to the proteolytic release of cobalamin, and subsequent binding to TC-II.

Intrinsic factor (IF) and haptocorrin (HC; are the main intestinal lumenal cobalamin binders. In particular IF is of particular relevance to the field of oral peptide and protein delivery. Therefore, IF is mainly produced in the gastric body and medium sized ducts and HC is mainly produced in granulocytes, the yolk sac, mammary glands, salivary acini and ducts. In general, in plasma or serum, cobalamin is also bound to HC (derived from white cells) or to TC-II. The former complex is taken up by the liver, delivering free cobalamin to the intestinal lumen as the first limb of an enterohepatic circulation.

IF is the most specific of the cobalamin-binding proteins. Cyanocobalamin, hydoxy-cobalamin (HOCbl), methylcobalamin (MeCbl) and adenyosylcobalamin (AdoCbl) bind to intrinsic factor with similar affinities, thereby suggesting that the upper-axial ligand of the cobalt does not influence the binding significantly. However, after dietary release of vitamin $B_{12}$, the affinity for the cobalamin for IF is reduced, due to the low pH. Rather, the released vitamin $B_{12}$ is preferentially bound to salivary HC, as HC may protect the vitamin from acid hydrolysis (possibly due to the extensive glycosylation of HC).

HC comprises a group of immunologically identical proteins secreted into many body fluids (plasma, milk, amniotic fluid, saliva and gastric juices) from many types of cells (granulocytes, mammary glands, yolk sac or visceral placental membranes, salivary duct and acinar cells, and gastric mucosa of some species). These proteins were known previously as R proteins (for rapid electrophoresis), non-intrinsic factors or transcobalamin I and III. They are characterized by different glycosylation processes and account for much of the total bound cobalamin in the serum (about 80% of bound cobalamin in serum). HC turns over very slowly ($t_{1/2}$=10 days) and appears to serve as the major storage protein for cobalamin and may also stabilize serum cobalamin against transdermal photolysis (Allen, R. H. Prog Hematol. 1975, 9, 57-84).

Within the proximal small intestine, HC is degraded by pancreatic enzymes, freeing cobalamin to combine with other transport proteins, most notably IF. In contrast to HC's, the IF-cobalamin complex is resistant to proteolytic digestion. Once the cobalamin-transport protein is internalized via receptor-mediated endocytosis, the cobalamin is cleaved from transport protein via protease(s) and bound to transcobalamin II (TC II). From there, the TC II-cobalamin complex is used for the transport of absorbed cobalamin to peripheral tissues. Therefore, TC-II is found in most tissues. Antibodies to TC II inhibit the transport of cobalamins and block the proliferation of leukemic cells in vitro (McLean, G. R. et al. Blood, 1997, 89, 235-242). In cow's milk, in particular, the major cobalamin binder is not HC, but rather TC-II (Fedosov, S. N. et al. Biochemistry 1995, 34, 16082-16087 and Fedosov, S. N. et al. Biochim. Biophys. Acta. 1996, 1292, 113-119).

Early attempts to purify transport proteins utilized conventional techniques such as ammonium sulfate fractionation, ion exchange and size exclusion chromatography. These methods yielded a product that was devoid of the other types of transport proteins, and in particular, separation of TC-II from TC-I was possible, but contained other plasma proteins. The introduction of affinity chromatography provided pure proteins even in extremely low concentrations. Three main types of affinity columns have been used to purify the transport proteins, in particular, columns containing cobalamin coupled to different matrices. The first was a monocarboxylic acid derivative of cobalamin linked to Sepharose beads via a diamino-dipropylamine spacer arm (Allen, R. H. et al. J. Biol Chem. 1972, 247, 7695-7701 and Allen, R. H. et al. J. Biol Chem. 1973, 248, 3660-3669). However, it may be necessary to use a chaotropic reagent to elute the protein from the matrix, possibly resulting in a denatured transport protein, which may not be able to renature. For instance, the elution of the bound protein from Cohn fraction III of human plasma, a mixture that contains 27-40% of the plasma TC-II, required the use of guanidine hydrochloride to release the denatured TC-II, which could not be renatured.

To avoid the use of chaotropic reagents, temperature- or photolabile linkages between the cobalamin and the insoluble matrix were developed (Nexo, E. "Cobalamin binding proteins," in Vitamin $B_{12}$ and $B_{12}$-proteins, eds Krantler, B.; Arigoni, D. and Golding, B. T.; Wiley & Sons, Ltd. 461-475). Matrices formed in this manner are able to release the transport protein by dissociating the cobalamin from the matrix, thus providing the transport protein saturated with cobalamin, circumventing the denaturant effect of chaotrophic agents.

In a preferred embodiment, for large scale purification of transport protein, ion exchange chromatography or ammonium sulfate fractionation is used prior to the purification of the transport protein via an affinity column to concentrate the sample. In an alternate embodiment, ion exchange or size exclusion chromatography is used subsequent to the purification of the transport protein via an affinity column.

X. Disorders Characterized by Abnormal Cellular Proliferation

Non-limiting examples of proliferative disorders other than neoplasms that can be treated and/or imaged with a TC- or IF-binding carrier linked to a therapeutic and/or diagnostic agent include those in Table 1, as well as any others listed or described in the Background of the Invention or otherwise in the specification.

TABLE 1

| Organ System | Disease/Pathology |
| --- | --- |
| Dermatological | Psoriasis (all forms), acne vulgaris, acne rosacea, common warts, anogenital (venereal) warts, eczema; lupus associated skin lesions; dermatitides such as seborrheic dermatitis and solar dermatitis; keratoses such as seborrheic keratosis, senile keratosis, actinic keratosis, photo-induced keratosis, skin aging, including photo-induced skin aging, keratosis follicularis, keloids and Prophylaxis against keloid formation; leukoplakia, lichen, planus, keratitis, contact dermatitis, eczema, urticaria, pruritus, hidradenitis, acne inversa |
| Cardiovascular | Hypertension, vasculo-occlusive diseases including Atherosclerosis, thrombosis and restenosis after angioplasty; acute coronary syndromes such as unstable angina, myocardial infarction, ischemic and non-ischemic cardiomyopathies, post-MI cardiomyopathy and myocardial fibrosis, substance-induced cardiomyopathy. |
| Endocrine | Insulin resistant states including obesity, diabetes mellitus (types 1 &2), diabetic retinopathy, macular degeneration associated with diabetes, gestational diabetes, impaired glucose tolerance, polycystic ovarian syndrome; osteoporosis, osteopenia, accelerated aging of tissues and organs including Werner's syndrome. |
| Urogenital | Endometriosis, benign prostatic hyperplasia, leiomyoma, Polycystic kidney disease, diabetic nephropathy. |
| Pulmonary | Asthma, chronic obstructive pulmonary disease (COPD), reactive Airway disease, pulmonary fibrosis, pulmonary hypertension. |

TABLE 1-continued

| Organ System | Disease/Pathology |
| --- | --- |
| Connective tissue/joints | Immunological Rheumatoid arthritis, Raynaud's phenomenon/disease, Sjogren's Syndrome, systemic sclerosis, systemic lupus erythematosus, vasculitides, ankylosing spondylitis, osteoarthritis, reactive arthritis, psoriatic arthritis, fibromyalgia. |
| Other | Fibrocystic breast disease, fibroadenoma, chronic fatigue syndrome. |

Nonlimiting examples of neoplastic diseases or malignancies treatable and/or diagnosable with the TC- or IF-binding carrier linked to a therapeutic and/or diagnostic agent are listed in Table 2.

TABLE 2

| Organ System | Malignancy/Cancer type |
| --- | --- |
| Skin | Basal cell carcinoma, melanoma, squamous cell carcinoma; cutaneous T cell lymphoma; Kaposi's sarcoma. |
| Hematological | Acute leukemia, chronic leukemia and myelodysplastic syndromes. |
| Urogenital | Prostatic, renal and bladder carcinomas, anogenital carcinomas including cervical, ovarian, uterine, vulvar, vaginal, and those associated with human papilloma virus infection. |
| Neurological | Gliomas including glioblastomas, astrocytoma, ependymoma, medulloblastoma, oligodendroma; meningioma, pituitary adenoma, neuroblastoma, craniopharyngioma. |
| Gastrointestinal | Colon, colorectal, gastric, esophageal, mucocutaneous carcinomas. |
| Breast | Breast cancer including estrogen receptor and progesterone Receptor positive or negative subtypes, soft tissue tumors. |
| Metastasis | Metastases resulting from the neoplasms. |
| Skeletal | Osteogenic sarcoma, malignant fibrou histeocytoma, chondrosarcoma, rhabdomyosarcoma, leiomyosarcoma, myeloma. |
| Diffuse Tumors | Lymphoma (non-Hodgkin's or Hodgkin's), sickle cell anemia. |
| Other | Angiomata, angiogenesis associated with the neoplasms. |

XI. Synthetic Techniques

Various synthetic techniques are known for preparing the compounds of the present invention. For example, compounds wherein the residue of a therapeutic and/or diagnostic agent is directly linked to the 6-position of a compound of formula I (i.e. in which X is L-T and L is a direct bond) can be prepared by reducing a corresponding Co (III) compound of formula I to form a nucleophilic Co (I) compound and treating this Co (I) compound with a residue of a therapeutic and/or diagnostic agent (or a derivative thereof) comprising a suitable leaving group, such as a halide. Similarly, compounds wherein X is L-T and L is other than a direct bond can be prepared by preparing a nucleophilic Co (I) species as described herein above, and reacting it with a linker comprising a suitable leaving group, such as a halide. Peptides and amino acids can be attached to the 6-position by reducing a corresponding Co (III) compound of formula I to form a nucleophilic Co (I) compound, and treating the Co (I) compound with a suitable alkylating agent comprising an amino acid or peptide.

Coupling of L-T to the ribose moiety at K or $G^1$ may be accomplished by activating the natural OH at either K or $G^1$ with a suitable reagent such as succinic anhydride, to yield a reactive group such as a carboxylate. This technique is described in detail in Toraya, Bioinorg. Chem. 4:245-255, 1975.

Coupling of L-T to M can be accomplished using techniques described in detail in Jacobsen, Anal. Biochem. 113: 164-171, 1981.

The residue of vitamin $B_{12}$ or its analog can be prepared by any suitable means known in the art. For example, a monocarboxylic acid or dicarboxylic acid of cobalamin can be prepared as disclosed in U.S. Pat. No. 5,739,313. These compounds can be prepared by the mild acid hydrolysis of cyanocobalamin, which has been shown to yield a mixture of mono-, a dicarboxylic acid and one tricarboxylic acid. These carboxylic acids are derived from the propionamide side chains designated b, d- and e-, as discussed hereinabove, which are more susceptible to hydrolysis than the amide groups on acetamide side chains a-, c- and g-. The b-, d-, and e-monocarboxylic acids can be separated by column chromatography. L. Anton et al., J. Amer. Chem. Soc.,102, 2215 (1980). See, also, J B. Armitage et al., L Chem. Sot., 3349 (1953); K. Bernhauer, Biochem. Z., 344, 289 (1966); H. P. C. Hogenkamp et al., Biochemistry, 14, 3707 (1975); and L. Ellenbogen, in "Cobalamin," Biochem. and Pathophysiol, B. Babior, ed., Wiley, NY (1975) at chapter 5.

Additional compounds, intermediates, and synthetic preparations thereof are disclosed, for example, in Hogenkamp, H. et al., *Synthesis and Characterization of nido-Carborane-Cobalamin Conjugates*, Nucl. Med. & Biol., 2000, 27, 89-92; Collins, D., et al., *Tumor Imaging Via Indium III-Labeled DTPA-Adenosylcobalamin*, Mayo Clinic Proc., 1999, 74:687-691.

XII. Diagnostic Compositions and Administration

Preferred modes of administration of the TC- or IF-binding carriers and therapeutic and/or diagnostic agents are parenteral, intravenous, intrademnal, intra-articular, intrasynovial, intrathecal, intra-arterial, intracardiac, intramuscular, subcutaneous, intraorbital, intracapsular, intraspinal, intrasternal, topical, transdermal patch, via rectal, vaginal or urethral suppository, peritoneal, percutaneous, nasal spray, surgical implant, internal surgical paint, infusion pump, or via catheter. In one embodiment, the agent and carrier are administered in a slow release formulation such as an implant, bolus, microparticle, microsphere, nanoparticle or nanosphere. For standard information on pharmaceutical formulations, see Ansel, et al., *Pharmaceutical Dosage Forms and Drug Delivery Systems*, Sixth Edition, Williams & Wilkins (1995).

The TC- or IF-binding carriers/therapeutic and/or diagnostic agents can, for example, be administered intravenously or intraperitoneally by infusion or injection. Solutions of the substance can be prepared in water, optionally mixed with a nontoxic surfactant. Dispersions can also be prepared in glycerol, liquid polyethylene glycols, triacetin and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the substance which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, normal saline, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, benzyl alcohol, sorbic acid, thimerosal and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the substance in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Injectable solutions are particularly advantageous for local administration of the therapeutic composition. In particular, parenchymal injection can be used to deliver the therapeutic composition directly to a tumorous growth. Intra-articular injection is a preferred alternative in cases of arthritis where the practitioner wishes to treat one or only a few (such as 2-6) joints. Additionally, the therapeutic compounds are injected directly into lesions (intra-lesion administration) in appropriate cases. Intradermal administration is an alternative for dermal lesions.

The therapeutic compound is optionally administered topically by the use of a transdermal therapeutic system (see, Barry, Dermatological Formulations, (1983) p. 181 and literature cited therein). Transdermal drug delivery (TDD) has several advantages over oral delivery. When compared to oral delivery, TDD avoids gastrointestinal drug metabolism, reduces first pass effects and provides a sustained release of drugs for up to seven days (Elias, et al. *Percutaneous Absorption: Mechanisms-Methodology-Drug Delivery*; Marcel Dekker, NY: 1, 1989). This method is especially useful with many therapeutic proteins that are susceptible to gastrointestinal degradation and exhibit poor gastrointestinal uptake. When compared to injections, TDD eliminates the associate pain and the possibility of infection. While such topical delivery systems have been designed largely for transdermal administration of low molecular weight drugs, by definition they are capable of percutaneous delivery. They can be readily adapted to administration of the therapeutic compounds of the invention by appropriate selection of the rate-controlling microporous membrane. Topical application can also be achieved by applying the compound of interest, in a cream, lotion, ointment, or oil based carrier, directly to the skin. Typically, the concentration of therapeutic compound in a cream, lotion or oil is 1-2%.

For drug targeting to lung tissue, the therapeutic compound is formulated into a solution, suspension, aerosol or particulate dispersion appropriate for application to the pulmonary system. The therapeutic agent may be inhaled via nebulizer, inhalation capsule, inhalation aerosol, nasal solution, intratracheal as a solution via syringe, or endotracheal tube as an aerosol or via as a nebulizer solution. Aerosols are prepared using an aqueous aerosol, liposomal preparation or solid particles containing the compound. A nonaqueous (e.g. fluorocarbon propellant) suspension could be used. Sonic nebulizers are preferred because they minimize exposing the therapeutic compound to shear, which can result in degradation of the compound.

Delivery of the cobalamin conjugates of the instant invention by the mucosal route also offers an attractive administration alternative. The prototype formulation for nasal solutions will contain the vitamin $B_{12}$ conjugate dissolved in a suitable aqueous or non-aqueous solvent such as propylene glycol, an antioxidant and aromatic oils as flavoring agents. The formulation may also contain suitable propellant(s).

For ophthalmic applications, the therapeutic compound is formulated into solutions, suspensions and ointments appropriate for use in the eye. For opthalnic formulations, see Mitra (ed.), Ophthalmic Drug Delivery Systems, Marcel Dekker, Inc., New York, N.Y. (1993), and also Havener, W. H., Ocular Pharmacology, C.V. Mosby Co., St. Louis (1983).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949. The amount of the substance required for use in treatment, prophylaxis and/or diagnosis will vary not only with the particular salt selected but also with the route of administration, the nature of the condition being treated and the age and condition of the patient and will be ultimately at the discretion of the attendant physician or clinician.

In general, however, a suitable dose for nuclear medicine (using a radioactive therapeutic and/or diagnostic agent) will be in the range of from about 0.1 ug/patient to about 1000 ug/patient, from about 0.5 to about 500 ug/patient, or from 1 ug/patient to about 100 ug/patient.

A suitable dose for imaging medicine (using a paramagnetic therapeutic and/or diagnostic agent) will be in the range of from about 0.1 mg/patient to about 100 mg/patient, from about 0.5 to about 50 mg/patient, or from 1 mg/patient to about 10 mg/patient.

For therapeutic applications, a suitable dose will be in the range of from about 0.05 picograms/kilogram to about 100 mg/kg, from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day. The substance is conveniently administered in unit dosage form; for example, containing 5 to 1000 mg, conveniently 10 to 750 mg, most conveniently, 50 to 500 mg of active ingredient per unit dosage form.

Ideally, the substance should be administered to achieve peak plasma concentrations of from about 0.05 to about 100 µM, preferably, about 1 to 50 µM, most preferably, about 2 to about 30 µM. This may be achieved, for example, by the intravenous injection of a 0.005 to 10% solution of the substance, optionally in saline, or orally administered as a bolus containing about 0.5-250 mg of the substance. Desirable blood levels may be maintained by continuous infusion to provide about 0.01-5.0 mg/kg/hr or by intermittent infusions containing about 0.4-15 mg/kg of the substance.

The substance may conveniently be presented in a single dose or as divided doses administered at appropriate intervals, for example, as two, three, four or more sub-doses per day.

The cobalamin conjugates may be administered orally in combination with a pharmaceutically acceptable vehicle such as an inert diluent or an edible carrier. They may be enclosed in hard or soft shell gelatin capsules, may be compressed into tablets, or may be incorporated directly with the food of the patient's diet. For oral therapeutic administration, the substance may be combined with one or more excipients and used in the form of ingestible tablets, buccal tablets, troches, capsules, elixirs, suspensions, syrups, wafers, and the like. Such compositions and preparations should contain at least 0.1% of the substance. The percentage of the compositions and preparations may, of course, be varied and may conveniently be between about 2 to about 60% of the weight of a given unit dosage form. The amount of substance in such therapeutically useful compositions is such that an effective dosage level will be obtained.

Tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the substance may be incorporated into sustained-release preparations and devices.

Sublingual tablets are designed to dissolve very rapidly. Examples of such formulations include ergotamine tartrate, isosorbide dinitrate, isoproterenol HCl. The formulation of these tablets contain, in addition to the drug, a limited number of soluble excipients, usually lactose and powdered sucrose, but occasionally dextrose and mannitol. The process of making sublingual tablets involves moistening the blended powder components with an alcohol-water solvent system containing approximately 60% alcohol and 40% water.

In addition to the cobalamin conjugate, the prototype formulation for sublingual tablets may contain a binder such as povidone or HPMC, diluents such as lactose, mannitol, starch or cellulose, a disintegrant such as pregelatinized or modified starch, lubricants such as magnesium stearate, stearic acid or hydrogenated vegetable oil, a sweetener such as saccharin or sucrose and suitable flavoring and coloring agents.

It is preferred that the TC- or IF-binding carrier and the therapeutic and/or diagnostic agent be administered parenterally, not orally, to increase bioavailability and delivery to proliferative tissue.

The TC- or IF-binding carrier and the therapeutic and/or diagnostic agent can be administered in the course of surgical or medical treatment, prophylaxis and/or diagnosis of the afflicted site. For example, the TC- or IF-binding carrier and therapeutic and/or diagnostic agent can be positioned directly at the site of proliferation during the course of surgery either by painting the formulation onto the surface of the afflicted area (with or without a carrier matrix) or by depositing a bolus of material in a suitable matrix that is released into the afflicted area over time. In another embodiment, the TC- or IF-binding carrier and the therapeutic and/or diagnostic agent are administered directly into the proliferative mass via injection or catheter.

In yet another embodiment, a TC- or IF-binding carrier attached to a radiodiagnostic can be used in lymphoscintigraphy, to identify the sentinel or closest lymph node to an afflicted site of hyperproliferation for investigation of the existence or possible spread of disease, for example, as occurs in metastasis. In this embodiment, the TC-binding or IF-binding agent and radiodiagnostic are administered, preferably via injection, to a site circumferential to the afflicted area in the skin. The radiodiagnostic is preferentially absorbed into the sentinal node or proliferating cells due to the presence of the TC-binding or IF-binding agent, and then is monitored in its normal course of travel in the lymphatic system to the closest lymph node. Colored dye is sometimes also added to help identify the sentinel node. The node is then removed and checked for the presence of abnormally proliferating cells.

In one embodiment, the agent and carrier are administered in a slow release formulation such as an implant, bolus, microparticle, microsphere, nanoparticle or nanosphere. Nonlimiting examples of sustained release compositions include semi-permeable polymer matrices in the form of shaped articles, e.g., films, microcapsules or microspheres. Sustained release matrices include, for example, polylactides (U.S. Pat. No. 3,773,919), copolymers of L-glutamic acid and γ-ethyl-L-glutamate (Sidman et al., Biopolymers 22:547-556, 1983), or poly-D-(−)-3-hydroxybutyric acid (EP 133,988). Sustained release compositions also include one or more liposomally entrapped compounds of formula I. Such compositions are prepared by methods known per se, e.g., as taught by Epstein et al. Proc. Natl. Acad. Sci. USA 82:3688-3692, 1985. Ordinarily, the liposomes are of the small (200-800 Å) unilamellar type in which the lipid content is greater than about 30 mol % cholesterol, the selected proportion being adjusted for the optimal therapy.

A number of sustained-release implants are known in the art. Most implants are "matrix" type, and comprise an active compound dispersed in a matrix of a carrier material. The carrier material may be either porous or non-porous, solid or semi-solid, and permeable or impermeable to the active compound. Matrix devices are typically bio-degradable, i.e., they slowly erode after administration. Alternatively, matrix devices may be nondegradable, and rely on diffusion of the active compound through the walls or pores of the matrix. Matrix devices are preferred for the applications contemplated herein.

Thus, in one embodiment the invention provides a surgical implant for localized delivery of an anti-proliferative agent comprising the cobalamin conjugate of the present invention, and a biodegradable binder. The implant preferably is capable of releasing and delivering the cobalamin conjugate to substantially all of an area of clear margin that results from a surgical resection, and is also preferably capable of releasing the cobalamin conjugate at a substantially constant rate. In another embodiment the invention provides a method of delivering a therapeutic and/or diagnostic agent to an area of clear margin following a surgical resection comprising (i) providing an implant comprising a TC- or IF-binding carrier linked to a therapeutic and/or diagnostic agent and a biodegradable binder; and (ii) placing the implant into a void created by surgical resection.

The surgical implant can exhibit a variety of forms. In one embodiment the implant is a bolus, comprising a viscous and deformable material capable of being shaped and sized before or during implantation to complement a void created by a surgical resection, and sufficiently deformable upon implantation to contact substantially all of an area of clear margin. The surgical implant can also comprising a plurality of capsules that can be poured into the void created by a surgical resection. These capsules will contain the cobalamin conjugate and a suitable binder. Because they are flowable, they can be poured into the void created by a surgical lumpectomy, and thereby contact substantially all of the areas of clear margin.

Many suitable compositions for the implant are known and can be used in practicing the invention. Such compositions are described in, for example, Chasin et al., Biodegradable Polymers as Drug Delivery Systems, Marcel Dekker Inc., NY, ISBN 0-8247-8344-1. Preferable compositions are pharmaceutically acceptable, biodegradable, and meet the particular release profile characteristics that are required to achieve the administration regime involved.

The implant typically comprises a base composition that acts as a matrix to contain and hold the contents of the implant together. The base composition can, in turn, comprise one or more constituents. Examples of base compositions include polymers and copolymers of anhydrides, orthoester, lactic acid, glycolic acid, dioxonane, trimethylene carbonate, $\epsilon$-caprolactone, phosphazene and glyceryl monostearate.

In one embodiment the base composition for the matrix comprises a polyanhydride, which can be synthesized via the dehydration of diacid molecules by melt condensation. Degradation times can be adjusted from days to years according to the hydrophobicity of the monomer selected. The materials degrade primarily by surface erosion and possess excellent in vivo compatibility. In one embodiment the polyanhydride is formed from sebasic acid and hexadecandioic acid (poly(SA-HDA anhydride). Wafer-like implants using this base composition have been approved for use in brain cancer, as Giadel®, by Guilford Pharmaceuticals.

The implant optionally can comprise erosion and biodegradation enhancers that facilitate the erosion of the matrix, the dissolution of the core composition, or the uptake of the core composition via metabolic processes. Particularly suitable erosion and biodegradation enhancers are biodegradable in biological fluids, and biocompatible. Hydrophilic constituents are typical, because they are capable of enhancing the erosion of the implant in the presence of biological fluids. For example, K. Juni et al., Chem. Pharm. Bull., 33, 1609 (1985) disclose that the release rate of bleomycin from polylactic acid microspheres is greatly enhanced by incorporating fatty acid esters into the microspheres. Other exemplary hydrophilic constituents are described, for example, in Wade & Weller, Handbook of pharmaceutical Excipients (London: Pharmaceutical Press; Washington D.C.: American Pharmaceutical Ass'n 1995), and include the polyethylene glycols ("PEGs"), propylene glycol ("PG"), glycerin, and sorbitol.

Surfactants further enhance the erosion of the matrix and the release of the drug. Surfactants are generally capable of increasing the wettability and the solubility of the base composition in biological fluids, and thereby causing the disintegration and erosion of the implant. Surfactants can also help to break down the core composition matrix when, for example, the method of forming the dosage form has reduced the solubility of any of the constituents. Surfactants can also improve the uptake of the dosage forms into the bloodstream.

Suitable surfactants include, for example, glyceryl based surfactants such as glyceryl monooleate and glyceryl monolaurate, poloxamers such as Pluronic F127, and polysorbates such as polyoxyethylene sorbitan monooleate ("Tween 80").

The implant could also include components that retard the rate at which the implant erodes or biodegrades (erosion and/or biodegradation retardants). Hydrophobic constituents are a particularly suitable class of components for retarding the rate at which the outer layer biodegrades. Suitable hydrophobic constituents are described, for example, in the Handbook of Pharmaceutical Excipients, the disclosure from which being hereby incorporated by reference. Exemplary hydrophobic constituents include peanut oil, olive oil and castor oil.

Any proportions or types of constituents can be chosen that effectively achieve a desired release profile, and thereby carry out the prescribed administration regime. The most desirable base compositions generally release the drug substantially continuously, and biodegrade completely shortly after substantially all of the drug has been effectively released. The amount of drug included in the dosage forms is determined by the total amount of the drug to be administered, and the rate at which the drug is to be delivered. The total amount of the drug to be delivered is determined according to clinical requirements, and in keeping with the considerations that typically inform drug dosage determinations in other contexts. The surgical implant also can contain one or more other drugs having therapeutic efficacy in the intended applications, such as an antibiotic, an analgesic or an anesthetic.

XIII. Controlled Release Formulations

The TC- or IF-binding carrier and therapeutic and/or diagnostic agent is optionally administered in a controlled release formulation, which can be a degradable or nondegradable polymer, hydrogel, organogel, or other physical construct that modifies the bioabsorption, half life or biodegradation of the TC- or IF-binding carrier/therapeutic and/or diagnostic agent. The controlled release formulation can be a material that is painted or otherwise applied onto the afflicted site, either internally or externally. In one embodiment, the invention provides a biodegradable bolus or implant that is inserted into the pocket created by surgical resection of a tumor, or directly into the tumor itself. In another example, the controlled release formulation can be applied to a psoriatic lesion, eczema, atopic dermatitis, lichen planus, wart, pemphigus vulgaris, actinic keratosis, basal cell carcinoma or squamous cell carcinoma. The controlled release formulation can likewise be applied to a blood vessel to treat or prevent restenosis, retinopathies or atherosclerosis. The controlled release formulation with appropriated selected therapeutic and/or diagnostic agent can be used to coat a transplanted organ or tissue to prevent rejection. It can alternatively be implanted or otherwise applied near the site of rheumatoid arthritis.

The field of biodegradable polymers has developed rapidly since the synthesis and biodegradability of polylactic acid was first reported in 1966 by Kulkami et al. "Polylactic acid for surgical implants," Arch. Surg., 93, 839. Several other polymers are now known to biodegrade, such as polyanhydrides and polyorthoesters, which take advantage of labile backbone linkages (see: Domb et al. *Macromolecules,* 22, 3200, 1989; and Heller et al. *Biodegradable Polymers as Drug Delivery Systems,* Dekker, NY: 1990). Several polymers which degrade into naturally occurring materials have also been described, such as crosslinking gelatin, hyaluronic acid (della Valle et al. U.S. Pat. No. 4,987,744 and U.S. Pat. No. 4,957,744) and polyaminoacids (Miyake et al., 1974), which spurred the usage of polyesters by Holland et al. *Controlled Release,* 4, 155, 1986 and alph-hydroxy acids (i.e. lactic acid and glycolic acid), which remain the most widely used biodegradable materials for applications ranging from closure devices (sutures and staples) to drug delivery systems (Smith et al. U.S. Pat. No. 4,741,337; Spilizeqski et al. *J. Control. Rel.,* 2, 197, 1985).

These polymers can be tailored to degrade at a desired rate and with a desired kinetics by selecting the appropriate monomers, method of preparation and molecular weight. Differences in crystallinity of the monomer can alter the polymeric degradation rate. Due to the relatively hydrophobic nature of most polymers, actual mass loss can begin with the oligomeric fragments that are small enough to be water soluble; hence, even the initial molecular weight can influence the degradation rate.

Hydrogels can be used in controlled release formulations. Such polymers are formed from macromers with a polymerizable, non-degradable, region that is separated by at least one degradable region. For example, the water soluble, non-degradable, region can form the central core of the macromer and have at least two degradable regions which are attached to the core, such that upon degradation, the non-degradable regions (in particular a polymerized gel) are separated. Specifically, as disclosed in U.S. Pat. No. 5,626,863 to Hubbell et al., the macromers are PEG-oligoglycolyl-acrylates, with the appropriate end caps to permit rapid polymerization and gelation. Acrylates can be polymerized readily by several initiating systems such as eosin dye, ultraviolet or visible light. The polyethyleneglycol (PEG) is highly hydrophilic and biocompatible. The oligoglycolic acid is a poly(a-hydroxy acid) which can be readily degraded by hydrolysis of the ester linkage into glycolic acid, a nontoxic metabolite. Other chain extensions include polylactic acid, polycaprolactone, polyorthoesters, polyanhydrides and polypeptides. This entire network can be gelled into a biodegradable network that can be used to entrap and homogeneously disperse water-soluble drugs for delivery at a controlled rate. Further, the gel can entrap particulate suspensions of water-insoluble drugs. (See also: U.S. Pat. No. 4,591,496 to Cohen et al. (Process for Making Systems for the Controlled Release of Macromolecules); U.S. Pat. No. 5,545,442 to Van Savage et al. (Method for Using a Radiation Cured Drug Release Controlling Membrane); U.S. Pat. No. 5,330,768 to Park et al. (Controlled Drug Delivery Using Polymer/Pluronic Blends); U.S. Pat. No. 5,122,367 to Ron et al. (Polyanhydride Bioerodible Controlled Release Implants for Administration of Stabilized Growth Hormone); U.S. Pat. No. 5,545,409 to Laurencin et al. (Delivery System for Controlled Release of Bioactive Factors); U.S. Pat. No. 5,629,009 to Laurencin et al. (Delivery System for Controlled Release of Bioactive Factors).

Alternatively, delivery of biologically active substances, both in vitro and in vivo, via encapsulation has been well described in the prior art. U.S. Pat. No. 4,352,883 to Lim et al. entitled "Encapsulation of Biological Material" discloses the encapsulation of proteins within a membrane by suspending the protein in an aqueous medium containing a water-soluble gum that can be reversibly gelled to form the suspension into droplets. These droplets can be gelled further into discrete, shape-retaining, water insoluble temporary capsules with the aid of a solution of multivalent cations. The temporary capsules then can be further wrapped by an ionically cross-linking surface layer to form a semipermeable membrane around the capsules that is permeable to small molecules but impermeable to larger molecules. Microencapsulations of glycoproteins have also been well described. U.S. Pat. No. 4,324,683 to Lim et al. entitled "Encapsulation of Labile Biological Material" encapsulates a glycoprotein by a two-step interfacial polymerization process to form capsules with well-controlled porosity. The microcapsules serve to protect the active substances from attack by microorganisms and from any immunological response. U.S. Pat. No. 5,718,921 to Mathiowitz et al. (Microspheres Comprising Polymer and Drug Dispersed There Within) discloses a method to encapsulate relatively temperature-labile drugs into a microsphere.

Several methods have been developed to reversibly encapsulate biologically active substances. One that can be applied both to in vitro and in vivo studies has been described in U.S. Pat. No. 4,900,556 by Wheatley et al. entitled "System for Delayed and Pulsed Release of Biologically-Active Substances." In this disclosed system, the biologically-active substance can be released either at a constant rate over a period of time or in discrete pulses. The biologically active materials are entrapped within liposomes encapsulated within semipermeable microcapsules or permeable polymeric matrix. Release of the desired materials is governed by the permeability of both the liposome and the surrounding matrix (the matrix integrity is directly proportional to the liposome integrity); the permeability of the liposome can be engineered by modifying the composition and the method for making the liposome to produce liposome that are sensitive to specific stimuli such as temperature, pH or light. For example, by including a phospholipase that degrades the liposome within some or all of the liposomes or the surrounding matrix, the liposome can be destabilized and broken down over a period of time. Other systems have been developed, e.g. U.S. Pat. No. 4,933,185 by Wheatley et al., which utilize a core made up of a polymer (such as an ionically cross-linked polysaccharide with calcium alginate or chitin) around which there is an ionically bound skin (such as a polycationic skin of poly-L-lysine) whose integrity is dependent on the core polymer. With an impermeable skin, when the core polymer can be degraded by enzymes (such as alginase from the bacteria, chitinase or hydrolase), there is a sudden release of biologically active substance from the core. Alternatively, the skin can be partially permeable for a gradual release of drug upon degradation of the core.

Nanoparticles are especially useful in the delivery of drugs parenterally or intravenously such that the delivery device is small with a long circulating half-life. A number of injectable drug delivery systems have been investigated, including microcapsules, microparticles, liposomes and emulsions. The major obstacle for these delivery systems is the rapid clearance of the materials from the blood stream by the macrophages of the reticuloendothelial system (RES). For example, polystyrene particles as small as sixty nanometers in diameter are cleared from the blood within two to three minutes. Liposomal drug delivery systems have also been extensively studied for this application because they were expected to freely circulate in the blood. Coating of the liposomes with poly(ethylene glycol) (PEG) increased the half-life of the carriers due to PEG's hydrophobic chains which reduced its protein absorption and thus its RES uptake. U.S. Pat. No. 5,543,158 to Gref et al. (biodegradable Injectable Nanoparticles) describes a carrier system specifically targeted towards carriers suitable for intravenous delivery with a controlled release mechanism with modified polyglycols.

U.S. Pat. No. 5,626,862, U.S. Pat. No. 5,651,986 and U.S. Pat. No. 5,846,565 to Brem et al. (Controlled Local Delivery of Chemotherapeutic Agents for Treating Solid Tumors) discloses the use of these carriers for the specific delivery of chemotherapeutic agents to increase bioavailability. Therefore, the devices act as reservoirs that release drugs over an extended period of time while at the same time preserves the bioactivity and bioavailability of the agent. U.S. Pat. No. 5,286,763 to Gerhard et al. (Bioerodible Polymers for Drug Delivery in Bone) further discloses that bioerodible polymers can be used to deliver chemotherapeutic agents directly into the bone. Cohen et al. U.S. Pat. No. 5,562,099 (Polymeric Microparticles Containing Agents for Imaging) discusses the usage of these carriers as contrast agents. The polymeric microparticle is filled with contrast agents for enhanced imaging.

Books describing methods of controlled delivery that are appropriate for the delivery of the TC- or IF-binding carriers/ therapeutic and/or diagnostic agents of the present invention include: Robert S. Langer, Donald L. Wise, editors; *Medical applications of controlled release* (Volumes 1 and 2); Boca Raton, Fla.: CRC Press, 1984; and William J. M. Hrushesky, Robert Langer, and Felix Theeuwes, editors; *Temporal control of drug delivery* (series); New York: New York Academy of Sciences, 1991.

Nonlimiting examples of U.S. Patents that describe controlled release formulations are: U.S. Pat. No. 5,356,630 to Laurencin et al. (Delivery System for Controlled Release of Bioactive Factors); U.S. Pat. No. 5,797,898 to Santini, Jr. et al. (Microchip Drug Delivery Devices); U.S. Pat. No. 5,874, 064 to Edwards et al. (Aerodynamically Light Particles for Pulmonary Drug Delivery); U.S. Pat. No. 5,548,035 to Kim et al. (Biodegradable Copolymer as Drug Delivery Matrix Comprising Polyethyleneoxide and Aliphatic Polyester Blocks); U.S. Pat. No. 5,532,287 to Savage et al. (Radiation Cured Drug Release Controlling Membrane); U.S. Pat. No. 5,284,831 to Kahl et al. (Drug Delivery Porphyrin Composition and Methods); U.S. Pat. No. 5,741,329 to Agrawal et al. (Methods of Controlling the pH in the Vicinity of Biodegradable Implants); U.S. Pat. No. 5,820,883 to Tice et al. (Methods for Delivering Bioactive Agents into and Through the Mucosally-Associated Lymphoid Tissues and Controlling Their Release); U.S. Pat. No. 5,955,068 to Gouin et al. (Biodegradable polyanhydrides Derived from Dimers of Bile Acids, and Use Thereof as Controlled Drug Release Systems); U.S. Pat. No. 6,001,395 to Coombes et al. (Polymeric Lamellar Substrate Particles for Drug Delivery); U.S. Pat. No. 6,013,853 to Athanasiou et al. (Continuous Release Polymeric Implant Carriers); U.S. Pat. No. 6,060,582 to Hubbell et al. (Photopolymerizable Biodegradable Hydrogels as Tissue Contacting Materials and Controlled Release Carriers); U.S. Pat. No. 6,113,943 to Okada et al. (Sustained-Release Preparation Capable of Releasing a Physiologically Active Substance); and PCT Publication No. WO 99/59548 to Oh et al. (Controlled Drug Delivery System Using the Conjugation of Drug to Biodegradable Polyester); U.S. Pat. No. 6,123,861 (Fabrication of Microchip Drug Delivery Devices); U.S. Pat. No. 6,060,082 (Polymerized Liposomes Targeted to M cells and Useful for Oral or Mucosal Drug Delivery); U.S. Pat. No. 6,041,253 (Effect of Electric Field and Ultrasound for Transdermal Drug Delivery); U.S. Pat. No. 6,018,678 (Transdermal protein delivery or measurement using low-frequency sonophoresis); U.S. Pat. No. 6,007,845 Nanoparticles And Microparticles Of Non-Linear Hydrophilic-Hydrophobic Multiblock Copolymers; U.S. Pat. No. 6,004,534 Targeted Polymerized Liposomes For Improved Drug Delivery; U.S. Pat. No. 6,002,961 Transdermal Protein Delivery Using Low-Frequency Sonophoresis; U.S. Pat. No. 5,985,309 Preparation Of Particles For Inhalation; U.S. Pat. No. 5,947,921 Chemical And Physical Enhancers And Ultrasound For Transdermal Drug Delivery; U.S. Pat. No. 5,912,017 Multi-wall Polymeric Microspheres; U.S. Pat. No. 5,911,223 Introduction Of Modifying Agents Into Skin By Electroporation; U.S. Pat. No. 5,874,064 Aerodynamically Light Particles For Pulmonary Drug Delivery; U.S. Pat. No. 5,855,913 Particles Incorporating Surfactants For Pulmonary Drug Delivery; U.S. Pat. No. 5,846,565 Controlled Local Delivery Of Chemotherapeutic Agents For Treating Solid Tumors; U.S. Pat. No. 5,837,752 Semi-Interpenetrating Polymer Networks; U.S. Pat. No. 5,814,599 Transdermal Delivery Of Encapsulated Drugs; U.S. Pat. No. 5,804,178 Implantation Of Cell-Matrix Structure Adjacent Mesentery, Oinentum Or Peritoneum Tissue; U.S. Pat. No. 5,797,898 Microchip Drug Delivery Devices; U.S. Pat. No. 5,770,417 Three-Dimensional Fibrous Scaffold Containing Attached Cells For Producing Vascularized Tissue In Vivo; U.S. Pat. No. 5,770,193 Preparation Of Three-Dimensional Fibrous Scaffold For Attaching Cells To Produce Vascularized Tissue In Vivo; U.S. Pat. No. 5,762,904 Oral Delivery Of Vaccines Using Polymerized Liposomes; U.S. Pat. No. 5,759,830 Three-Dimensional Fibrous Scaffold Containing Attached Cells For Producing Vascularized Tissue In Vivo; U.S. Pat. No. 5,749,847 Delivery Of Nucleotides Into Organisms By Electroporation; U.S. Pat. No. 5,736,372 Biodegradable Synthetic Polymeric Fibrous Matrix Containing Chondrocyte For In Vivo Production Of A Cartilaginous Structure; U.S. Pat. No. 5,718,921 Microspheres Comprising Polymer And Drug Dispersed There Within; U.S. Pat. No. 5,696,175 Preparation Of Bonded Fiber Structures For Cell Implantation; U.S. Pat. No. 5,667,491 Method For Rapid Temporal Control Of Molecular Transport Across Tissue; U.S. Pat. No. 5,654,381 Functionalized Polyester Graft Copolymers; U.S. Pat. No. 5,651,986 Controlled Local Delivery Of Chemotherapeutic Agents For Treating Solid Tumors; U.S. Pat. No. 5,629,009 Delivery System For Controlled Release Of Bioactive Factors; U.S. Pat. No. 5,626,862 Controlled Local Delivery Of Chemotherapeutic Agents For Treating Solid Tumors; U.S. Pat. No. 5,593,974 Localized Oligonucleotide Therapy; U.S. Pat. No. 5,578,325 Nanoparticles And Microparticles Of Non-Linear Hydrophilic-Hydrophobic Multiblock Copolymers; U.S. Pat. No. 5,562,099 Polymeric Microparticles Containing Agents For Imaging; U.S. Pat. No. 5,545,409 Delivery System For Controlled Release Of Bioactive Factors; U.S. Pat. No. 5,543, 158 Biodegradable Injectable Nanoparticles; U.S. Pat. No. 5,514,378 Biocompatible Polymer Membranes And Methods Of Preparation Of Three Dimensional Membrane Structures; U.S. Pat. No. 5,512,600 Preparation Of Bonded Fiber Structures For Cell Implantation; U.S. Pat. No. 5,500,161 Method For Making Hydrophobic Polymeric Microparticles; U.S. Pat. No. 5,487,390 Gas-filled polymeric microbubbles for ultrasound imaging; U.S. Pat. No. 5,399,665 Biodegradable polymers for cell transplantation; U.S. Pat. No. 5,356,630 Delivery system for controlled release of bioactive factors; U.S. Pat. No. 5,330,768 Controlled drug delivery using polymer/pluronic blends; U.S. Pat. No. 5,286,763 Bioerodible polymers for drug delivery in bone; U.S. Pat. No. 5,149,543 Ionically cross-linked polymeric microcapsules; U.S. Pat. No. 5,128,420 Method of making hydroxamic acid polymers from primary amide polymers; U.S. Pat. No. 5,122,367 Polyanhydride bioerodible controlled release implants for administration of stabilized growth hormone; U.S. Pat. No. 5,100, 668 Controlled release systems containing heparin and growth factors; U.S. Pat. No. 5,019,379 Unsaturated polyanhydrides; U.S. Pat. No. 5,010,167 Poly(amide-and imide-co-anhydride) for biological application; U.S. Pat. No. 4,948, 587 Ultrasound enhancement of transbuccal drug delivery; U.S. Pat. No. 4,946,929 Bioerodible articles useful as implants and prostheses having predictable degradation rates; U.S. Pat. No. 4,933,431 One step preparation of poly(amide-anhydride); U.S. Pat. No. 4,933,185 System for controlled release of biologically active compounds; U.S. Pat. No.

4,921,757 System for delayed and pulsed release of biologically active substances; U.S. Pat. No. 4,916,204 Pure polyanhydride from dicarboxylic acid and coupling agent; U.S. Pat. No. 4,906,474 Bioerodible polyanhydrides for controlled drug delivery; U.S. Pat. No. 4,900,556 System for delayed and pulsed release of biologically active substances; U.S. Pat. No. 4,898,734 Polymer composite for controlled release or membrane formation; U.S. Pat. No. 4,891,225 Bioerodible polyanhydrides for controlled drug delivery; U.S. Pat. No. 4,888,176 Controlled drug delivery high molecular weight polyanhydrides; U.S. Pat. No. 4,886,870 Bioerodible articles useful as implants and prostheses having predictable degradation rates; U.S. Pat. No. 4,863,735 Biodegradable polymeric drug delivery system with adjuvant activity; U.S. Pat. No. 4,863,611 Extracorporeal reactors containing immobilized species; U.S. Pat. No. 4,861,627 Preparation of multiwall polymeric microcapsules; U.S. Pat. No. 4,857,311 Polyanhydrides with improved hydrolytic degradation properties; U.S. Pat. No. 4,846,786 Bioreactor containing suspended, immobilized species; U.S. Pat. No. 4,806,621 Biocompatible, bioerodible, hydrophobic, implantable polyimino carbonate article; U.S. Pat. No. 4,789,724 Preparation of anhydride copolymers; U.S. Pat. No. 4,780,212 Ultrasound enhancement of membrane permeability; U.S. Pat. No. 4,779,806 Ultrasonically modulated polymeric devices for delivering compositions; U.S. Pat. No. 4,767,402 Ultrasound enhancement of transdermal drug delivery; U.S. Pat. No. 4,757,128 High molecular weight polyanhydride and preparation thereof; U.S. Pat. No. 4,657,543 Ultrasonically modulated polymeric devices for delivering compositions; U.S. Pat. No. 4,638,045 Non-peptide polyamino acid bioerodible polymers; U.S. Pat. No. 4,591,496 Process for making systems for the controlled release of macromolecules.

The invention will now be illustrated by the following non-limiting Examples.

EXAMPLES

Poly-L-lysine hydrobromide (MW 500-2000) and (MW 1000-4000), adenosine, 1-ethyl-3(3'-dimethylaminopropyl) carbodiimide, trifluoroacetic acid, trifluoroacetic anhydride, 2,2,2-trifluoroethylamine hydrochloride and 1-hydroxybenzotriazole were purchased from Sigma Chemical Co. Sephodex-G-10 was purchased from Pharmacia Biotech, Inc. Thin layer chromatography (TLC) silica gel plates were obtained from Eastman Kodak Co. Solvents and other reagents were obtained in the highest purity available. Cyanocobalamin-b, d and e monocarboxylic acid and the b,d-dicarboxylic acid were prepared as described before (Anton, D. L., Hogenkamp, H. P. C., Walker, T. E. and Matwiyoff, N. A., Carbon-13 nuclear magnetic resonance studies of the monocarboxylic acids of cyanocobalamin. Assignments of the b-, d-, and e-monocarboxylic acids, *J. Am. Chem. Soc.*, 102, 2215-2219 (1980)). 5'chloro-5'-deoxyadenosine was synthesized by the method of Kikugawa and Ichino (Kikugawa, K. and Ichino, M., *Tetrahedron Lett.*, 87 (1971)). The adenosylcobalamin-monocarboxylic acid was prepared as described before (Hogenkamp, H. P. C., Chemical synthesis and properties of analogs of adenosylcobalamin, *Biochemistry*, 13, 2736-2740 (1974)).

Example 1

Figure 3:
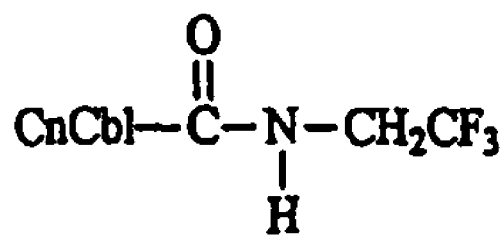
FIG. 3 illustrates a synthesis of representative compounds of the invention (8, 9) wherein a residue of a compound of formula I is linked to a non-metallic radionuclide (e.g., Fluorine-18).
Figure 3:
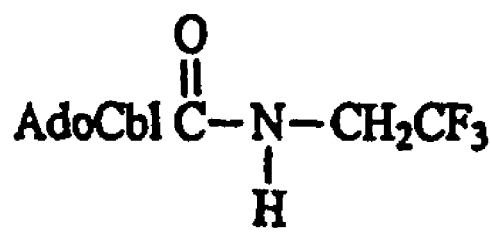

Cyanotrifluoroethylamidocobalamin (4, 5 and 6, FIG. 3).

Separate reaction mixtures containing 600 mg (~0.4 mmol) of the b, d and e-cyanocobalamin monocarboxylic acids (compounds 1, 2, 3, FIG. 3), hydroxybenzo-triazole 540 mg (4 mmol), 1-ethyl-3(3'-dimethylaminopropyl) carbodiimide 768 mg (4 mmol) and 2,2,2-trifluoroethylamino hydrochloride 678 mg (5 mmol) were dissolved in 50 mL water and the pH adjusted to 6.8 with 1N NaOH. The progress of the reactions was monitored by TLC using 2-propanol-NH$_4$OH-water (7:1:2) as the solvent. After 2 hours incubation at room temperature, the mixtures were extracted into 92% aqueous phenol. The phenol layers were extensively washed with water to remove the water-soluble reagents. One volume of acetone and three volumes of ether were then added to the phenol phases and the desired fluorocobalamins were back extracted into water. The aqueous phases were extracted three times with ether to remove residual phenol. The solutions were concentrated on a rotary evaporator and the fluorocobalamins crystallized from aqueous acetone. Yields 4, 600 mg; 5, 540 mg; 6, 470 mg.

Example 2

Adenosyltrifluoroethylamidocobalamins (8 and 9, FIG. 3).

Separately the b- and e-cyanotrifluoroethylamidocobalamins (compounds 5, 6) 500 mg (~0.33 mmol) were reduced with sodium borohydride to their cobalt (I) forms, which in turn were reacted with 5'chloro-5'-deoxyadenosine as described before (Hogenkamp, H. P. C., Chemical synthesis and properties of analogs of adenosylcobalamin, *Biochemistry*, 13, 2736-2740 (1974)). The reaction mixtures were acidified to a pH of 3 with 1N HCl and applied to separate columns of A6 50×2 (200-400 mesh, pH 3.0). The columns were washed with water and the desired adenosylcobalamins eluted with 0.1 M sodium acetate pH 6A. After desalting by extraction into phenol as described above, both 8 and 9 were isolated as red powders. Yields 315 mg and 320 mg respectively.

Example 3

Figure 4:
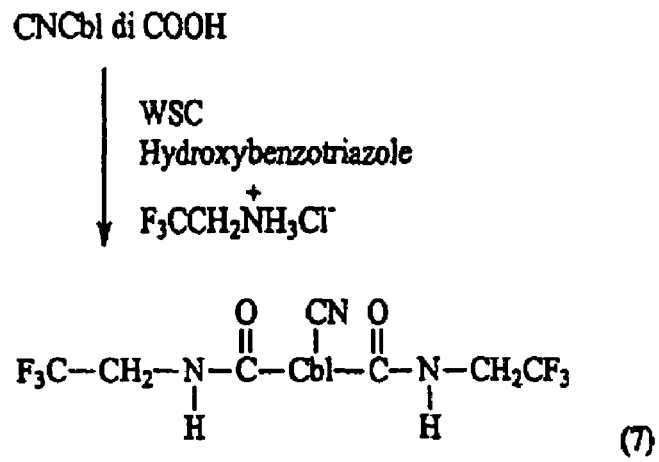
FIG. 4 illustrates a synthesis of a compound of the present invention (7) wherein a residue of a compound of formula I is linked to a non-metallic radionuclide (e.g., Fluorine-18) through a linker.

Cyano-bis-trifluoroethylamidocobalamin (7, FIG. 4).

A reaction mixture containing cyanocobalamin-b, d-dicarboxylic acid (540 mg, ~0.36 mmol) was reacted with 2,2,2-trifluoroethylamine hydrochloride 678 mg (5 mmol) as described above, compound 7 was crystallized from aqueous acetone. Yield 630 mg.

Example 4

Figure 5:
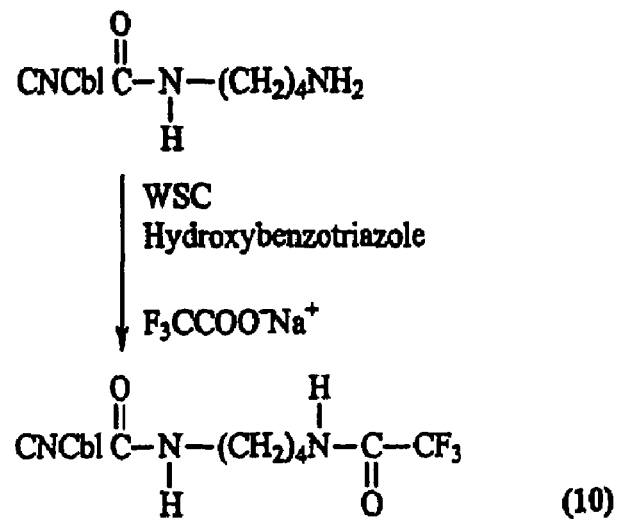
FIG. 5 illustrates a synthesis of a compound of the present invention (10) wherein a residue of a compound of formula I is linked to a non-metallic radionuclide (e.g., Fluorine-18) through a linker.

Cyano-b-trifluoroacetamido butylamide cobalamin (10, FIG. 5).

Cyanocobalamin-b-(9-aminobutyl) amide (600 mg, ~0.4 mmol) was prepared as described by Collins, D. A. and Hogenkamp, H. P. C., Transcobalamin II receptor imaging via radiolabeled diethylenetriaminepentaacetate cobalamin analogs, *J. Nucl. Med.*, 38, 717-723 (1997), hydroxybenzotriazole 540 mg (4 mmol), 1-ethyl-3(3'-dimethylamino-propyl) carbodiimide 768 mg (4 mmol) and sodium trifluoroacetate (680 mg, 5 mmol) were dissolved in 50 mL water and the pH adjusted to 6.2 with 1N NaOH. After incubation at room temperature for 5 hours, the reaction mixture was desalted as described above. The resulting aqueous solution was purified by column chromatography (A6, 50×2, 200-400 mesh, pH 3.0) and the pass through collected. The solution was concentrated and compound 10 was crystallized from aqueous acetone. Yield 315 mg.

Example 5

Cyanotrifluoroacetyl polylysine cobalamin (11, FIG. 6).

Poly-L-lysine hydrobromide (MW 500-2000) 500 mg, cyanocobalamin-b-carboxylic acid 300 mg (~0.2 mmol), hydroxybenzotriazole (338 mg, 2.5 mmol) and 1-ethyl-3(3'-dimethylaminopropyl)carbodiimide 480 mg (2.5 mmol) were dissolved in 10 mL of water and the pH adjusted to 6.5 with 1N NaOH. After incubation at room temperature for 4 hr, the reaction mixture was purified by chromatography (Sephodex G-10, 40×3 cm), which was eluted with water. The red eluents that also reacted with ninhydrin were pooled and freeze dried. The freeze-dried preparation was dissolved in 10 mL saturated sodium bicarbonate and reacted with 1 mL of trifluoroacetic anhydride for 1 hr. The preparation was again purified by chromatography and lyophilized to yield 490 mg of compound 11 as a fluffy powder.

Example 6

Cyanocobalamin-b-(4-aminobutyl)amide.

A mixture containing cyanocobalamin-b-carboxylic acid (1.0 g, 0.6 mmol), hydroxybenzotriazole (0.81 g, 6 mmol) and 1,4-diaminobutane dihydrochloride (4.8 g, 30 mmol) in 100 mL of water was adjusted to pH 7.8. 1-Ethyl-3-(3'-dimethylaminopropyl)carbodiimide (1.26 g, 6.6 mmol) was then added, the pH was adjusted to 6.4 and the reaction stirred at room temperature for 24 h. TLC on silica gel using n-butanol-acetic acid water (5:2:3) showed the reaction to be complete. Cyanocobalamin-b-(4-aminobutyl)amide was extracted into 92% aqueous phenol and the phenol layer was washed several times with equal volumes of water. To the phenol extract were added 3 volumes of diethylether and 1 volume of acetone. The desired cobalamin was removed from the organic phase by several extractions with water. The combined aqueous layers were extracted three times with diethylether to remove residual phenol, concentrated to approximately 20 mL in vacuo and crystallized from aqueous acetone. Yield 955 mg, 92%.

Example 7

Cyanocobalamin-b-(4-aminobutyl)amide DTPA.

Cyanocobalamin-b-(4-aminobutyl) amide (500 mg), 0.3 mmol) was dissolved in 30 mL saturated sodium bicarbonate and treated with solid DTPA dianhydride (1.2 g, 3.4 mmol). The progress of the reaction was monitored by TLC on PEI plates using n-butanol-acetic acid-water (5:2:3) as the solvent. After 30 min incubation at room temperature a second 1.2 g of the dianhydride was added. After two additional additions of dianhydride with adjustments of the pH to 8.2 the reaction mixture was incubated overnight. Cyanocobalamin-DPTA product was then extracted into 92% aqueous phenol, desalted, purified by AG-1×2 200-400 mesh in acetate form, eluting with 1.0 M acetic acid and washed with water. The preparation was evaporated to dryness in vacuo and isolated as a glass. Yield 460 mg, 77%. The cyanocobalamin-DTPA adduct behaves as a polyanion on paper electrophoresis in 0.1 M sodium phosphate buffer pH 7.1.

Example 8

Methylcobalamin-b-(4-aminobutyl)amide.

Methylcobalamin-b-carboxylic acid (1.0 g, 0.6 mmol) was reacted with diaminobutane dihydrochloride as described above for the cyano derivative. The cobalamin was purified by extraction through phenol (see above) and the resulting aqueous solution was concentrated in vacuo. This solution was chromatographed on AGI-X2 200-400 mesh in the acetate form (20×2.5 cm) and the pass through collected. The pass through was concentrated to approximately 20 mL and the desired cobalamin crystallized from aqueous acetone. Yield 920 mg, 88%. Unreacted methylcobalamin-b-carboxylic acid was eluted with 1 M acetic acid, concentrated and crystallized from aqueous acetone. Yield 60 mg, 6%.

Example 9

Methylcobalamin-b-(4-aminobutyl)amide DTPA.

Methylcobalamin-b-(4-aminobutyl)amide (500 mg, 0.3 mmol) was dissolved in 30 mL saturated sodium bicarbonate and reacted with solid DTPA dianhydride as described above. The methyl cobalamin-DTPA product was extracted into 92% aqueous phenol, desalted, purified by AG-1×2 200-400 mesh in acetate form, eluting with 1.0 M acetic acid and washed with water, evaporated to dryness in vacuo and isolated as a glass. Yield 600 mg, 96%.

Example 10

Adenosylcobalamin-b-(4-aminobutyl)amide.

Adenosylcobalamin-b-carboxylic acid (500 mg, 0.3 mmol) was reacted with diaminobutane dihydrochloride (2.4 mg, 15 mmol) as described above. The cobalamin was purified by extraction through phenol (see above). The resulting aqueous solution was concentrated in vacuo and applied to AG-50 X2, 200-400 mesh, in the hydrogen form (20×25 cm). The column was washed thoroughly with water to remove hydroxybenzotriazole and the desired cobalamin eluted with 1 M ammonium hydroxide. After an additional extraction through phenol, adenosylcobalamin-b-(4-aminobutyl)amide was isolated as a glass. Yield 366 mg, 77%.

Example 11

Adenosylcobalamin-b-(4-aminobutyl)amide DTPA.

Adenosylcobalamin-b-(4-aminobutyl)amide (366 mg, 0.23 mmol) was dissolved in 30 mL saturated sodium bicarbonate and treated with solid DTPA dianhydride (1.0 g, 2.8 mmol) as described above. The cobalamin was purified through phenol (see above). The resulting aqueous solution was concentrated, extracted into 92% aqueous phenol, desalted, purified by AG-1×2 200-400 mesh in acetate form, eluting with 0.5 M acetic acid and washed with water. The solution was evaporated to dryness in vacuo and adenosylcobalamin-b-(4-aminobutyl)amide DTPA isolated as a glass. Yield 400 mg, 80%.

Example 12

Chelation of Radionuclides.

Under dim light, 1000 μg of methyl-, adenosyl-, and cyanocobalamin-b-(4-aminobutyl)amide-DTPA were separately dissolved in 200 μL of normal saline. Next, 500 μCi of Indium-111 or 250 μCi of Gadolinium-153 were added to the cobalamin-DTPA solutions. The reactions were carried out at room temperature and room air. For the chelation of technetium, the dissolved cobalamin DTPA complexes were separately placed into sealed 2 mL vials. Next, 200 μL of stannous chloride solution (1000 μg/mL normal saline) was added to each vial. The vials were purged with nitrogen gas for 5 minutes. After this time, 1-5 mCi of Technetium-99m was added to the $N_2$ purged vials. Each vial underwent further nitrogen purging for 5 minutes. All chelation reactions were mixed gently for 5 minutes.

Control mixtures of 1000 μg of cyanocobalamin were dissolved in 200 μL of normal saline. Cyanocobalamin was mixed with Tc-99m at room temperature and room air, as well as within nitrogen purged vials containing 200 µL of the described stannous chloride solution. Additionally, the cobalamin-DTPA complexes underwent Tc-99m labeling in open vials at room air in the absence of the stannous chloride.

Example 13

Interaction with Intrinsic Factor and Transcobalamin Proteins.

Under dim light, 1000 µg of the non-labeled methyl-, adenosyl-, and cyanocobalamin-b-(4-aminobutyl)amide-DTPA, as well as 1000 µg of cyanocobalamin and DTPA (Sigma, St. Louis, Mo. 63178), were separately dissolved in 10 mL of normal saline at room temperature. Each of the five 1000 µg/10 mL samples was stored in sealed, aluminum-wrapped 10 mL vials to prevent exposure to light. No buffers were added to the solutions. The pH of the solutions, measured by a Beckman 40 pH meter (Beckman Instruments, Fullerton, Calif.): Cyanocobalamin=5.75, DTPA=3.78; cyano, methyl and adenosylcobalamin-DTPA analogues were 5.75, 6.10, and 6.19, respectively.

To assess in vitro binding to Intrinsic Factor (IF) and Transcobalamins (TC), the intrinsic factor blocking antibody (IFBA) and Unsaturated vitamin $B_{12}$ Binding Capacity (UBBC) assays were performed with serum randomly obtained from five patients being evaluated for pernicious anemia at the Mayo Clinic. The IFBA and UBBC assays were first performed for clinical purposes as previously described by V. F. Fairbanks et al., *Mayo Clin. Proc.*, 58, 203 (1983); Intrinsic Factor Blocking Antibody ($^{57}$Co) Radioassay-Package insert, Diagnostic Products Corp.; D. Grossowicz et al., *Proc. Exp. Biol.*, 109, 604 (1962) and C. Gottlieb et al., *Blood*, 25, 6 (1965).

Next, the serum from the same five patients underwent modified IFBA and UBBC assays. Specifically, 1 µL of the five previously described solutions was separately incubated with purified IF or serum, to potentially saturate all IF and TC-binding sites.

After incubation for 20 minutes at room temperature and for another 20 minutes at 4° C., 500 µl of the stock (1000 µg/l) Cobalt-57-cyanocobalamin (Mallinckrodt Medical, Inc., St. Louis, Mo. 63134) solution was added and the usual IFBA and UBBC protocols were then followed. All supernatant activity was counted for four minutes on a gamma counter (Micromedix 10/20, Huntsville, Ala. 35805). The results are shown in Table 3.

The IFBA assay demonstrated that DTPA does not significantly bind to IF (values less than the negative reference), whereas cyanocobalamin and the cobalamin-DTPA analogs do, in varying degrees, competitively inhibit Co-57 cyanocobalamin from binding to intrinsic factor. By using the counts of the Clinical run divided into the counts of the five solutions, the efficacy of binding to intrinsic factor can be estimated. The averaged percent binding of the five solutions to IF was: cyanocobalamin=92.5%; methyl-cobalamin-b-(4-aminobutyl)-amide-DTPA=63.2%; cyanocobalamin-b-(4-aminobutyl)-amide-DTPA=52.9%; adenosylcobalamin-b-(4-aminobutyl)-amide-DTPA=41.0% and 0.8% for DTPA. This is in contrast to the disclosure in Houts (U.S. Pat. No. 4,465,775) that the (b)-monocarboxylic acid of vitamin $B_{12}$ and its radioiodinated derivative exhibit very low binding to IF.

Likewise the averaged percent binding of the five solutions to the transcobalamin proteins was: cyanocobalamin=100%, methylcobalamin-b-(4-aminobutyl)amide-DTPA=94.0%, adenosylcobalamin-b-(4-aminobutyl)amide-DTPA=90.4%, cyanocobalamin-b-(4-aminobutyl)amide-DTPA=66.4% and 3.6% for DTPA.

Thus, the attachment of DTPA to vitamin $B_{12}$ does alter its binding to the carrier proteins. As expected, non-labeled cyanocobalamin had the greatest affinity for IF and the transcobalamin proteins. Methylcobalamin-b-(4-aminobutyl)amide-DTPA was next, followed by adenosylcobalamin-b-(4-aminobutyl)amide-DTPA, and finally cyanocobalamin-b-(4-aminobutyl)amide-DTPA. There was also some nonspecific binding of DTPA to the carrier proteins (0.8% and 3.6%).

Example 14

Cyano-and Adenosyl cobalamin-spermine

Cyanocobalamin-b-monocarboxylic acid or adenosyl cobalamin-b monocarboxylic acid were separately reacted with 5 fold excess of spermine in the presence of a 10 fold excess of hydroxybenzotriazole and 1-ethyl-3(3'-dimethylaminopropyl)carbodiimide. The progress of the reaction was monitored by TLC on silica gel plates using isopropanol-ammonium hydroxide-water (7:1:2) as the solvent. After incubation at room (for 24 h) temperature (in the dark) the reaction mixtures were extracted into 90% aqueous phenol. The phenol phase was washed with water (7x) to remove the water soluble reagents. Finally the cobalamins were back extracted into water after the addition of one volume of acetone and three volumes of ether. The aqueous solutions were evaporated to dryness and stirred with acetone to remove traces of hydroxybenzotriazole. The cobalamins were isolated as red powders.

Example 15

Cyano- and Adenosyl cobalamin-spermine DTPA Conjugate

The cobalamin-spermine derivatives were separately dissolved in sodium bicarbonate (saturated aqueous solution) and reacted with ten fold excess of DTPA bis-anhydride. The reaction was followed by TLC on PEI plates using the same solvent. A second ten fold excess of the dianhydride was added after 2 hr. After incubation for 24 hr. at room temperature the reaction mixtures were extracted with aqueous phenol as described above, the phenol phases were extensively washed with water. The desired products were isolated as red powders as described above. UV-visible specters copy showed the correct spectra for the cyano-and adenosyl cobalamin derivatives.

Example 16

Cyanocobalamin-Poly L-Lysine-DTPA Conjugate.

Poly-L-lysine hydrobromide (Sigma no. P0879), degree of polymerization~11 units, molecular weight range 1000-4000 (500 mg) was dissolved in water (20 mL). Cyanocobalamin-b-monocarboxylic acid (150 mg, ~100 µmol), 1-ethyl-3 (3'-dimethylaminopropyl) carbodiimide (480 mg, 2.5 mmol) and hydroxybenzotriazole (338 mg, 2.5 mmol) were added. The pH of the mixture was adjusted and maintained at approximately 8 with 1 N sodium hydroxide. The progress of the reaction was monitored by thin layer chromatography on silica gel sheets using isopropanol:ammonium hydroxide:water (7:1:2) as the developing agent.

Upon completion of the reaction, the mixture was applied to a column of Sephadex G-10 (3×40 cm). The column was eluted with water and 2 mL fractions were collected. The red eluents that reacted with ninhydrin were pooled and freeze dried (i.e., lyophilized).

Recovery of the cyanocobalamin-poly-L-lysine complex (about 70%) was obtained. The cyanocobalamin-poly-L-lysine complex was dissolved in water (10 mL) and a saturated solution of sodium bicarbonate (10 mL) and DTPA bisanhydride (Sigma) (375 mg, 1 mmol) were added.

The progress of the reaction was monitored by TLC as described above. The cyanocobalamin-poly-L-lysine-DTPA conjugate was purified on Sephadex G-10 as described above. The final product was freeze dried and isolated as a red powder.

Example 17

Cyanocobalamin-Poly L-Lysine-DTPA Conjugate.

Poly-L-lysine (Sigma no. 8954) degree of polymerization 8 units, molecular weight range 500-2000 (500 mg) was dissolved in water (20 mL). Cyanocobalamin-b-monocarboxylic acid (150 mg, ~100 μmmols), 1-ethyl-3 (3'-dimethylaminopropyl) carbodiimide (480 mg, 2.5 mmol) and hydroxybenzotriazole (338 mg, 2.5 mmol) were added. The pH of the mixture was adjusted and maintained at approximately 8 with 1 N sodium hydroxide. The progress of the reaction was monitored by thin layer chromatography on silica gel sheets using isopropanol-ammonium hydroxide-water (7:1:2) as the developing agent.

Upon completion of the reaction, the mixture was applied to a column of Sephadex G-10 (3×40 cm). The column was eluted with water and 2 mL fractions were collected. The red eluents that reacted with ninhydrin were pooled and freeze dried (i.e., lyophilized).

Recovery of the cyanocobalamin-poly-L-lysine complex (about 70%) was obtained. The cyanocobalamin-poly-L-lysine complex was dissolved in water (10 mL) and a saturated solution of sodium bicarbonate (10 mL) and DTPA bisanhydride (Sigma) (375 mg, 1 mmol) were added.

The progress of the reaction was monitored by TLC as described above. The cyanocobalamin-poly-L-lysine-DTPA conjugate was purified on Sephadex G-10 as described above. The final product was freeze dried and isolated as a red powder.

Example 18

Imaging Data.

In vitro unsaturated $B_{12}$ binding capacity (UBBC) has demonstrated that cyanocobalamin-poly-L-lysine, cyanocobalamin-poly-L-lysine-polyDTPA compounds have in vitro biological activity that is 92% and 43.4% when compared to cyanocobalamin. Comparison of cyanocobalamin-DTPA to cyanocobalamin was 66.4% (Transcobalamin II receptor imaging via radiolabeled diethylene-triaminepentaacetate cobalamin analogs, J. Nucl. Med., 38, 717-723 (1997); also described in U.S. Pat. No. 5,739,313). The specific activity has been increased from 300 μCi in the cobalamin mono-DTPA compounds to 4.5 mCi with the cobalamin poly-L-lysine-polyDTPA complex (D. A. Collins, H. P. C. Hogenkamp, M W Gebard, Tumor Imaging Indium-111-labeled DTPA-adenosylcobalamin, Mayo Clinic Proceedings, 1999; 74; 687-691; Biodistribution of Radiolabeled Adenosylcobalamin in Humans, Review of 30 patents submitted to Mayo Clinic Proceedings). This should improve tumor-to-background ratio, which can be evaluated in murine tumor models. Attachment of either the adenosyl and methyl group as the beta ligand should improve the biological activity as it did with the cyanocobalamin mono-DTPA compound (Transcobalamin II receptor imaging via radiolabeled diethylene-triaminepentaacetate cobalamin analogs, J. Nucl. Med., 38, 717-723 (1997); also described in U.S. Pat. No. 5,739,313).

Example 19

Figure 7:
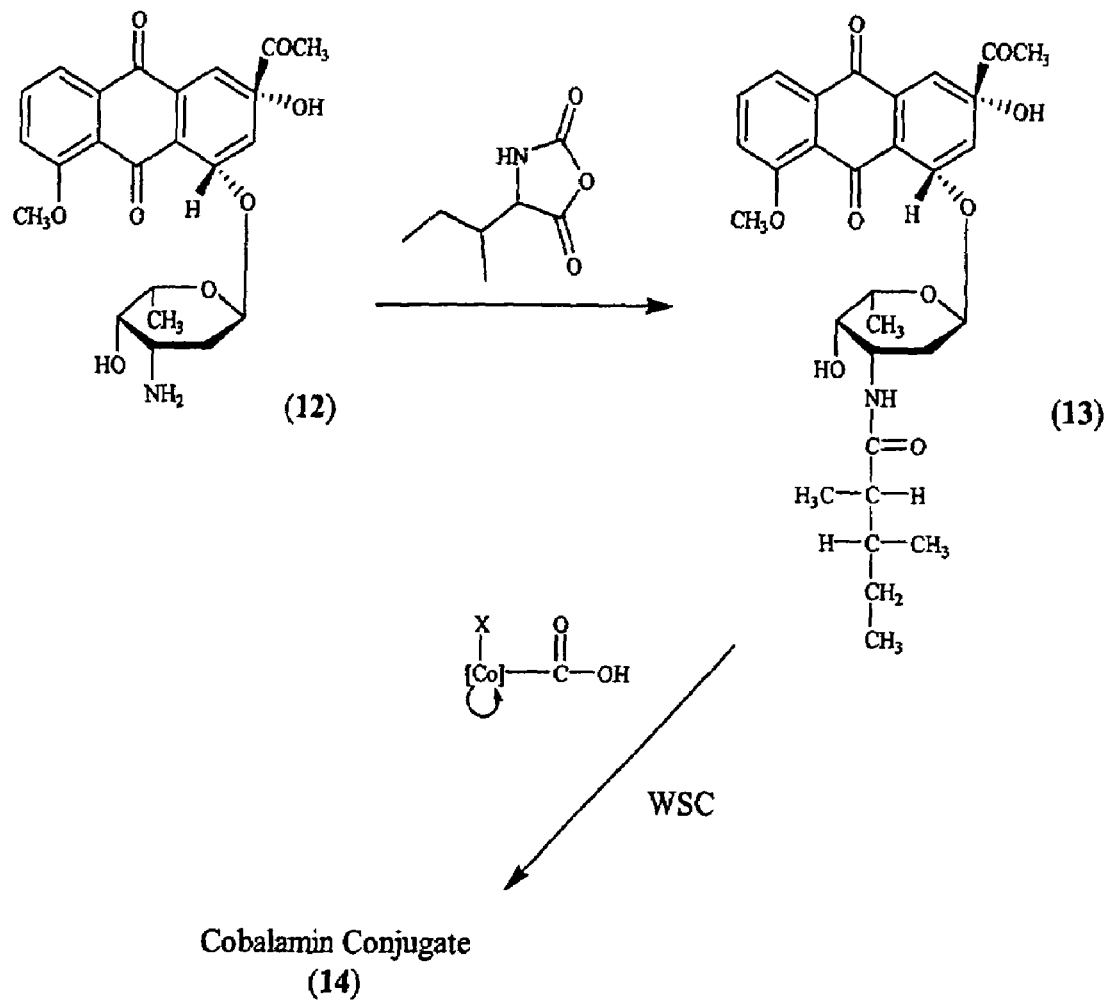
FIG. 7 illustrates a synthesis of a compound wherein a residue of a vitamin $B_{12}$ analog is attached to a linker, which is bound to a residue of a chemotherapeutic agent.

Proposed Synthesis of Daunorubicin- and Doxorubicin-Cobalamin Conjugates (FIG. 7).

Modification of the carbohydrate moiety (daunosamine) of daunorubicin (12) with L-leucine can be accomplished by reacting daunorubicin HCl (0.5 g) in 100 mL borate buffer pH=10 (containing KCl) with L-leucine-carboxyanhydride (1 mmole in 5 mL acetone) at 0° C. under nitrogen. After reaction for 5 minutes at 0° C., the mixture can be acidified to pH 3.5 with $H_2SO_4$, stirred for 15 minutes and adjusted to pH=7 to give the desired L-leucyl daunorubicin (13). Reaction of (13) with a cobalamin-mono or dicarboxylic acid in the presence of a water-soluble carbodiimide and hydroxybenzo-triazole will yield the daunorubicin-cobalamin conjugate (14). These conjugates can be isolated via the usual phenol extraction, extensive washing of the phenol phase with water and finally displacing the cobalamin-conjugates from the phenol phase into water by the addition of acetone and diethyl ether.

Modification of doxorubicin should be similar (Ger. Patent 1,813,518, Jul. 10, 1969; Chem Abstracts, 71, 91866 (1969)). D. Deprez-Decampaneere, M Mosquelier, R. Bourain and A. Trosect, Curr. Chemother. Proc., Int. Congr. Chemother., 10th, p. 1242 (1978) have found that N-(L-leucyl) daunorubicin but not the D isomer was hydrolyzed in vivo to regenerate daunorubicin. See, "Doxorubicin, Anticancer Antibiotics," Federico Arcamone, Medicinal Chemistry, Vol. 17, Academic Press, 1981.

The invention has been described with reference to various specific and preferred embodiments and techniques. However, it should be understood that many variations and modifications may be made while remaining within the spirit and scope of the invention.

What is claimed is:

1. A compound of the formula (I):

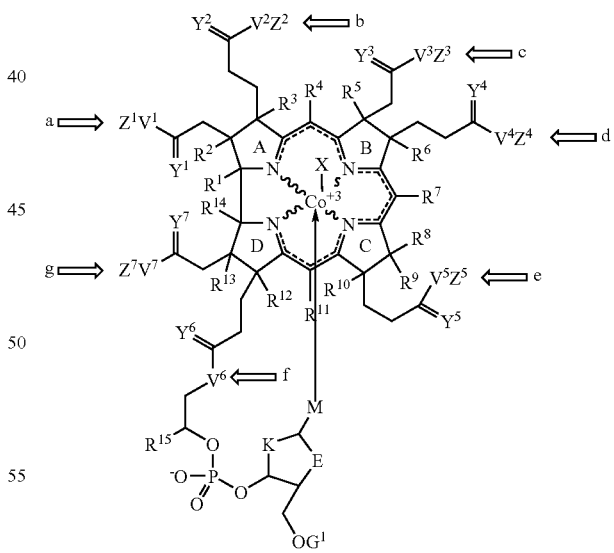

or its enantiomer, diastereomer or its pharmaceutically acceptable salt, wherein:
  (i) the wavy line in the chemical structure indicates either a dative or covalent bond such that there are three dative Co—N bonds and one covalent Co—N bond, wherein, in the case of the dative bond, the valence of nitrogen is completed either with a double bond with an adjacent ring carbon or with a hydrogen;

(ii) the dotted line in the chemical structure indicates either a double or single bond such that the double bond does not over-extend the valence of the element and, in the case of a single bond, the valence is completed with hydrogen;

(iii) X is hydrogen, cyano, halogen, haloalkyl, NO, $NO_2$, $NO_3$, phosphonate, $PR^{15}R^{16}R^{17}$, $NH_2$, $NR^{15}R^{16}$, OH, $OR^{15}$, $SR^{15}$, SCN, $N_3$, $OC(O)R^{15}$, $C(O)_2R^{15}$, $C(O)R^{15}$, $OC(O)NR^{15}R^{16}$, $C(O)_2NR^{15}R^{16}$, $C(O)NR^{15}R^{16}$, $P(O)_2OR^{15}$, $S(O)_2R^{15}$, a purine or pyrimidine nucleoside or nucleoside analog, adenosyl, 5-FU, alkyl, alkenyl, alkynyl, aryl, aralkyl, alkaryl, amino acid, peptide, protein, carbohydrate, heteroalkyl, heterocycle, heteroaryl or alkylheteroaryl;

(iv) M is a monovalent heterocycle or heteroaromatic, which is capable of binding to the adjacent sugar ring, and forming a dative bond with $Co^{+3}$;

(v) K is O, S, $NJ^1$, C(OH)H, $CR^{100}R^{101}$ or $C(R^{100})V^8Z^8$;

(vi) E is O or S;

(vii) $G^1$ is hydrogen, alkyl, acyl, silyl, phosphate or L-T;

(viii) $Y^1, Y^2, Y^3, Y^4, Y^5, Y^6$ and $Y^7$ independently are O, S or $NJ^2$;

(ix) $V^1, V^2, V^3, V^4, V^5, V^6, V^7$ and $V^8$ independently are O, S, $NJ^3$, $CR^{102}R^{103}$ or a direct bond;

(x) $Z^1, Z^2, Z^3, Z^4, Z^5, Z^7$ and $Z^8$ independently are $R^{104}$ or L-T;

(xi) each L is independently a direct bond or linker, of a singular molecular weight, to one or more T moieties, and that does not significantly impair the ability of the TC- or IF-binding carrier to bind to a transcobalamin receptor, optionally when bound to a transport protein;

(xii) each T independently comprises the residue of a diagnostic agent effective for the diagnosis of a proliferative disorder, optionally bound though a chelating moiety;

(xiii) at least one of $Z^1, Z^2, Z^3, Z^4, Z^5, Z^7, Z^8$, K and $G^1$ is L-T;

(xiv) $J^1, J^2$ and $J^3$ independently are hydrogen, alkyl, alkenyl, alkynyl, alkaryl, cycloalkyl, aryl, cycloaryl, heteroalkyl, heterocycle, heteroaryl, hydroxyl, alkoxy or amine;

(xv) $R^1, R^2, R^3, R^4, R^5, R^6, R^7, R^8, R^9, R^{10}, R^{11}, R^{12}, R^{13}$ and $R^{14}$ independently are hydrogen, lower alkyl, lower alkenyl, lower alkynyl, lower cycloalkyl, heteroalkyl, heterocyclic, lower alkoxy, azido, amino, lower alkylamino, halogen, thiol, $SO_2$, $SO_3$, carboxylic acid, $C_{1-6}$ carboxyl, hydroxyl, nitro, cyano, oxime or hydrazine;

(xvi) $R^{13}$ and $R^{14}$ optionally can form a double bond;

(xvii) $R^{15}, R^{16}$ and $R^{17}$ are independently hydrogen, alkyl, alkenyl, alkynyl, aryl, alkaryl or aralkyl group, heteroalkyl, heterocycle or heteroaromatic; and (xviii) $R^{100}, R^{101}, R^{102}, R^{103}$, and $R^{104}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl or amino;

(xix) wherein at least one of Y, R, G, E, K, M and V is not as it is found in natural vitamin $B_{12}$; and (xx) wherein at least one -L-T is independently a poly-L-lysine-NR'$(CH((CH_2)_4$ —NHR')CONR')$_m$R', wherein each R' is independently hydrogen, lower alkyl or T; and m is 2-20.

2. A compound of the formula (I):

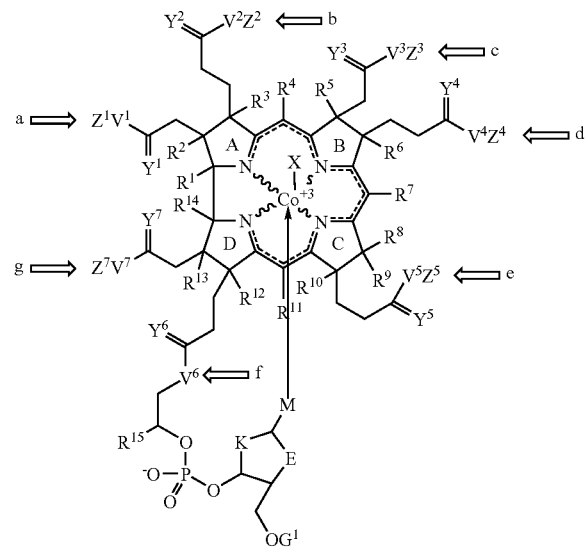

or its enantiomer, diastereomer or its pharmaceutically acceptable salt, wherein:

(i) the wavy line in the chemical structure indicates either a dative or covalent bond such that there are three dative Co—N bonds and one covalent Co—N bond, wherein, in the case of the dative bond, the valence of nitrogen is completed either with a double bond with an adjacent ring carbon or with a hydrogen;

(ii) the dotted line in the chemical structure indicates either a double or single bond such that the double bond does not over-extend the valence of the element and, in the case of a single bond, the valence is completed with hydrogen;

(iii) X is hydrogen, cyano, halogen, haloalkyl, NO, $NO_2$, $NO_3$, phosphonate, $PR^{15}R^{16}R^{17}$, $NH_2$, $NR^{15}R^{16}$, OH, $OR^{16}$, $SR^{15}$, SCN, $N_3$, $OC(O)R^{15}$, $C(O)_2R^{15}$, $C(O)R^{15}$, $OC(O)NR^{15}R^{16}$, $C(O)_2NR^{15}R^{16}$, $C(O)NR^{15}R^{16}$, $P(O)_2OR^{15}$, $S(O)_2R^{15}$, a purine or pyrimidine nucleoside or nucleoside analog, adenosyl, 5-FU, alkyl, alkenyl, alkynyl, aryl, aralkyl, alkaryl, amino acid, peptide, protein, carbohydrate, heteroalkyl, heterocycle, heteroaryl or alkyiheteroaryl;

(iv) M is a monovalent heterocycle or heteroaromatic, which is capable of binding to the adjacent sugar ring, and forming a dative bond with $Co^{+3}$;

(v) K is O, S, $NJ^1$, C(OH)H, $CR^{100}R^{101}$ or $C(R^{100})V^8Z^8$;

(vi) E is O or S;

(vii) $G^1$ is hydrogen, alkyl, acyl, silyl, phosphate or L-T;

(viii) $Y^1, Y^2, Y^3, Y^4, Y^5, Y^6$ and $Y^7$ independently are O, S or $NJ^2$;

(ix) $V^1, V^2, V^3, V^4, V^5, V^6, V^7$ and $V^8$ independently are O, S, $NJ^3$, $CR^{102}R^{103}$ or a direct bond;

(x) $Z^1, Z^2, Z^3, Z^4, Z^5, Z^7$ and $Z^8$ independently are $R^{104}$ or L-T;

(xi) each L is independently a direct bond or linker, of a singular molecular weight, to one or more T moieties, and that does not significantly impair the ability of the TC- or IF-binding carrier to bind to a transcobalamin receptor, optionally when bound to a transport protein;

(xii) each T independently comprises the residue of a diagnostic agent effective for the diagnosis of a proliferative disorder, optionally bound though a chelating moiety;

(xiii) at least one of $Z^1$, $Z^2$, $Z^3$, $Z^4$, $Z^5$, $Z^7$, $Z^8$, K and $G^1$ is L-T;

(xiv) $J^1$, $J^2$ and $J^3$ independently are hydrogen, alkyl, alkenyl, alkynyl, alkaryl, cycloalkyl, aryl, cycloaryl, heteroalkyl, heterocycle, heteroaryl, hydroxyl, alkoxy or amine;

(xv) $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ independently are hydrogen, lower alkyl, lower alkenyl, lower alkynyl, lower cycloalkyl, heteroalkyl, heterocyclic, lower alkoxy, azido, amino, lower alkylamino, halogen, thiol, $SO_2$, $SO_3$, carboxylic acid, $C_{1-6}$ carboxyl, hydroxyl, nitro, cyano, oxime or hydrazine;

(xvi) $R^{13}$ and $R^{14}$ optionally can form a double bond;

(xvii) $R^{15}$, $R^{16}$ and $R^{17}$ are independently hydrogen, alkyl, alkenyl, alkynyl, aryl, alkaryl or aralkyl group, heteroalkyl, heterocycle or heteroaromatic; and (xviii) $R^{100}$, $R^{101}$, $R^{102}$, $R^{103}$, and $R^{104}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl or amino;

(xix) wherein at least one of Y, R, G, E, K, M and V is not as it is found in natural vitamin $B_{12}$; and (xx) wherein at least one -L-T is independently a polyamine residue of the formula—NR'(alkylene-NR')$_n$ alkyleneNR'R', wherein each R' is independently hydrogen, lower alkyl or T and n is 1-20.

3. A compound of the formula (I):

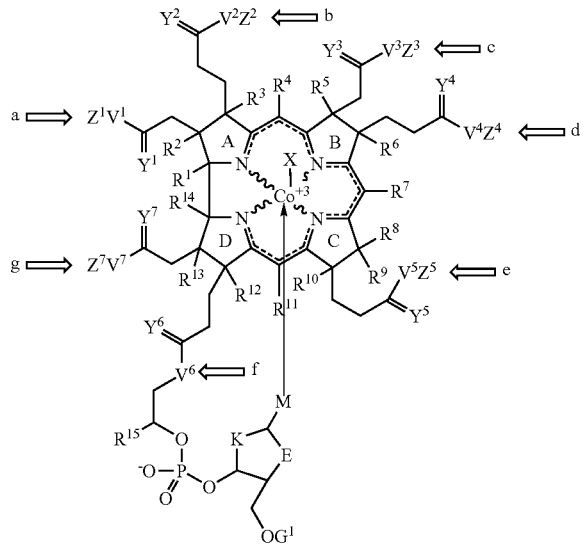

or its enantiomer, diastereomer or its pharmaceutically acceptable salt, wherein:

(i) the wavy line in the chemical structure indicates either a dative or covalent bond such that there are three dative Co—N bonds and one covalent Co—N bond, wherein, in the case of the dative bond, the valence of nitrogen is completed either with a double bond with an adjacent ring carbon or with a hydrogen;

(ii) the dotted line in the chemical structure indicates either a double or single bond such that the double bond does not over-extend the valence of the element and, in the case of a single bond, the valence is completed with hydrogen;

(iii) X is hydrogen, cyano, halogen, haloalkyl, NO, $NO_2$, $NO_3$, phosphonate, $PR^{15}R^{16}R^{17}$, $NH_2$, $NR^{15}R^{16}$, OH, $OR^{15}$, $SR^{15}$, SCN, $N_3$, $OC(O)R^{15}$, $C(O)_2R^{15}$, $C(O)R^{15}$, $OC(O)NR^{15}R^{16}$, $C(O)_2NR^{15}R^{16}$, $C(O)NR^{15}R^{16}$, $P(O)_2OR^{15}$, $S(O)_2R^{15}$, a purine or pyrimidine nucleoside or nucleoside analog, adenosyl, 5-FU, alkyl, alkenyl, alkynyl, aryl, aralkyl, alkaryl, amino acid, peptide, protein, carbohydrate, heteroalkyl, heterocycle, heteroaryl or alkylheteroaryl;

(iv) M is a monovalent heterocycle or heteroaromatic, which is capable of binding to the adjacent sugar ring, and forming a dative bond with $Co^{+3}$;

(v) K is O, S, $NJ^1$, C(OH)H, $CR^{100}R^{101}$ or $C(R^{100})V^8Z^8$;

(vi) E is O or S;

(vii) $G^1$ is hydrogen, alkyl, acyl, silyl, phosphate or L-T;

(viii) $Y^1$, $Y^2$, $Y^3$, $Y^4$, $Y^5$, $Y^6$ and $Y^7$ independently are O, S or $NJ^2$;

(ix) $V^1$, $V^2$, $V^3$, $V^4$, $V^5$, $V^6$, $V^7$ and $V^8$ independently are O, S, $NJ^3$, $CR^{102}R^{103}$ or a direct bond;

(x) $Z^1$, $Z^2$, $Z^3$, $Z^4$, $Z^5$, $Z^7$ and $Z^8$ independently are $R^{104}$ or L-T;

(xi) each L is independently a direct bond or linker, of a singular molecular weight, to one or more T moieties, and that does not significantly impair the ability of the TC- or IF-binding carrier to bind to a transcobalamin receptor, optionally when bound to a transport protein;

(xii) each T independently comprises the residue of a diagnostic agent effective for the diagnosis of a proliferative disorder, optionally bound though a chelating moiety;

(xiii) at least one of $Z^1$, $Z^2$, $Z^3$, $Z^4$, $Z^5$, $Z^7$, $Z^8$, K and $G^1$ is L-T;

(xiv) $J^1$, $J^2$ and $J^3$ independently are hydrogen, alkyl, alkenyl, alkynyl, alkaryl, cycloalkyl, aryl, cycloaryl, heteroalkyl, heterocycle, heteroaryl, hydroxyl, alkoxy or amine;

(xv) $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ independently are hydrogen, lower alkyl, lower alkenyl, lower alkynyl, lower cycloalkyl, heteroalkyl, heterocyclic, lower alkoxy, azido, amino, lower alkylamino, halogen, thiol, $SO_2$, $SO_3$, carboxylic acid, $C_{1-6}$ carboxyl, hydroxyl, nitro, cyano, oxime or hydrazine;

(xvi) $R^{13}$ and $R^{14}$ optionally can form a double bond;

(xvii) $R^{15}$, $R^{16}$ and $R^{17}$ are independently hydrogen, alkyl, alkenyl, alkynyl, aryl, alkaryl or aralkyl group, heteroalkyl, heterocycle or heteroaromatic; and (xviii) $R^{100}$, $R^{101}$, $R^{102}$, $R^{103}$, and $R^{104}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl or amino;

(xix) wherein at least one of Y, R, G, E, K, M and V is not as it is found in natural vitamin $B_{12}$;

(xx) wherein at least one -L-T is independently a poly-L-lysine-NR'(CH((CH$_2$)$_4$ —NHR')CONR')$_m$R', wherein each R' is independently hydrogen, lower alkyl or T; and m is 2-20; and (xxi) wherein at least one T is a detectable radionuclide.

4. A compound of the formula (I):

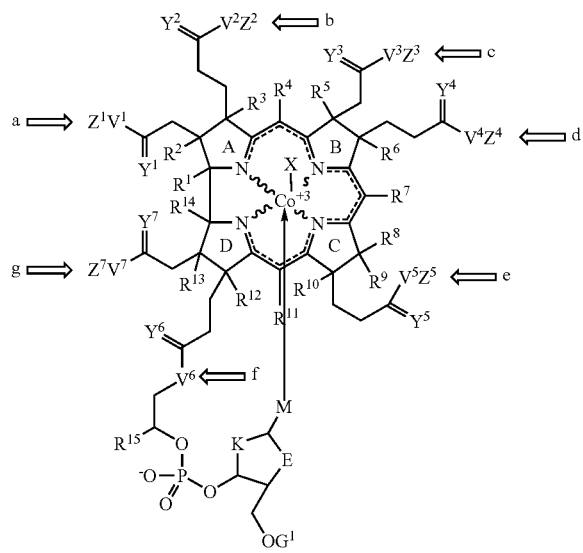

or its enantiomer, diastereomer or its pharmaceutically acceptable salt, wherein:

(i) the wavy line in the chemical structure indicates either a dative or covalent bond such that there are three dative Co—N bonds and one covalent Co—N bond, wherein, in the case of the dative bond, the valence of nitrogen is completed either with a double bond with an adjacent ring carbon or with a hydrogen;

(ii) the dotted line in the chemical structure indicates either a double or single bond such that the double bond does not over-extend the valence of the element and, in the case of a single bond, the valence is completed with hydrogen;

(iii) X is hydrogen, cyano, halogen, haloalkyl, NO, $NO_2$, $NO_3$, phosphonate, $PR^{15}R^{16}R^{17}$, $NH_2$, $NR^{15}R^{16}$, OH, $OR^{15}$, $SR^{15}$, SCN, $N_3$, $OC(O)R^{15}$, $C(O)_2R^{15}$, $C(O)R^{15}$, $OC(O)NR^{15}R^{16}$, $C(O)_2NR^{15}R^{16}$, $C(O)NR^{15}R^{16}$, $P(O)_2OR^{15}$, $S(O)_2R^{15}$, a purine or pyrimidine nucleoside or nucleoside analog, adenosyl, 5-FU, alkyl, alkenyl, alkynyl, aryl, aralkyl, alkaryl, amino acid, peptide, protein, carbohydrate, heteroalkyl, heterocycle, heteroaryl or alkylheteroaryl;

(iv) M is a monovalent heterocycle or heteroaromatic, which is capable of binding to the adjacent sugar ring, and forming a dative bond with $Co^{+3}$;

(v) K is O, S, $NJ^1$, C(OH)H, $CR^{100}R^{101}$ or $C(R^{100})V^8Z^8$;

(vi) E is O or S;

(vii) $G^1$ is hydrogen, alkyl, acyl, silyl, phosphate or L-T;

(viii) $Y^1, Y^2, Y^3, Y^4, Y^5, Y^6$ and $Y^7$ independently are O, S or $NJ^2$;

(ix) $V^1, V^2, V^3, V^4, V^5, V^6, V^7$ and $V^8$ independently are O, S, $NJ^3$, $CR^{102}R^{103}$ or a direct bond;

(x) $Z^1, Z^2, Z^3, Z^4, Z^5, Z^7$ and $Z^8$ independently are $R^{104}$ or L-T;

(xi) each L is independently a direct bond or linker, of a singular molecular weight, to one or more T moieties, and that does not significantly impair the ability of the TC- or IF-binding carrier to bind to a transcobalamin receptor, optionally when bound to a transport protein;

(xii) each T independently comprises the residue of a diagnostic agent effective for the diagnosis of a proliferative disorder, optionally bound though a chelating moiety;

(xiii) at least one of $Z^1, Z^2, Z^3, Z^4, Z^5, Z^7, Z^8$, K and $G^1$ is L-T;

(xiv) $J^1, J^2$ and $J^3$ independently are hydrogen, alkyl, alkenyl, alkynyl, alkaryl, cycloalkyl, aryl, cycloaryl, heteroalkyl, heterocycle, heteroaryl, hydroxyl, alkoxy or amine;

(xv) $R^1, R^2, R^3, R^4, R^5, R^6, R^7, R^8, R^9, R^{10}, R^{11}, R^{12}, R^{13}$ and $R^{14}$ independently are hydrogen, lower alkyl, lower alkenyl, lower alkynyl, lower cycloalkyl, heteroalkyl, heterocyclic, lower alkoxy, azido, amino, lower alkylamino, halogen, thiol, $SO_2$, $SO_3$, carboxylic acid, $C_{1-6}$ carboxyl, hydroxyl, nitro, cyano, oxime or hydrazine;

(xvi) $R^{13}$ and $R^{14}$ optionally can form a double bond;

(xvii) $R^{15}, R^{16}$ and $R^{17}$ are independently hydrogen, alkyl, alkenyl, alkynyl, aryl, alkaryl or aralkyl group, heteroalkyl, heterocycle or heteroaromatic; and (xviii) $R^{100}, R^{101}, R^{102}, R^{103}$, and $R^{104}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl or amino;

(xix) wherein at least one of Y, R, G, E, K, M and V is not as it is found in natural vitamin $B_{12}$;

(xx) wherein at least one -L-T is independently a polyamine residue of the formula —NR'(alkylene-NR')$_n$alkyleneNR'R', wherein each R' is independently hydrogen, lower alkyl or T and n is 1-20; and (xxi) wherein at least one T is a detectable radionuclide.

5. The compound of claim 2 or 4, wherein —NR'(alkylene-NR')$_n$alkyleneNR' is selected from the group consisting of —NR'(CH$_2$)$_3$NR'(CH$_2$)$_4$NR'(CH$_2$)$_3$NR'R'; —NR'(CH$_2$)$_3$NR'(CH$_2$)$_4$NR'R'; decamethylene tetraamine and pentamethylene hexamine.

6. A pharmaceutical composition for the diagnosis of a proliferative disorder in a host comprising a compound of claim 1, 2, 3, and 4, or the pharmaceutically acceptable salt thereof, in combination with a pharmaceutically acceptable carrier.

7. A pharmaceutical composition for the diagnosis of a proliferative disorder in a host comprising a compound of claim 1, 2, 3, and 4, or the pharmaceutically acceptable salt thereof, optionally in a pharmaceutically acceptable carrier, in combination with one or more other diagnostic agent(s).

8. The pharmaceutical composition of claim 6, wherein the host is a human.

9. The pharmaceutical composition of claim 7, wherein the host is a human.

* * * * *

UNITED STATES PATENT AND TRADEMARK OFFICE
CERTIFICATE OF CORRECTION

PATENT NO.        : 7,531,162 B2  
APPLICATION NO. : 11/353810  
DATED              : May 12, 2009  
INVENTOR(S)       : Douglas A. Collins Page 1 of 1

It is certified that error appears in the above-identified patent and that said Letters Patent is hereby corrected as shown below:

Column 89, line 38 (Claim 1), please delete "though" and insert --through-- therefor;

Column 90, line 41 (Claim 2), please delete "$OR^{16}$" and insert --$OR^{15}$-- therefor;

Column 90, line 47 (Claim 2), please delete "alkyiheteroaryl;" and insert --alkylheteroaryl;-- therefor;

Column 90, line 67 (Claim 2), please delete "though" and insert --through-- therefor;

Column 92, line 14 (Claim 3), please delete "alkyiheteroaryl;" and insert --alkylheteroaryl;-- therefor;

Column 92, line 37 (Claim 3), please delete "though" and insert --through-- therefor;

Column 93, line 47 (Claim 4), please delete "alkyiheteroaryl;" and insert --alkylheteroaryl;-- therefor;

Column 94, line 10 (Claim 4), please delete "though" and insert --through-- therefor.

Signed and Sealed this

Eighteenth Day of August, 2009

David J. Kappos  
*Director of the United States Patent and Trademark Office*